(12) United States Patent
Bell et al.

(10) Patent No.: US 9,283,254 B2
(45) Date of Patent: Mar. 15, 2016

(54) COMPOSITIONS AND METHODS FOR ENHANCING VIRUS EFFICACY

(71) Applicant: Ottawa Hospital Research Institute, Ottawa (CA)

(72) Inventors: John Bell, Ottawa (CA); Jean-Simon Diallo, Ottawa (CA); Fabrice Le Boeuf, Gatineau (CA)

(73) Assignee: Ottawa Hospital Research Institute, Ottawa (CA)

( * ) Notice: Subject to any disclaimer, the term of this patent is extended or adjusted under 35 U.S.C. 154(b) by 0 days.

(21) Appl. No.: 14/569,416

(22) Filed: Dec. 12, 2014

(65) Prior Publication Data

US 2015/0202240 A1 Jul. 23, 2015

Related U.S. Application Data

(62) Division of application No. 13/382,355, filed as application No. PCT/CA2010/001057 on Jul. 7, 2010, now Pat. No. 8,940,291.

(60) Provisional application No. 61/270,345, filed on Jul. 7, 2009.

(30) Foreign Application Priority Data

Nov. 16, 2009 (CA) ..................................... 2689707

(51) Int. Cl.
| | |
|---|---|
| *A61K 35/766* | (2015.01) |
| *A61K 31/341* | (2006.01) |
| *A61K 45/06* | (2006.01) |
| *C07C 49/675* | (2006.01) |
| *C07C 49/747* | (2006.01) |
| *C07C 205/37* | (2006.01) |
| *C07C 217/84* | (2006.01) |
| *C07C 233/32* | (2006.01) |
| *C07C 233/38* | (2006.01) |
| *C07C 243/38* | (2006.01) |
| *C07C 255/37* | (2006.01) |
| *C07C 311/44* | (2006.01) |
| *C07C 323/42* | (2006.01) |
| *C07C 323/60* | (2006.01) |
| *C07C 335/16* | (2006.01) |
| *C07C 337/06* | (2006.01) |
| *C07C 337/08* | (2006.01) |
| *C07D 213/75* | (2006.01) |
| *C07D 233/90* | (2006.01) |
| *C07D 257/04* | (2006.01) |
| *C07D 307/58* | (2006.01) |
| *C07D 319/20* | (2006.01) |
| *C07D 333/04* | (2006.01) |
| *C07D 403/12* | (2006.01) |
| *C07D 409/12* | (2006.01) |
| *C12N 7/00* | (2006.01) |
| *A61K 31/275* | (2006.01) |
| *A61K 31/365* | (2006.01) |
| *A61K 38/00* | (2006.01) |

(52) U.S. Cl.
CPC ............. *A61K 35/766* (2013.01); *A61K 31/275* (2013.01); *A61K 31/341* (2013.01); *A61K 31/365* (2013.01); *A61K 45/06* (2013.01); *C07C 49/675* (2013.01); *C07C 49/747* (2013.01); *C07C 205/37* (2013.01); *C07C 217/84* (2013.01); *C07C 233/32* (2013.01); *C07C 233/38* (2013.01); *C07C 243/38* (2013.01); *C07C 255/37* (2013.01); *C07C 311/44* (2013.01); *C07C 323/42* (2013.01); *C07C 323/60* (2013.01); *C07C 335/16* (2013.01); *C07C 337/06* (2013.01); *C07C 337/08* (2013.01); *C07D 213/75* (2013.01); *C07D 233/90* (2013.01); *C07D 257/04* (2013.01); *C07D 307/58* (2013.01); *C07D 319/20* (2013.01); *C07D 333/04* (2013.01); *C07D 403/12* (2013.01); *C07D 409/12* (2013.01); *C12N 7/00* (2013.01); *A61K 38/00* (2013.01); *C07C 2101/02* (2013.01); *C07C 2101/14* (2013.01); *C07C 2103/26* (2013.01); *C07C 2103/34* (2013.01); *C12N 2760/20232* (2013.01); *C12N 2760/20251* (2013.01)

(58) Field of Classification Search
CPC ....................................................... A61K 35/766
See application file for complete search history.

(56) References Cited

U.S. PATENT DOCUMENTS

| 4,292,431 A | 9/1981 | Kim et al. |
|---|---|---|
| 8,940,291 B2 | 1/2015 | Bell et al. |
| 2005/0153059 A1 | 7/2005 | Wakizaka |

FOREIGN PATENT DOCUMENTS

| CA | 2689707 A1 | 5/2011 |
|---|---|---|
| WO | WO 99/52888 A1 | 10/1999 |

(Continued)

OTHER PUBLICATIONS

International Search Report and Written Opinion from international PCT application, PCT/CA2010/001057, mailed Oct. 6, 2010.
International Preliminary Report on Patentability from international PCT application, PCT/CA2010/001057, mailed Jan. 19, 2012.
Extended European Search Report from EP 10796623.6 mailed Jan. 10, 2013.
Adusumilli et al., Cisplatin-induced GADD34 upregulation potentiates oncolytic viral therapy in the treatment of malignant pleural mesothelioma. Cancer Biol Ther. Jan. 2006;5(1):48-53. Epub Jan. 12, 2006.
Ahmed et al., Sensitivity of prostate tumors to wild type and M protein mutant vesicular stomatitis viruses. Virology. Dec. 5, 2004;330(1):34-49.

(Continued)

*Primary Examiner* — Paul Zarek
(74) *Attorney, Agent, or Firm* — Wolf, Greenfield & Sacks, P.C.

(57) ABSTRACT

Provided are viral sensitizing compounds that enhance the efficacy of viruses by increasing spread of the virus in cells, increasing the titer of virus in cells, or increasing the cytotoxicity of virus to cells. Other uses, compositions and methods of using same are also provided.

9 Claims, 42 Drawing Sheets

(56) References Cited

FOREIGN PATENT DOCUMENTS

| WO | WO 00/54795 A1 | 9/2000 |
|---|---|---|
| WO | WO 03/033480 A1 | 4/2003 |
| WO | WO 2004/106315 A2 | 12/2004 |
| WO | WO 2005/066163 A2 | 7/2005 |
| WO | WO 2008/043576 A1 | 4/2008 |
| WO | WO 2008/144067 A1 | 11/2008 |
| WO | WO 2009/067397 A2 | 5/2009 |
| WO | WO 2009/073620 A2 | 6/2009 |
| WO | WO 2010/080864 A1 | 7/2010 |

OTHER PUBLICATIONS

Bennet et al., Up-regulation of GADD34 mediates the synergistic anticancer activity of mitomycin C and a gamma134.5 deleted oncolytic herpes virus (G207). FASEB J. Jun. 2004;18(9):1001-3. Epub Apr. 1, 2004.
Brideau et al., Improved statistical methods for hit selection in high-throughput screening. J Biomol Screen. Dec. 2003;8(6):634-47.
CAS Registry File RN 1009294-78-3, STN Entry Date: Mar. 20, 2008.
CAS Registry File RN 1052410-02-2, STN Entry Date: Sep. 25, 2008.
CAS Registry File RN 14770-84-4, STN Entry Date: Nov. 16, 1984.
CAS Registry File RN 666727-99-7, STN Entry Date: Mar. 23, 2004.
CAS Registry File RN 666728-23-0, STN Entry Date: Mar. 23, 2004.
CAS Registry File RN 72857-85-3, STN Entry Date: Nov. 16, 1984.
CAS Registry File RN 77498-98-7, STN Entry Date: Nov. 16, 1984.
CAS Registry File RN 883028-46-4, STN Entry Date: May 5, 2006.
Chalikonda et al., Oncolytic virotherapy for ovarian carcinomatosis using a replication-selective vaccinia virus armed with a yeast cytosine deaminase gene. Cancer Gene Ther. Feb. 2008;15(2):115-25. Epub Dec. 14, 2007.
Chang et al., Induction of interferon-stimulated gene expression and antiviral responses require protein deacetylase activity. Proc Natl Acad Sci U S A. Jun. 29, 2004;101(26):9578-83. Epub Jun. 21, 2004.
Chen et al., Oncolytic adenovirus-mediated transfer of the antisense chk2 selectively inhibits tumor growth in vitro and in vivo. Cancer Gene Ther. Oct. 2006;13(10):930-9. Epub Jun. 2, 2006.
Cheong et al., E1A-expressing adenoviral E3B mutants act synergistically with chemotherapeutics in immunocompetent tumor models. Cancer Gene Ther. Jan. 2008;15(1):40-50. Epub Nov. 23, 2007.
Chou et al., A simple generalized equation for the analysis of multiple inhibitions of Michaelis-Menten kinetic systems. J Biol Chem. Sep. 25, 1977;252(18):6438-42.
Ebert et al., Systemic therapy of experimental breast cancer metastases by mutant vesicular stomatitis virus in immune-competent mice. Cancer Gene Ther. Apr. 2005;12(4):350-8.
Foloppe et al., Targeted delivery of a suicide gene to human colorectal tumors by a conditionally replicating vaccinia virus. Gene Ther. Oct. 2008;15(20):1361-71. Epub May 15, 2008.
Freytag et al., Replication-competent adenovirus-mediated suicide gene therapy with radiation in a preclinical model of pancreatic cancer. Mol Ther. Sep. 2007;15(9):1600-6. Epub Jun. 12, 2007.
Fukuda et al., E1A, E1B double-restricted replicative adenovirus at low dose greatly augments tumor-specific suicide gene therapy for gallbladder cancer. Cancer Gene Ther. Feb. 2009;16(2):126-36. Epub Sep. 26, 2008.
Galanis et al., Phase I-II trial of Onyx-015 in combination with MAP chemotherapy in patients with advanced sarcomas. Gene Ther. Mar. 2005;12(5):437-45.
Gao et al., Selective targeting of checkpoint kinase 1 in tumor cells with a novel potent oncolytic adenovirus. Mol Ther. May 2006;13(5):928-37. Epub Feb. 3, 2006.
Graat et al., Different susceptibility of osteosarcoma cell lines and primary cells to treatment with oncolytic adenovirus and doxorubicin or cisplatin. Br J Cancer. Jun. 19, 2006;94(12):1837-44. Epub May 30, 2006.
Hsieh et al., Transthyretin-driven oncolytic adenovirus suppresses tumor growth in orthotopic and ascites models of hepatocellular carcinoma. Cancer Sci. Mar. 2009;100(3):537-45. Epub Jan. 6, 2009.
Hsu et al., Conditionally replicating E1B-deleted adenovirus driven by the squamous cell carcinoma antigen 2 promoter for uterine cervical cancer therapy. Cancer Gene Ther. Aug. 2008;15(8):526-34. Epub May 23, 2008.
Ikeda et al., Complement depletion facilitates the infection of multiple brain tumors by an intravascular, replication-conditional herpes simplex virus mutant. J Virol. May 2000;74(10):4765- 75.
Ikeda et al., Oncolytic virus therapy of multiple tumors in the brain requires suppression of innate and elicited antiviral responses. Nat Med. Aug. 1999;5(8):881-7.
Kambara et al., Cyclophosphamide allows for in vivo dose reduction of a potent oncolytic virus. Cancer Res. Dec. 15, 2005;65(24):11255-8.
Kasuya et al., Suitability of a US3-inactivated HSV mutant (L1BR1) as an oncolytic virus for pancreatic cancer therapy. Cancer Gene Ther. Jun. 2007;14(6):533-42. Epub Apr. 6, 2007.
Kim et al., Imaging of viral thymidine kinase gene expression by replicating oncolytic adenovirus and prediction of therapeutic efficacy. Yonsei Med J. Oct. 31, 2008;49(5):811-8.
Kottke et al., Improved systemic delivery of oncolytic reovirus to established tumors using preconditioning with cyclophosphamide-mediated Treg modulation and interleukin-2. Clin Cancer Res. Jan. 15, 2009;15(2):561-9.
Kramm et al., Long-term survival in a rodent model of disseminated brain tumors by combined intrathecal delivery of herpes vectors and ganciclovir treatment. Hum Gene Ther. Oct. 20, 1996;7(16):1989-94.
Kurozumi et al., Effect of tumor microenvironment modulation on the efficacy of oncolytic virus therapy. J Natl Cancer Inst. Dec. 5, 2007;99(23):1768-81. Epub Nov. 27, 2007.
Kurozumi et al., Oncolytic HSV-1 infection of tumors induces angiogenesis and upregulates CYR61. Mol Ther. Aug. 2008;16(8):1382-91. Epub Jun. 10, 2008.
Lattmann et al., Synthesis and evaluation of 5-arylated 2(5H)-furanones and 2-arylated pyridazin-3(2H)-ones as anti-cancer agents. J Pharm Pharmacol. Sep. 2003;55(9):1259-65.
Lun et al., Effects of intravenously administered recombinant vesicular stomatitis virus (VSV(deltaM51)) on multifocal and invasive gliomas. J Natl Cancer Inst. Nov. 1, 2006;98(21):1546-57.
Lun et al., Targeting human medulloblastoma: oncolytic virotherapy with myxoma virus is enhanced by rapamycin. Cancer Res. Sep. 15, 2007;67(18):8818-27.
Lun et al., Efficacy of systemically administered oncolytic vaccinia virotherapy for malignant gliomas is enhanced by combination therapy with rapamycin or cyclophosphamide. Clin Cancer Res. Apr. 15, 2009;15(8):2777-88. Epub Apr. 7, 2009.
Mace et al., Cytotoxic effects of the oncolytic herpes simplex virus HSV1716 alone and in combination with cisplatin in head and neck squamous cell carcinoma. Acta Otolaryngol. Aug. 2007;127(8):880-7.
Mai et al., New pyrrole-based histone deacetylase inhibitors: binding mode, enzyme- and cell-based investigations. Int J Biochem Cell Biol. Jan. 2009;41(1):235-47. Epub Sep. 12, 2008.
McCart et al., Complex interactions between the replicating oncolytic effect and the enzyme/prodrug effect of vaccinia-mediated tumor regression. Gene Ther. Jul. 2000;7(14):1217-23.
Monneret, Histone deacetylase inhibitors. Eur J Med Chem. Jan. 2005;40(1):1-13.
Morse, Virus-based therapies for colon cancer. Expert Opin Biol Ther. Dec. 2005;5(12):1627-33.
Mullerad et al., Herpes simplex virus based gene therapy enhances the efficacy of mitomycin C for the treatment of human bladder transitional cell carcinoma. J Urol. Aug. 2005;174(2):741-6.
Nawa et al., Oncolytic viral therapy for human ovarian cancer using a novel replication-competent herpes simplex virus type I mutant in a mouse model. Gynecol Oncol. Oct. 2003;91(1):81-8.
Nguyên et al., Chemical targeting of the innate antiviral response by histone deacetylase inhibitors renders refractory cancers sensitive to viral oncolysis. Proc Natl Acad Sci U S A. Sep. 30, 2008;105(39):14981-6. Epub Sep. 24, 2008.
Pan et al., Synergistic induction of tumor cell death by combining cisplatin with an oncolytic adenovirus carrying TRAIL. Mol Cell Biochem. Oct. 2007;304(1-2):315-23. Epub Jun. 19, 2007.

(56) References Cited

OTHER PUBLICATIONS

Pan et al., Enhanced sensitivity of hepatocellular carcinoma cells to chemotherapy with a Smac-armed oncolytic adenovirus. Acta Pharmacol Sin. Dec. 2007;28(12):1996-2004.
Parato et al., Recent progress in the battle between oncolytic viruses and tumours. Nat Rev Cancer. Dec. 2005;5(12):965-76.
Pawlik et al., Prodrug bioactivation and oncolysis of diffuse liver metastases by a herpes simplex virus 1 mutant that expresses the CYP2B1 transgene. Cancer. Sep. 1, 2002;95(5):1171-81.
Qiao et al., Cyclophosphamide facilitates antitumor efficacy against subcutaneous tumors following intravenous delivery of reovirus. Clin Cancer Res. Jan. 1, 2008;14(1):259-69.
Reddy et al., Seneca Valley virus, a systemically deliverable oncolytic picornavirus, and the treatment of neuroendocrine cancers. J Natl Cancer Inst. Nov. 7, 2007;99(21):1623-33. Epub Oct. 30, 2007.
Ryan et al., Antitumor efficacy and tumor-selective replication with a single intravenous injection of OAS403, an oncolytic adenovirus dependent on two prevalent alterations in human cancer. Cancer Gene Ther. Aug. 2004;11(8):555-69.
Sieben et al., Killing of p53-deficient hepatoma cells by parvovirus H-1 and chemotherapeutics requires promyelocytic leukemia protein. World J Gastroenterol. Jun. 28, 2008;14(24):3819-28.
Sung et al., Combined VSV oncolytic virus and chemotherapy for squamous cell carcinoma. Laryngoscope. Feb. 2008;118(2):237-42.
Stanford et al., Oncolytic virotherapy synergism with signaling inhibitors: Rapamycin increases myxoma virus tropism for human tumor cells. J Virol. Feb. 2007;81(3):1251-60. Epub Nov. 15, 2006.
Stanford et al., Myxoma virus oncolysis of primary and metastatic B16F10 mouse tumors in vivo. Mol Ther. Jan. 2008;16(1):52-9. Epub Nov. 13, 2007.
Stojdl et al., Exploiting tumor-specific defects in the interferon pathway with a previously unknown oncolytic virus. Nat Med. Jul. 2000;6(7):821-5.
Stojdl et al., VSV strains with defects in their ability to shutdown innate immunity are potent systemic anti-cancer agents. Cancer Cell. Oct. 2003;4(4):263-75.
Taneja et al., Enhanced antitumor efficacy of a herpes simplex virus mutant isolated by genetic selection in cancer cells. Proc Natl Acad Sci U S A. Jul. 17, 2001;98(15):8804-8. Epub Jul. 3, 2001
Thomas et al., Immunosuppression enhances oncolytic adenovirus replication and antitumor efficacy in the Syrian hamster model. Mol Ther. Oct. 2008;16(10):1665-73. Epub Jul. 29, 2008.
Tomicic et al., Ganciclovir-induced apoptosis in HSV-1 thymidine kinase expressing cells: critical role of DNA breaks, Bcl-2 decline and caspase-9 activation. Oncogene. Mar. 28, 2002;21(14):2141-53.
Toyoizumi et al., Combined therapy with chemotherapeutic agents and herpes simplex virus type 1 ICP34.5 mutant (HSV-1716) in human non-small cell lung cancer. Hum Gene Ther. Dec. 10, 1999;10(18):3013-29.
Tumilasci et al., Targeting the apoptotic pathway with BCL-2 inhibitors sensitizes primary chronic lymphocytic leukemia cells to vesicular stomatitis virus-induced oncolysis. J Virol. Sep. 2008;82(17):8487-99. Epub Jun. 25, 2008.
Ungerechts et al., An immunocompetent murine model for oncolysis with an armed and targeted measles virus. Mol Ther. Nov. 2007;15(11):1991-7. Epub Aug. 21, 2007.
Yoon et al., Markedly enhanced cytolysis by E1B-19kD-deleted oncolytic adenovirus in combination with cisplatin. Hum Gene Ther. Apr. 2006;17(4):379-90.
Yu et al., Antitumor synergy of CV787, a prostate cancer-specific adenovirus, and paclitaxel and docetaxel. Cancer Res. Jan. 15, 2001;61(2):517-25.
Yu et al., Regression of human pancreatic tumor xenografts in mice after a single systemic injection of recombinant vaccinia virus GLV-1h68. Mol Cancer Ther. Jan. 2009;8(1):141-51.
Zhang et al., Identification of human uroplakin II promoter and its use in the construction of CG8840, a urothelium-specific adenovirus variant that eliminates established bladder tumors in combination with docetaxel. Cancer Res. Jul. 1, 2002;62(13):3743-50.
Zhang et al., Proteasome inhibitor MG-132 modifies coxsackie and adenovirus receptor expression in colon cancer cell line lovo. Cell Cycle. Apr. 1, 2008;7(7):925-33. Epub Jan. 17, 2008.
Zhou et al., Novel oncolytic adenovirus selectively targets tumor-associated polo-like kinase 1 and tumor cell viability. Clin Cancer Res. Dec. 1, 2005;11(23):8431-40.

Figure 1

Effect of 3,4 Dichloro-5-Phenyl-2,5-Dihydrofuranone (DCPDF) on VSVΔ51 spread in CT26 cells (42h incubation)

DMSO    DCPDF 1.25 µM    DCPDF 2.5 µM

DCPDF 5 µM    DCPDF 10 µM    DCPDF 20 µM

VSVΔ51-RFP on 4T1 cells 40h incubation

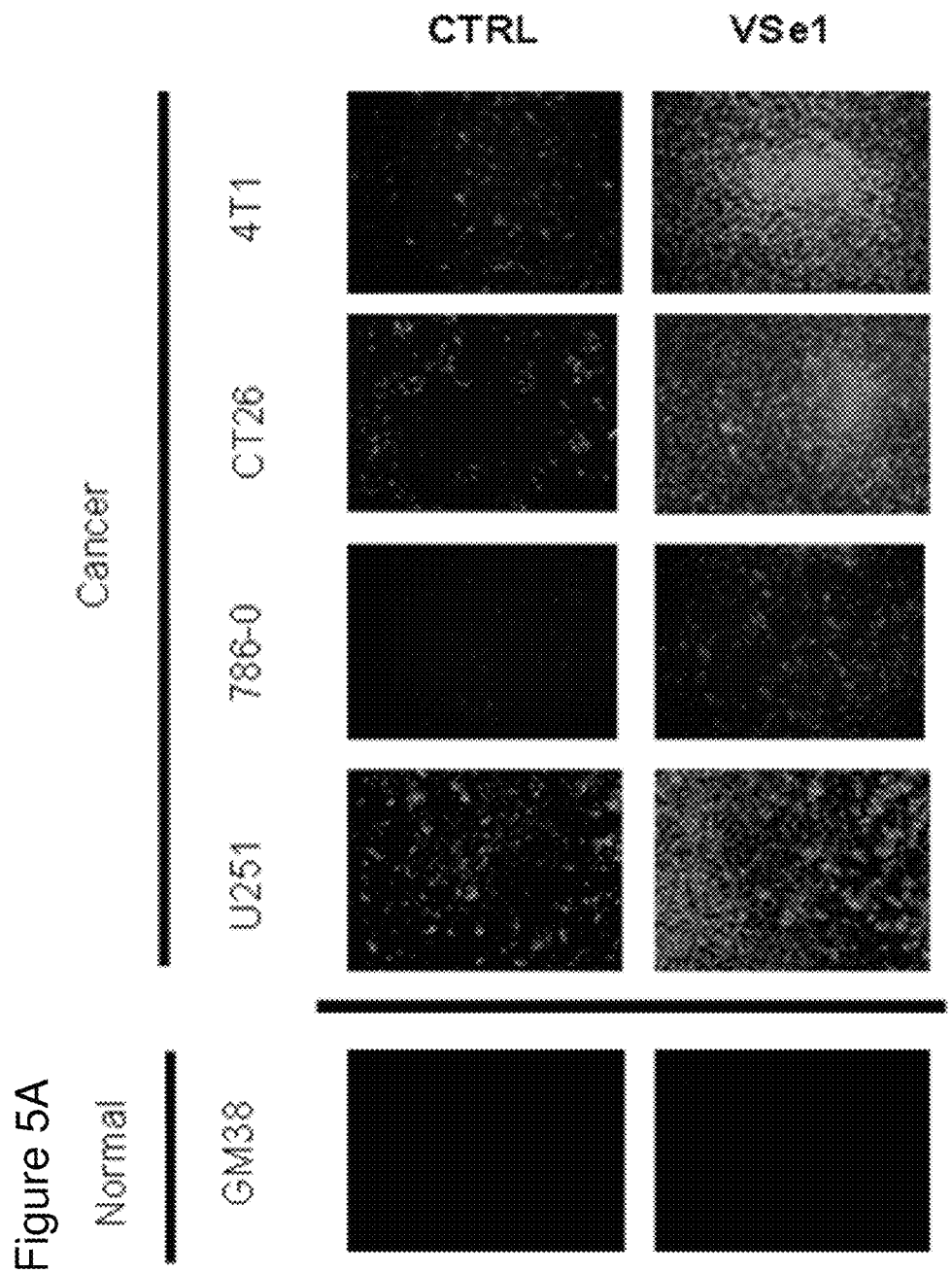

Figure 7A
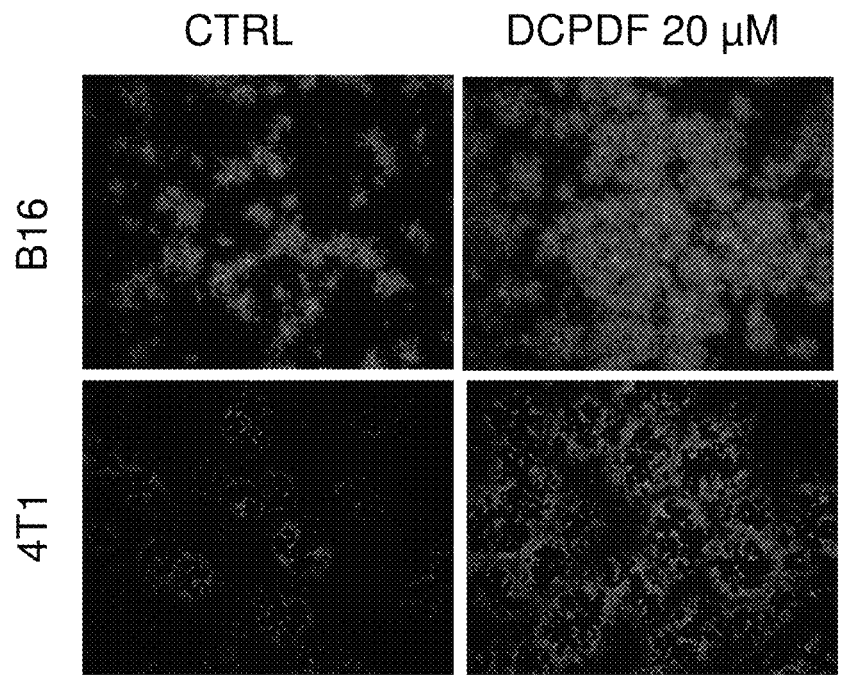
Figure 7B Effect of DCPDF on Vvdd titers
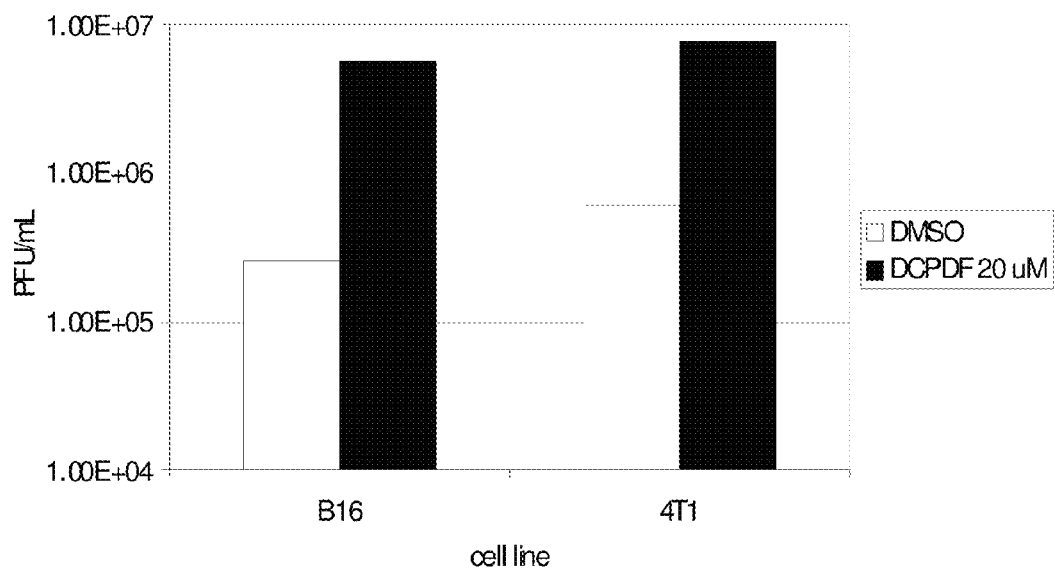

|  | CTRL (0h) | TSA 24h | DCPDF 24h | TSA 48h | DCPDF 48h |
|---|---|---|---|---|---|
| G1 | 56.04 | 58.41 | 63.62 | 72.65 | 88.91 |
| G2 | 13.47 | 8.83 | 23.82 | 15.8 | 8.3 |
| S | 30.49 | 32.76 | 12.56 | 11.56 | 2.78 |
| G1/G2 | 1.88 | 1.88 | 1.94 | 1.94 | 1.99 |
| Ap | 0.87 | 0.33 | 0.1 | 2.76 | 0.09 |

Figure 10A
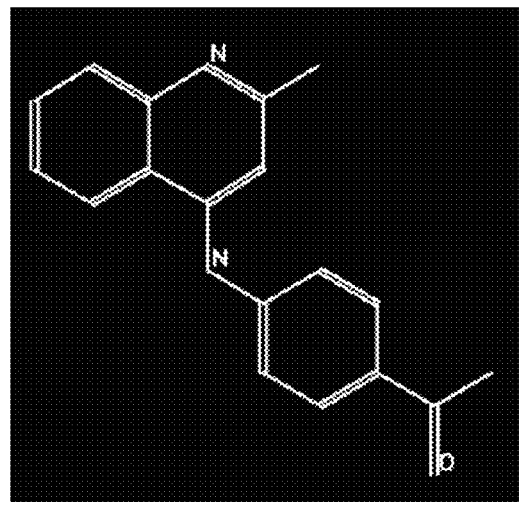
RH01894: 1-{4-[(2-methylquinolin-4-yl)amino]phenyl}ethan-1-one(*MQAPE*)
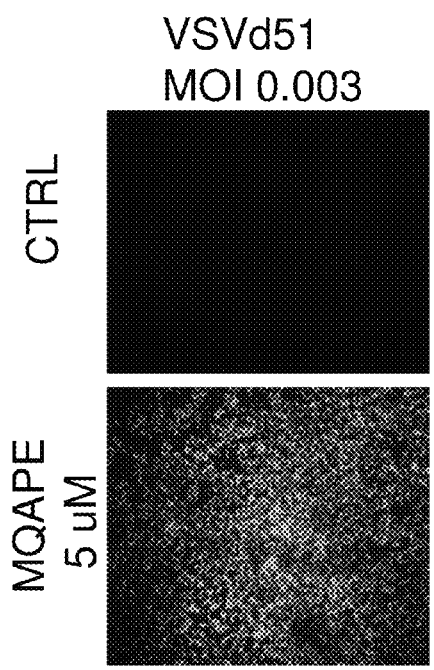
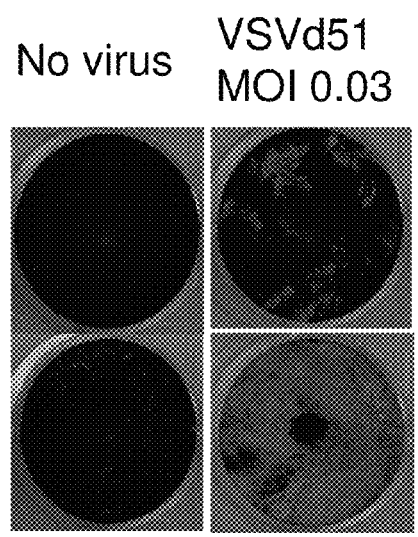

JFD 01080: 4',5'-dihydro-4'-(5-methoxyphenyl)spiro[2H-1-benzothiopyran-3(4H)m3'-[3H]pyrazole]-4-one (DMSBP)

Figure 10C
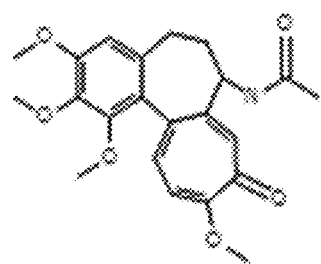
BTB12749: 4',5'-dihydro-4'-(5-methoxyphenyl)spiro[2H-1-benzothiopyran-3(4H)m3'-[3H]pyrazole]-4-one
BTB 12749
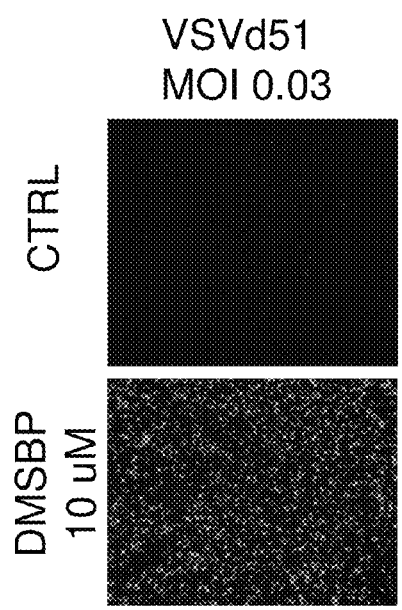
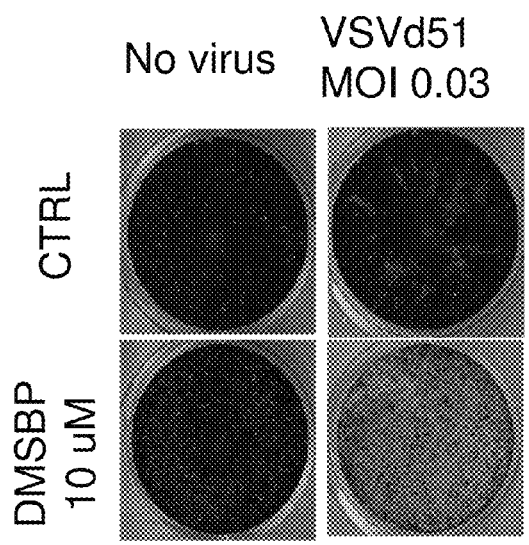

Figure 10D

JFD03665: 10-(hydroxymethylene)phenanthren-9(10H)-one(HMPO)

JFD 03665

|  | No virus | VSVd51 MOI 0.03 |
|---|---|---|
| CTRL | | |
| HMPO 2.5 uM | | |

Figure 10E
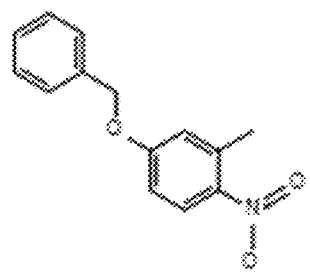
JRH01502: 4-(benzyloxy)-2-methyl-1-nitrobenzene (*BMNB*)
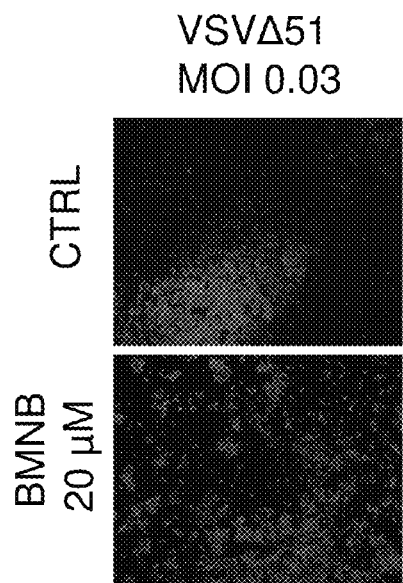
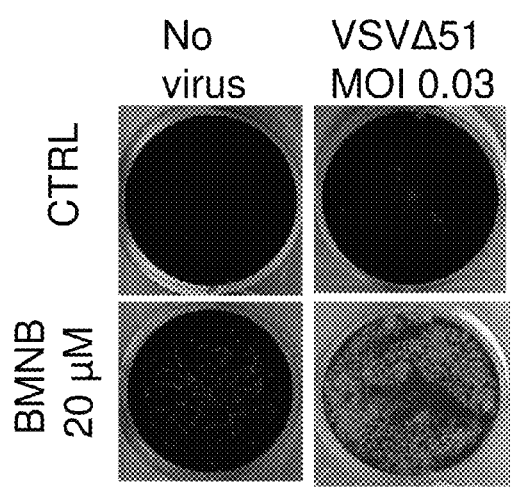

Figure 10F
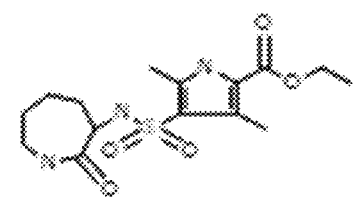
SCR 01004
SCR01004: ethyl 3,5-dimethyl-4-{[(2-oxo-3-azepanyl)amino]sulfonyl}-1H-pyrrole-2-carboxylate (*EDOPC*)
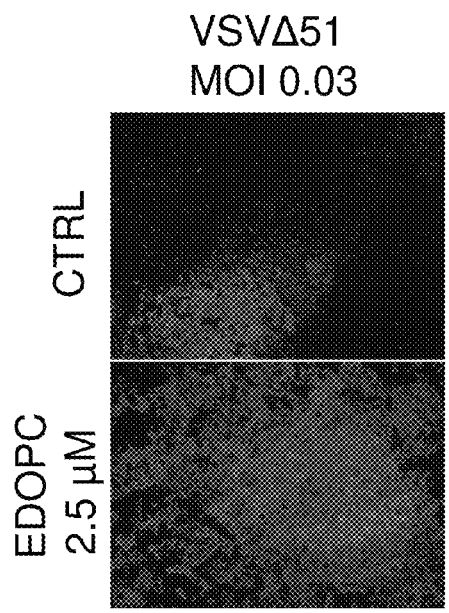
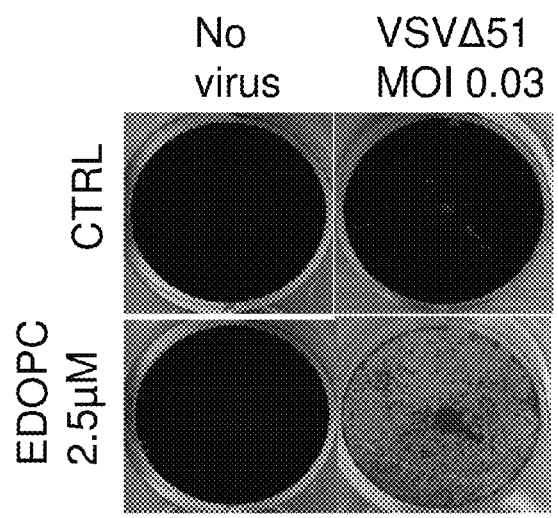

Figure 10G
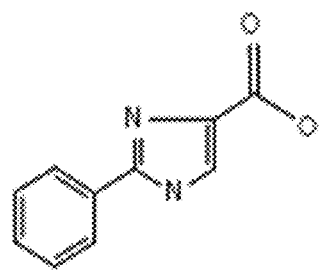
SB02118: 2-phenyl-1H-imidazole-4-carboxylic acid 1.5 hydrate(*PICA*)
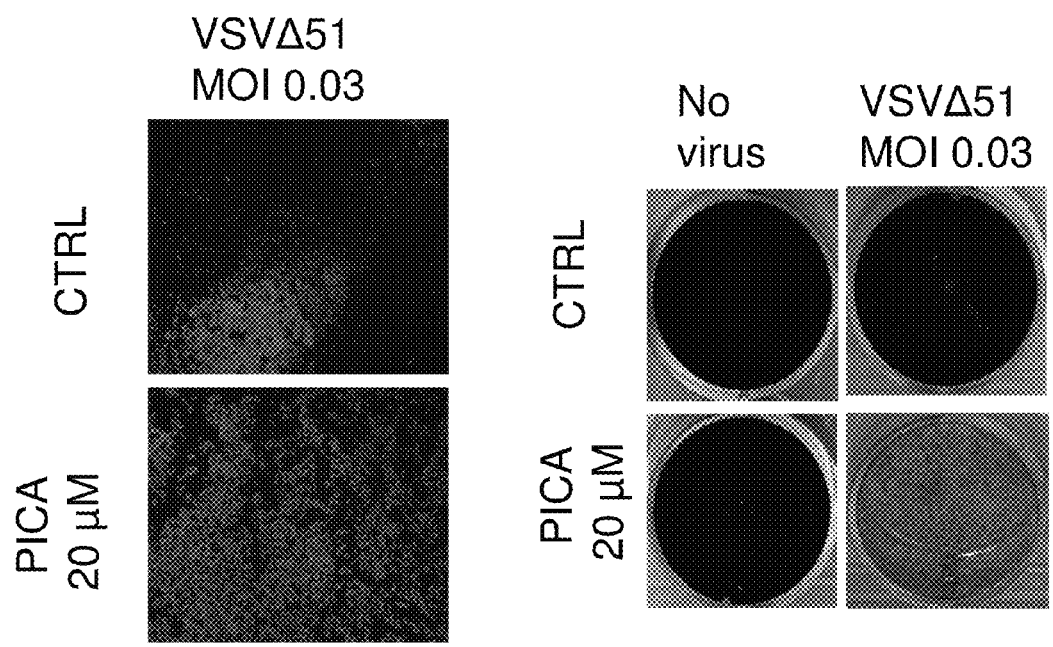

Figure 10H
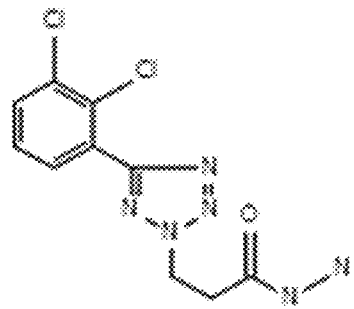
RJF 02208
RJF02208: 3-[5-(2,3-dichlorophenyl)-2H-1,2,3,4-tetraazol-2-yl]propanohydrazide (DCTP)
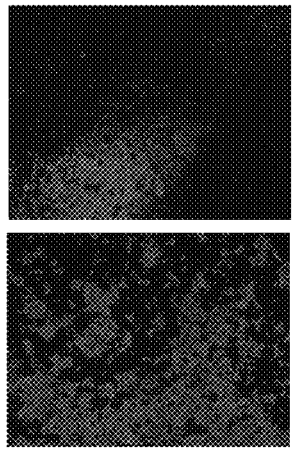
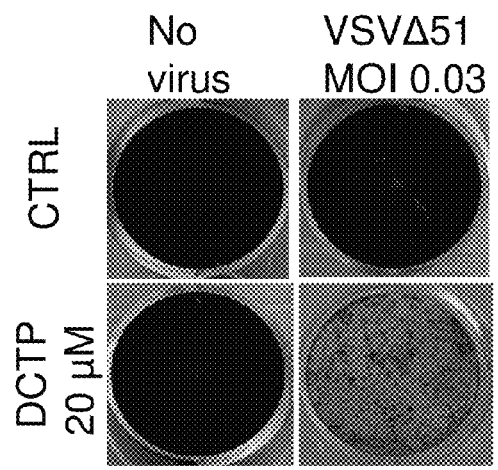

Figure 10I
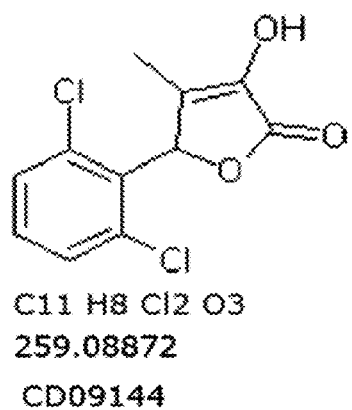
C11 H8 Cl2 O3
259.08872
CD09144
CD09144: 5-(2,6-dichlorophenyl)-3-hydroxy-4-methyl-2,5-dihydrofuran-2-one (*DHMDF*)
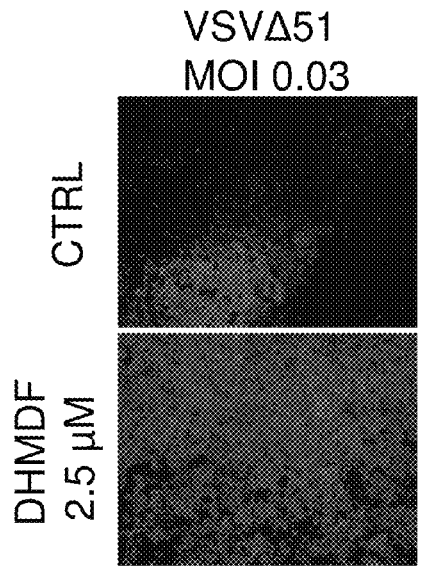
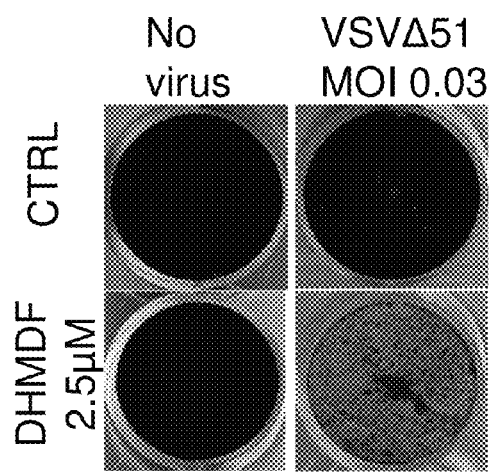

Figure 10J
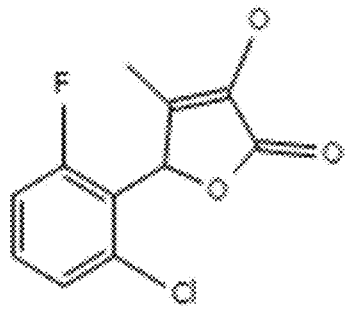
CD 08996
CD08996: 5-(2-chloro-6-fluorophenyl)-3-hydroxy-4-methyl-2,5-dihydrofuran-2-one (*CFHMDF*)
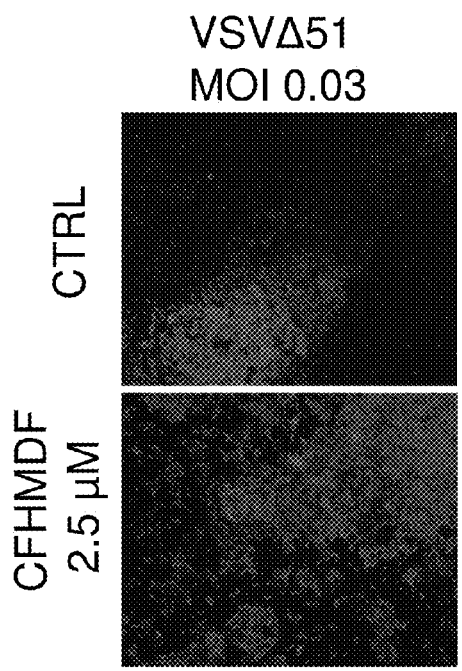
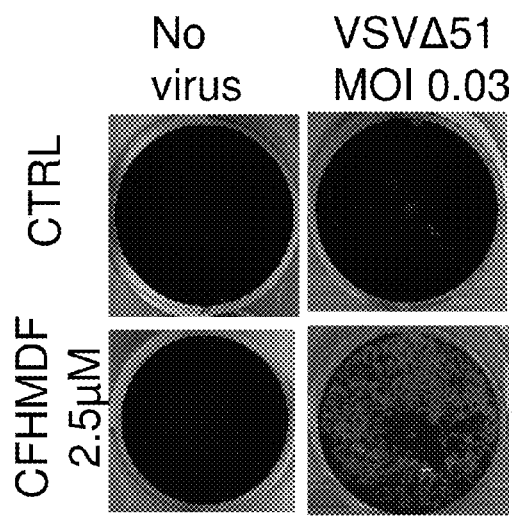

Figure 14A
Effect of VSe1 on VSVΔ51-Induced Gene Expression

- VSV
- VSV + VSe1

Figure 14B
Effect of SAHA on VSVΔ51-Induced Gene Expression

- VSV
- VSV + SAHA

Genes

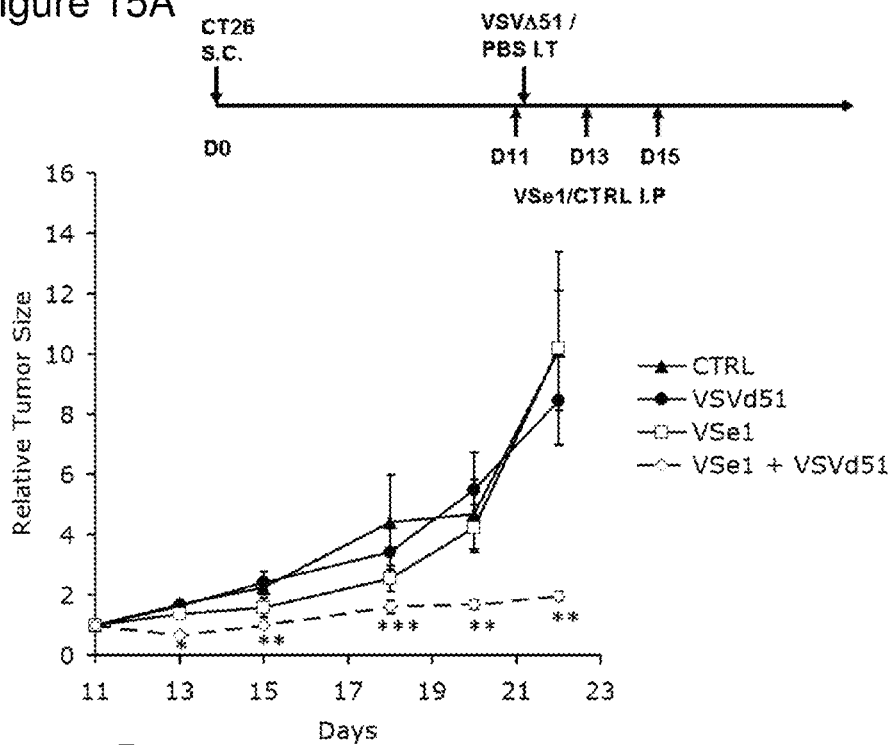
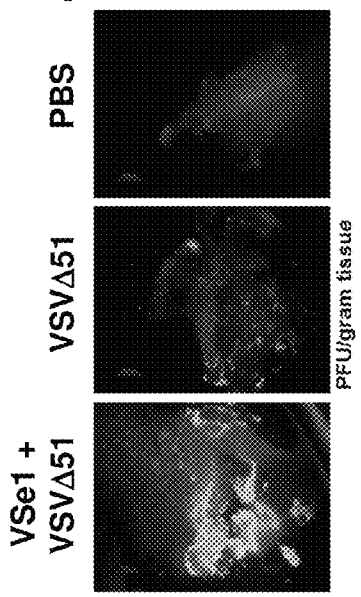
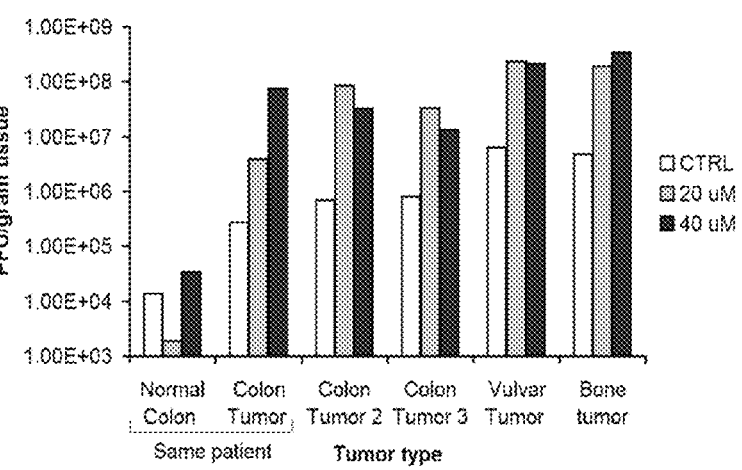

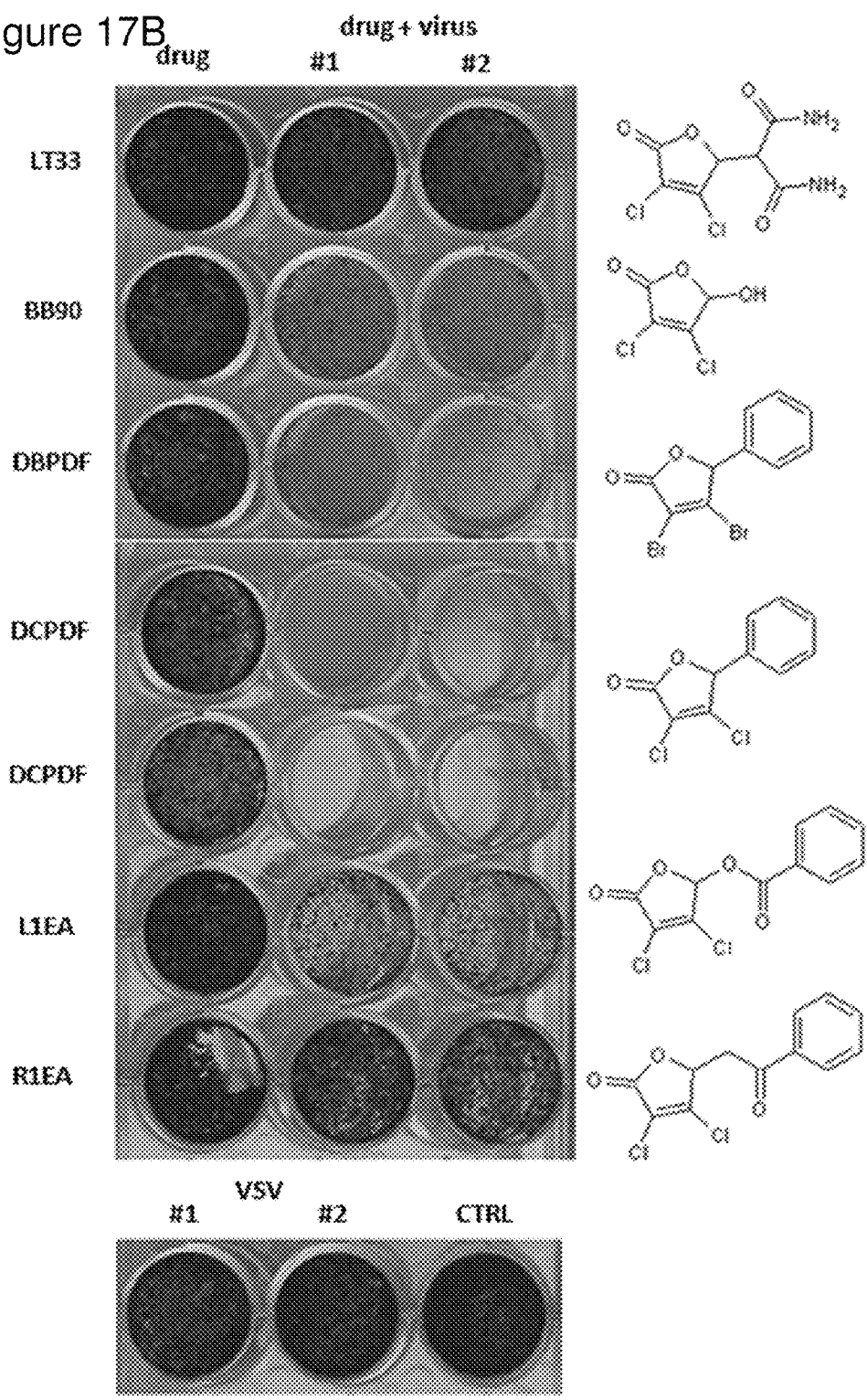

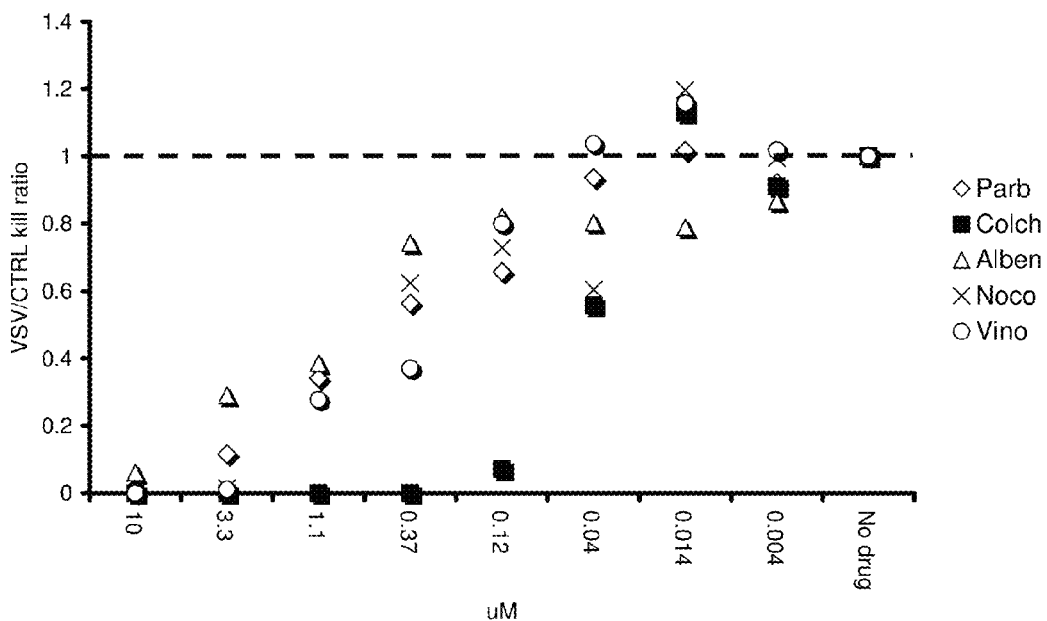
Figure 18A  4T1
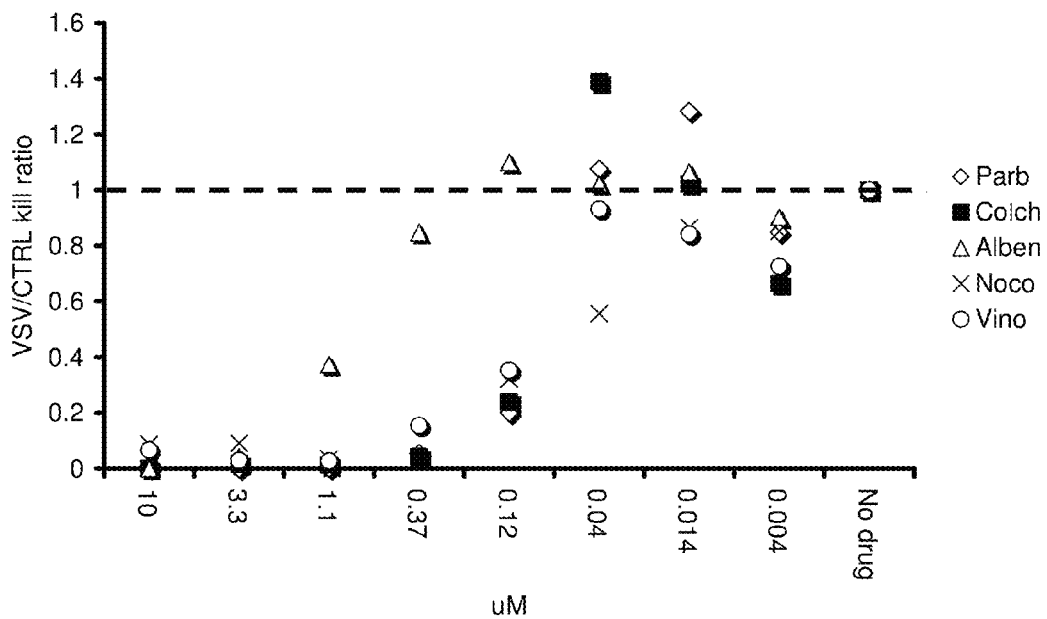
Figure 18B  CT26

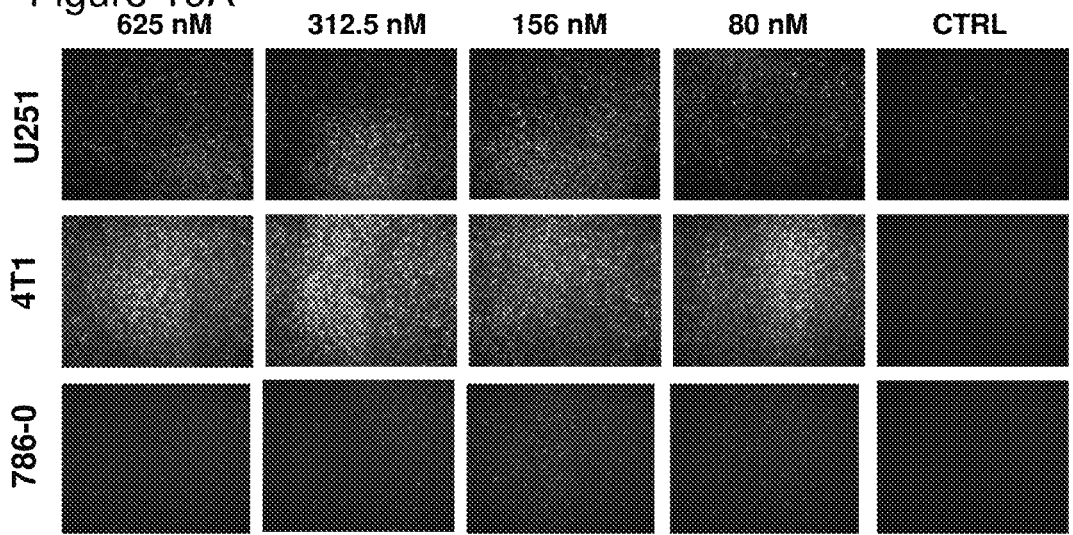
Figure 19A
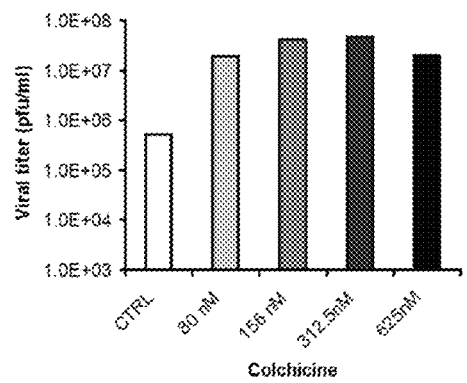
Figure 19B U251
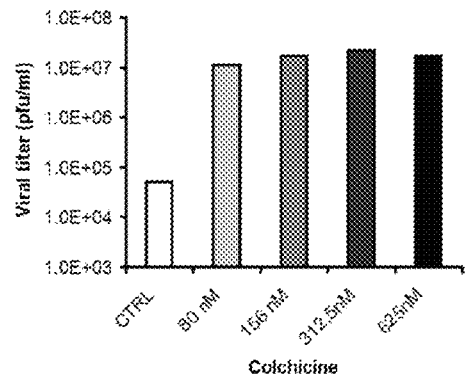
Figure 19C 4T1
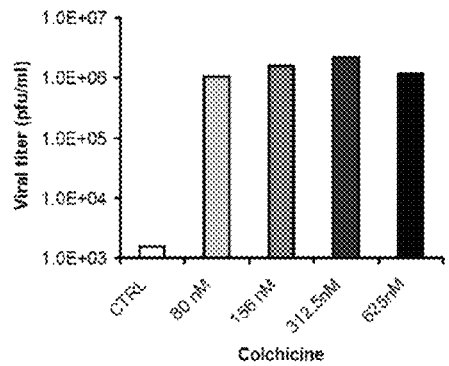
Figure 19D 786-0

Figure 21B
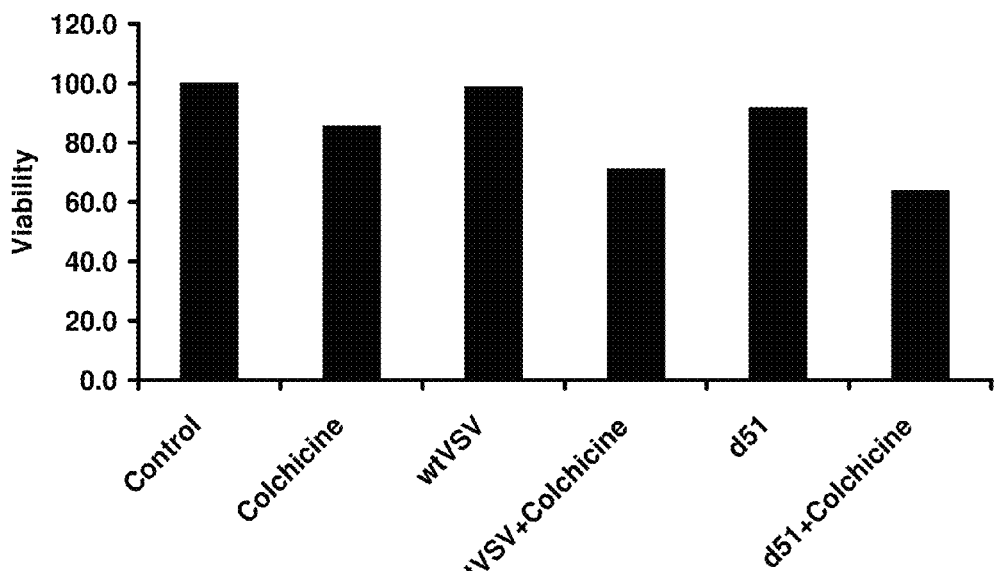
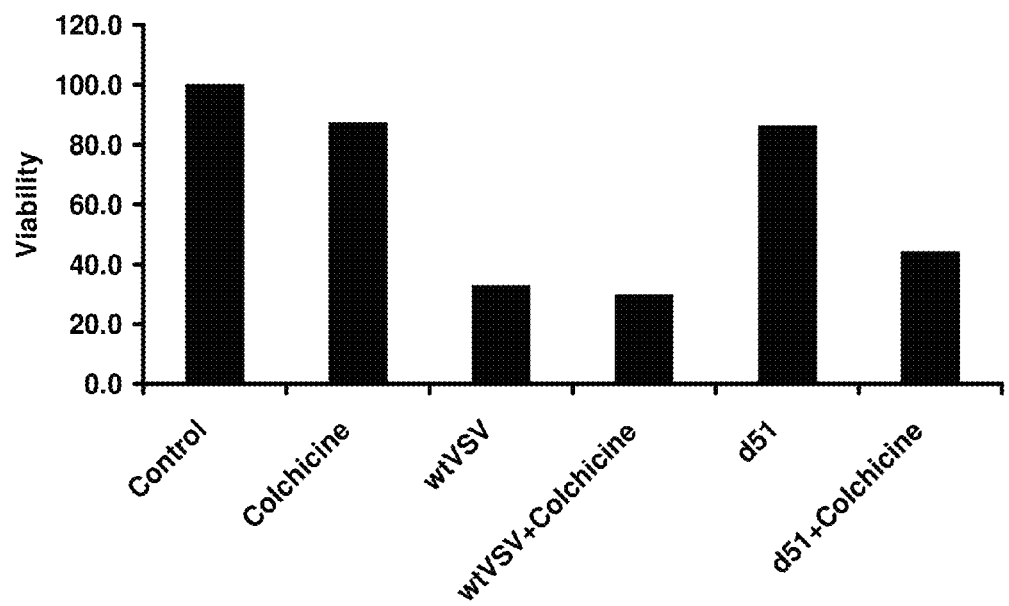

Figure 22

Effect of VSe on Vaccinia titers

[Bar chart: PFU/ml vs samples]
- CTRL: ~40000
- VSe-1: ~200000 (5)
- VSe-6: ~350000 (8.8)
- VSe-7: ~710000 (17.8)
- VSe-8: ~225000 (5.5)
- VSe-12: ~150000 (3.5)
- VSe-14: ~580000 (14.3)

Figure 23

Viral titers ($log_{10}TCID50/mL$) 48hrs P

| Drug | VSe | | VSe | | Viruse | VSe | |
|---|---|---|---|---|---|---|---|
| Viruse | FM | PR8 | FM | PR | | FM | PR |
| 20 uM | >8. | 6.7 | >8. | 7. | 1 uM | 8.2 | 5. |
| 15 uM | >8. | 6. | >8. | 6.2 | 0.5 uM | >8. | |
| 10 uM | >8. | | 8.2 | | 0.25 uM | >8. | |

| Virus CTR | rep | rep | rep |
|---|---|---|---|
| FM | 1.7 | | |
| PR | < | < | |

COMPOSITIONS AND METHODS FOR ENHANCING VIRUS EFFICACY

RELATED APPLICATIONS

The present application is a divisional of and claims priority under 35 U.S.C. §120 to U.S. patent application, U.S. Ser. No. 13/382,355, filed Feb. 2, 2012, which is a national stage filing under 35 U.S.C. §371 of international PCT application, PCT/CA2010/001057, filed Jul. 7, 2010, which claims priority under 35 U.S.C. §119(e) to U.S. provisional patent application, U.S. Ser. No. 61/270,345, filed Jul. 7, 2009, and claims priority under 35 U.S.C. §119(a) to Canadian application no. 2,689,707, filed Nov. 16, 2009, each of which is incorporated herein by reference.

FIELD OF INVENTION

The present invention relates to compounds that enhance viral growth, spread or cytotoxicity. More specifically, the present invention relates to compounds that enhance oncolytic viral efficacy and methods of using same.

BACKGROUND OF THE INVENTION

Oncolytic viruses (OV) are novel replicating therapeutics selected or designed to preferentially grow in and kill cancer cells. Diverse OV platforms have shown promise for the treatment of several types of cancers (1-5). Due to the self-replicating nature of OVs, the principle challenge in OV therapy is not initial saturation of all the tumors but rather efficient spreading within tumor cells upon infection of a reasonable amount of cancerous tissue. Much like most live vaccines, essentially all OVs have been genetically modified or selected for attenuated growth. While this limits the spread of OVs in normal host tissues, it can also blunt their natural ability to rapidly spread within and between tumors (6).

Vesicular stomatitis virus (VSV) is an OV that has shown outstanding efficacy in several in vivo cancer models (2, 3, 7). VSV is a small, enveloped, negative strand RNA rhabdovirus that is particularly sensitive to type I Interferons (IFN), a key component of normal innate cellular anti-viral immunity. In most cancers, IFN response pathways are defective and VSV can be extremely effective (2, 3). However, several cancers retain robust anti-viral defenses, rendering VSV much less effective when used alone (5, 8).

We have previously shown that histone deacetylase inhibitors (HDI) enhance the ability of VSV to infect and kill resistant tumor cells due in part to HDI-induced dampening of IFN mediated anti-viral response (9) and to enhanced apoptosis (10). Continual administration of HDIs prior to and following VSV administration in mice led to better spread of the virus preferentially within tumors and led to reduced tumor growth in the combination treatment as opposed to either treatment alone. Because continuous administration of HDIs can lead to various toxicities including cardiac toxicity in humans, it is desirable to identify other small molecules that could be used to enhance OV efficacy.

There is a need in the art to identify compounds and compositions that enhance virus growth, spread or cytotoxicity. There is also a need in the art to identify compounds and compositions that enhance oncolytic virus efficacy. Further, there is a need in the art to identify novel methods for treating cancer cells in vitro and in vivo.

SUMMARY OF THE INVENTION

The present invention relates to compounds that enhance viral growth, spread or cytotoxicity. More specifically, the present invention relates to compounds that enhance oncolytic viral efficacy and methods of using same.

According to the present invention there is provided a compound of formula (I)

an N-oxide, pharmaceutically acceptable addition salt, quarternary amine or stereochemically isomeric form thereof, wherein:

A is a 5-membered heterocylic ring comprising 1-4 heteroatoms selected from O, N or S and 1 or 2 double bonds;

$R^1$ is H, oxo, alkoxycarbonyl, hydrazinylcarbonylalkyl or amino;

$R^2$ is nothing, alkyl, halogen, carboxyl, heteroarylcarbonylamino or hydroxyl;

$R^3$ is nothing, H, alkyl, halogen or heterocyclylaminosulfonyl, and $R^4$ is H, alkyl, unsubstituted aryl or aryl substituted with 1-3 halogens.

According to a further embodiment, there is provided a compound as described above wherein A is $X_1$ is O, NH or S;

$R^1$ is H, oxo, alkoxycarbonyl, hydrazinylcarbonylalkyl or amino;

$R^2$ is nothing, alkyl, halogen, carboxyl, heteroarylcarbonylamino or hydroxyl;

$R^3$ is nothing, H, alkyl, halogen or heterocyclylaminosulfonyl, and $R^4$ is H, alkyl, unsubstituted aryl or aryl substituted with 1-3 halogens.

The present invention also provides a compound as described above represented by $$\begin{array}{c} R_3 \quad R_2 \\ X_4 = X_3 \\ \| \quad \| \\ X_5 \quad X_2 \\ R_4 \quad X_1 \quad R_1 \end{array} \quad \text{(II)}$$

wherein,
$X_1$ is O, N, NH or S;
$X_2$, $X_3$ and $X_4$ are independently C or N;
$X_5$ is C;
$R^1$ is H, oxo, alkoxycarbonyl, hydrazinylcarbonylalkyl or amino;
$R^2$ is nothing, alkyl, halogen, carboxyl, heteroarylcarbonylamino or hydroxyl;
$R^3$ is nothing, H, alkyl, halogen or heterocyclylaminosulfonyl;
$R^4$ is H, alkyl, unsubstituted aryl or aryl substituted with 1-3 halogens;
wherein the bond between the atoms $X_2$ and $X_3$ is a single or a double bond;
wherein the bond between the atoms $X_3$ and $X_4$ is a single or a double bond;
wherein the bond between the atoms $X_4$ and $X_5$ is a single or a double bond;
wherein the bond between the atoms $X_5$ and $X_1$ is a single or a double bond;
wherein when the bond between the atoms $X_2$ and $X_3$ and the bond between $X_4$ and $X_5$ are each single bonds, the bond between the atoms $X_3$ and $X_4$ is a double bond, the bond between the atoms $X_5$ and $X_1$ is a single bond, $X_2$ is C and $R^1$ is oxo; or
wherein when the bond between the atoms $X_2$ and $X_3$ and the bond between $X_4$ and $X_5$ are each single bonds, the bond between the atoms $X_3$ and $X_4$ is a double bond, the bond between the atoms $X_5$ and $X_1$ is a double bond and $X_1$ is N, or
wherein when the bond between the atoms $X_2$ and $X_3$ and the bond between $X_4$ and $X_5$ are each double bonds, the bond between the atoms $X_3$ and $X_4$ is a single bond and the bond between $X_5$ and $X_1$ is a single bond.

In a further embodiment, there is provided a compound as described above represented by $$\begin{array}{c} R_3 \quad R_2 \\ \diagup \quad \diagdown \\ R_4 \quad X_1 \quad O \end{array} \quad \text{(III)}$$

wherein:
$X_1$ is O, NH or S;
$R^2$ is alkyl, halogen, carboxyl or hydroxyl;
$R^3$ is alkyl or halogen, and
$R^4$ is alkyl, unsubstituted aryl or aryl substituted with 1-3 halogens.

Also provided is a compound as described above selected from the group consisting of 3,4-dichloro-5-phenyl-2,5-dihydrofuran-2-one, 2-phenyl-1H-imidazole-4-carboxylic acid 1.5 hydrate, 3-[5-(2,3-dichlorophenyl)-2H-1,2,3,4-tetraazol-2-yl]propanohydrazide, ethyl 3,5-dimethyl-4-{[(2-oxo-3-azepanyl)amino]sulfonyl}1H-pyrrole-2-carboxylate, 2-amino-5-phenyl-3-thiophenecarboxylic acid, methyl 3-[(quinolin-6-ylcarbonyl)amino]thiophene-2-carboxylate, 5-(2-chloro-6-fluorophenyl)-3-hydroxy-4-methyl-2,5-dihydrofuran-2-one, and 5-(2,6-dichlorophenyl)-3-hydroxy-4-methyl-2,5-dihydrofuran-2-one.

The present invention also provides a compound having formula $$\begin{array}{c} X \\ \| \\ R_5 \diagdown N \diagup \diagdown N \diagup R_6 \\ H \quad \quad H \end{array} \quad \text{(IV)}$$

wherein,
X is O or S;
$R_5$ is hydroxyalkyl, heteroaryl, unsubstituted aryl, aryl substituted with one or more substituents selected from the group consisting of alkyl and halogen, heterocyclyl or benzodioxylalkyl; and
$R_6$ is amino, aryl or aryl substituted with one or more substituents selected from the group consisting of alkyl and halogen.

Also provided is a compound as described above, wherein the compound is selected from N-(3,4-dimethylphenyl)-N'-(2-pyridyl)thiourea, N1-(2,6-diethylphenyl)hydrazine-1-carbothioamide, N-(2-hydroxyethyl)-N'-(2-methylphenyl)thiourea, N1-(2-chloro-6-methylphenyl)hydrazine-1-carbothioamide, and N-(4-chlorophenyl)-N'-(2,3-dihydro-1,4-benzodioxin-2-ylmethyl)urea.

The present invention also provides a compound as described above selected from the group consisting of 3,4-dichloro-5-phenyl-2,5-dihydrofuran-2-one, 2-phenyl-1H-imidazole-4-carboxylic acid 1.5 hydrate, 3-[5-(2,3-dichlorophenyl)-2H-1,2,3,4-tetraazol-2-yl]propanohydrazide, ethyl 3,5-dimethyl-4-{[(2-oxo-3-azepanyl)amino]sulfonyl}1H-pyrrole-2-carboxylate, 2-amino-5-phenyl-3-thiophenecarboxylic acid, methyl 3-[(quinolin-6-ylcarbonyl)amino]thiophene-2-carboxylate, 5-(2-chloro-6-fluorophenyl)-3-hydroxy-4-methyl-2,5-dihydrofuran-2-one, and 5-(2,6-dichlorophenyl)-3-hydroxy-4-mrthyl-2,5-dihydrofuran-2-one, N-(3,4-dimethylphenyl)-N'-(2-pyridyl)thiourea, N1-(2,6-diethylphenyl)hydrazine -1-carbothioamide, N-(2-hydroxyethyl)-N'-(2-methylphenyl)thiourea, N1-(2-chloro-6-methylphenyl)hydrazine-1-carbothioamide, N-(4-chlorophenyl)-N'-(2,3-dihydro-1,4-benzodioxin-2-ylmethyl)urea, 4-(benzyloxy)-2-methyl-1-nitrobenzene, 1-{4-[(2-methylquinolin-4-yl)amino]phenyl}ethan-1-one, N1-(1,2,3,10-tetramethoxy-9-oxo-5,6,7,9-tetrahydrobenzo[a] heptalen-7-yl)acetamide, methyl N-[4-(dimethylamino) benzylidene]aminomethanehydrazonothioate, methyl N-(4-chlorophenyl)-(dimethylamino)methanimidothioate hydroiodide, 4',5'-dihydro-4'-(5-methoxyphenyl)spiro[2H-1-benzothiopyran-3(4H)m3'-[3H]pyrazole]-4-one, 1H -benzo[d]imidazole-2-thiol, N-(2-furylmethylidene)-(4-{[(2-furylmethylidene)amino]methyl}cyclohexyl)methanamine; 2-[4-(diethoxymethyl)benzylidene]malononitrile; 2-(cyclopropylcarbonyl)-3-(3-phenoxy-2-thienyl)acrylonitrile; N'-(3,5-dichlorophenyl)-2,4-difluorobenzohydrazide; 10-(hydroxymethylene)phenanthren-9(10H)-one; N1-(2,5-difluorophenyl)-4-({[4-(trifluoromethyl)phenyl] sulfonyl}amino)benzene-1-sulfonamide; N-[4-(4-chlorophenyl)-2,5-dioxopiperazino]-2-(2,3-dihydro-1H-indol-1-yl)acetamide, 4-{[(4-{[(3-carboxyacryloyl)amino] methyl}cyclohexyl)methyl]amino}-4-oxo-2-butenoic acid; 5-oxo-3-phenyl-5-{4-[3-(trifluoromethyl)-1H-pyrazol-1-yl] anilino}pentanoic acid, N1-(4-chlorophenyl)-2-({4-methyl- 5-[1-methyl-2-(methylthio)-1H-imidazol-5-yl]-4H-1,2,4-triazol-3-yl}thio)acetamide, 6-[2-(4-methylphenyl)-2-oxoethyl]-3-phenyl-2,5-dihydro-1,2,4-triazin-5-one; N1-[2-(tert-butyl)-7-methyl-5-(trifluoromethyl)pyrazolo[1,5-a]pyrimidin-3-yl]acetamide; 4-(2,3-dihydro-1H-inden-5-yl)-6-(trifluoromethyl)pyrimidin-2-amine; ethyl 1-(2,3-dihydro-1-benzofuran-5-ylsulfonyl)-4-piperidinecarboxylate, 2,3-diphenylcycloprop-2-en-1-one, 1-cyclododecyl-1H-pyrrole-2,5-dione, 1-(4-methylphenyl)-2,5-dihydro-1H-pyrrole-2,5-dione, 2-[(4-phenoxyanilino)methyl]isoindoline-1,3-dione, 2-{[1-(3-chloro-4-methylphenyl)-2,5-dioxotetrahydro-1H-pyrrol-3-yl]thio}benzoic acid, 1-(1,3-benzodioxol-5-ylmethyl)-2,5-dihydro-1H-pyrrole-2,5-dione, 4-chloro-N-[3-chloro-2-(isopropylthio)phenyl]benzamide, and N-({5-[({2-[(2-furylmethyl)thio]ethyl}amino)sulfonyl]-2-thienyl}methyl)benzamide. In a preferred embodiment, the compound is 3,4-dichloro-5-phenyl-2,5-dihydrofuran-2-one (DCPDF).

The present invention also provides a composition comprising the compound as described above, and a pharmaceutically acceptable carrier, diluent or excipient.

Also, the present invention provides a composition comprising the compound as described above and one or more of a) a virus, preferably an attenuated virus, a genetically modified virus or an oncolytic virus; b) one or more cancer cells; c) a carrier, diluent or excipient; d) a pharmaceutically acceptable carrier, diluent or excipient; e) non-cancer cells; f) cell culture media; g) one or more cancer therapeutics; or any combination of a)-g).

In a particular embodiment, which is not meant to be limiting in any manner, there is provided a compound as described above and a medium for growing, culturing or infecting cells with a virus and optionally, one or more cells which are capable of being infected by the virus. In a further embodiment, the cells are immortalized cells, cancer cells or tumor cells. In an alternate embodiment, the cells are MDCK, HEK293, Vero, HeLa or PER.C6 cells.

Also provided is a kit comprising the compound as described above and a) a virus, preferably an attenuated or genetically modified virus or an oncolytic virus; b) one or more cancer cells; c) a pharmaceutically acceptable carrier, diluent or excipient; d) non-cancer cells; e) cell culture media; f) one or more cancer therapeutics, g) a cell culture plate or multi-well dish; h) an apparatus to deliver the viral sensitizing compound to a cell, medium or to a subject; i) instructions for using the viral sensitizing agent; j) a carrier diluent or excipient, or any combination of a)-j).

In a particular embodiment, which is not meant to be limiting in any manner, there is provided a kit comprising a compound as described above and a medium for growing, culturing or infecting cells with a virus and optionally, one or more cells which are capable of being infected by the virus. The kit may also comprise instructions for using any component or combination of components and/or practicing any method as described herein.

The present invention also provides a method of enhancing the spread of a virus in cells comprising, administering the compound as described above to the cells prior to, after or concurrently with the virus. The method is preferably practiced in vitro.

The present invention also provides a method of enhancing the spread of an attenuated virus or a genetically modified virus in cells comprising, administering the compound as described above to the cells prior to, after or concurrently with the attenuated or genetically modified virus.

The present invention also provides a method of enhancing the spread of an oncolytic virus in tumor or cancer cells comprising, administering the compound as described above to the cancer or tumor cells prior to, after or concurrently with the oncolytic virus. The cancer or tumor cells may be in vivo, or in vitro, preferably in vivo from a mammalian subject such as, but not limited to, a human subject.

Also provided is a method of increasing the oncolytic activity of an oncolytic virus in cancer or tumor cells comprising, administering the compound as described above to the cancer or tumor cells prior to, concurrently with or after the oncolytic virus. The cancer or tumor cells may be in vivo, or in vitro, preferably from a mammalian subject such as, but not limited to a human subject.

The present invention also contemplates a method of producing a virus by growing the virus in an appropriate medium in the presence of the compound as described above.

The present invention also contemplates a method of producing an attenuated virus by growing the virus in an appropriate medium in the presence of the compound as described above.

The present invention also contemplates a method of producing a genetically modified virus by growing the virus in an appropriate medium in the presence of the compound as described above.

The present invention also contemplates a method of producing an oncolytic virus by growing the virus in an appropriate medium in the presence of the compound as described above.

This summary of the invention does not necessarily describe all features of the invention.

BRIEF DESCRIPTION OF THE DRAWINGS

These and other features of the invention will become more apparent from the following description in which reference is made to the appended drawing wherein:

FIG. 1 shows results of the effect of 3,4 Dichloro-5-Phenyl-2,5-Dihydrofuranone (DCPDF) on VSVΔ51 spread in CT26 colon cancer cells. CT26 cells were pre-incubated with varying doses of DCPDF for 4 hours and then challenged with a multiplicity of infection (MOI) of 0.03 of RFP-expressing VSVΔ51. Fluorescence pictures were taken 42 hours post-infection.

FIGS. 5A to 5C show the effect of 3,4 Dichloro-5-Phenyl-2,5-Dihydrofuranone (DCPDF) on VSV spread in various cell lines. FIG. 5A shows confluent cells pretreated with DCPDF (at indicated concentrations) for 4 hours then challenged with RFP-expressing VSV at low MOI (0.03 for 786-0 and GM38, 0.01 for 4T1 and CT26 and U251). VSV spread was enhanced in all cancer cell lines but not in normal GM38 cells. FIG. 5B shows results that 3,4 Dichloro-5-Phenyl-2,5-Dihydrofuranone (DCPDF) increases VSV titers in various cancer cell lines but not normal cells. Confluent cells were pretreated with DCPDF (at indicated concentrations) for 4 hours then challenged with RFP-expressing VSV at low MOI (0.01 for 786-0, 4T1 and CT26 and 0.03 for GM38). Supernatants were collected after 48 h incubation and titered on Vero cells. Note that VSV spread was enhanced in cancer cell lines but not in normal GM38 cells. FIG. 5C shows results suggesting that the effect of DCPDF is dose dependent. Cells were treated using increasing concentrations of DCPDF. Supernatants were collected 48 h following infection with VSV at the indicated MOI.

FIG. 6A shows 4T1 and CT-26 cells treated with serial dilutions of a fixed ratio combination mixture of VSVΔ51 and VSe1 (500 PFU: 1 μM VSVΔ51:VSe1). Cytotoxicity was assessed using alamar blue reagent after 48 h. Combination indices (CI) were calculated according to the method of Chou and Talalay using Calcusyn. Plots represent the algebraic estimate of the CI in function of the fraction of cells affected (Fa). Error bars indicate the estimate standard error. FIG. 6B shows 4T1 cells challenged with an MOI of 0.01 of VSVΔ51 or no virus following a 4-hour pretreatment with increasing doses of DCPDF. 48 hours later cells were fixed and stained using coomassie blue.

FIGS. 7A to 7B show results suggesting DCPDF enhances spread of oncolytic vaccinia virus. FIG. 7A shows murine 4T1 breast cancer and B16-F10 melanoma cells pretreated for 4 hours with VSe1 20 μM then challenged with a cherry fluorescent protein-expressing oncolytic vaccinia virus (VVdd). Fluorescence pictures were taken 72 hours post-infection. FIG. 7B shows cells and supernatant subsequently collected and titered on U20S cells by standard plaque assay.

FIG. 8A shows B16 melanoma cells treated with DCPDF or HDAC inhibitor TSA over 48 hours. Cells were subsequently fixed, stained using propidium iodine and analyzed by flow cytometry. Cell cycle analysis was done using modfit. FIG. 8B shows the percentage of cells in each phase of the cell cycle according to data presented in FIG. 8A. Ap=apoptotic.

FIGS. 10A to 10J show results of 4T1 cells pre-treated for 2 hours with selected drugs identified from a screen of more than 13500 compounds. Cells were then challenged with RFP-expressing VSVΔ51 at indicated MOI (0.03 to 0.003). 48 hours later, fluorescence pictures were taken and coomassie stains were performed.

FIG. 11A shows a dot plot representation of the additional high throughput screening data. The y-axis corresponds to the parameter Log(VSV/CTRL) is defined as the logarithm of the cytotoxicity of compounds in presence of VSV over cytotoxicity of compounds in absence of VSV. The average of assay duplicates is plotted for each compound. The x-axis represents each of the 12280 compounds tested. Compounds exhibiting Log(VSV/CTRL) values above 0.3 were considered as potential viral sensitizers (shaded area). FIG. 11B shows that the potential viral sensitizers identified were re-tested in a 96-well plate format for VSVΔ51-enhancing activity on 4T1 cells using 10 μM concentrations of drug and a VSVΔ51 MOI of 0.03. A VSVΔ51 strain expressing RFP was used to visualize virus spread after 24 hours using fluorescence microscopy. SAHA (10 μM) was used as a positive control. FIG. 11C shows fold change in viral titers form supernatants collected from FIG. 11B after 48 hour incubation relative to vehicle-treated control. Arrow points to inset panel showing the molecular structure of VSe1 (3,4-dichloro-5-phenyl-2,5-dihydrofuran-2-one or DCPDF). The specific identity of compounds tested under the VSe nomenclature may be obtained from Table 2 herein.

FIG. 12A shows VSVΔ51 titers determined by plaque assay on Vero cells from supernatants collected at 40 hours post infection (VSVΔ51, MOI of 0.01) of 4T1, CT26, and 786-0 cells treated with either vehicle control, 20 or 40 μM VSe1. Data represents average from three to four independent experiments *p=0.007, **p=0.04, #p=0.02, ##p=0.01, $p=0.07, $$p=0.05 (ANOVA). Error bars represent the standard error. FIG. 12B shows CT26 cells treated with VSe1 20 μM or vehicle control then challenged with a wild type VSV (MOI=0.0003). Viral titers were assessed by plaque assay on Vero cells from supernatants collected at 18, 28 and 36 hours post infection. FIG. 12C shows results that various doses of DCPDF enhances viral titers from 786-0 and CT26 cells.

FIGS. 14A to 14B show results that VSe1 represses VSVΔ51-induced genes. CT26 cells were pre-treated with either SAHA 5 μM, VSe1 20 μM, or vehicle for 4 hours then challenged with VSVΔ51 at an MOI of 0.03 (or mock treated). 24 hours post-infection, cells were harvested and RNA was extracted. RNA was subsequently processed for hybridization on Affymetrix Mouse Gene 1.0 ST arrays. Expression of genes was normalized to values obtained for vehicle-treated, mock-infected control. In FIGS. 14A to 14B points along the x-axis represent each gene increased by over 2-fold by VSVΔ51 infection and are indicated by ●. In FIG. 14A fold change in gene expression of genes induced by VSVΔ51 in presence of VSe1 20 μM are indicated by ○. FIG. 14B shows that fold change in gene expression of genes induced by VSVΔ51 in presence of SAHA 5 μM are indicated by ○.

FIGS. 15A to 15C show results that VSe1 exhibits VSVΔ51-sensitizing activity in immuno-competent mice and in human clinical samples. FIG. 15A shows $3 \times 10^5$ VSVΔ51-resistant CT26 cells implanted subcutaneously (s.c) in syngeneic Balb/C mice 11 days prior to first treatment. On day 11 (D11) VSe1 (or vehicle) was administered intraperitoneally (i.p) at 0.4 mg/mouse. Four hours later, $1 \times 10^8$ VSVΔ51 (or PBS) was administered intra-tumorally (i.t). Two more doses of VSe1 were administered on days 13 and 15. Mouse tumor volume was measured using caliper and average tumor volumes relative to D11 are shown. Error bars represent standard error *p<0.005, p<0.05, *p<0.1 (ANOVA). N=5 mice per group. FIG. 15B shows false-color (LUT) fluorescence microscopy images of representative human colon tumor slices infected with $1\times10^7$ PFU of GFP-expressing VSVΔ51 (or PBS, top panel) 24 hours post treatment with either vehicle (middle panel) or 40 μM VSe1. Pictures were taken after 72 h incubation. FIG. 15C shows tumor or normal tissue slices treated as in FIG. 15B with either 20 or 40 μM VSe1. 72 h later tissue samples were collected and homogenized for subsequent tittering on Vero cells by plaque assay.

FIGS. 17A to 17E show results suggesting DCPDF (VSe1) and analogues thereof enhance VSVΔ51 spread in cells. 4T1 mouse breast cancer cells were pre-treated with either 20 μM drug or control four hours prior to infection with GFP-expressing VSVΔ51 at an MOI of 0.01. The experiment was done in duplicates and twice for the parent compound. Fluorescent pictures were taken approximately 48 hrs after the virus infection and are shown in FIG. 17A. Subsequently, a coomassie blue assay was used to determine cytotoxicity in FIG. 17B. Supernatants were also collected and virus particles titered on Vero cells using standard plaque assays (FIG. 17C). Data represents average from three independent experiments, *p=$9.39\times10^{-4}$, p=$6.7\times10^{-4}$, *p=0.14, #p=0.74, ##p=0.34, ###p=0.60 (unpaired, unequal variance T-test). The standard error is represented by the error bars. FIG. 17D shows cytotoxicity for each drug at varying concentrations on 4T1 cells. FIG. 17E shows DCPDF and the dibromine substituent DBPDF cytotoxicity at high concentrations on 4T1 cells. Cell viability was measured using Alamar Blue® reagent 48 hours after being subjected to 20μ M drug dose. The cell viabilities were normalized relative to control wells. The values are averages from three separate experiments done in duplicates, *p=$9.97\times10^{-3}$, p=$3.75\times10^{-5}$, *p=$4.58\times10^{-6}$, #p=$1.79\times10^{-2}$, ##p=$4.24\times10^{-5}$ (unpaired, unequal variance T-test). The standard errors are represented by the error bars.

FIGS. 18A to 18B show results that several microtubule destabilizing agents enhance VSV-induced cytotoxicity. 4T1 (FIG. 18A) and CT26 (FIG. 18B) cells were pretreated 4 h with microtubule destabilizing agents including parbendazole (Parb), colchicine (Colch), Albendazole (alben), Nocodazole (Noco), Vinorelbine base (Vino) at indicated concentrations. Cytotoxicity of the drugs in presence and absence of VSVΔ51 was determined and used to calculate the VSV/CTRL kill ratio which is equal to cell viability in presence of drug relative to VSV only control divided by the cytotoxicity of drug relative to the uninfected control. Values below one (dashed line) indicate that the drug had more effect then expected in presence of VSV at the given concentration.

FIGS. 19A to 19D show results that colchicine is a potent enhancer of VSVΔ51 spread in tumor cells. FIG. 19A shows human U251, 786-0 and mouse 4T1 cells were infected with VSVΔ51 expressing green fluorescent protein (GFP) at an MOI of 0.01 following pre-treatment with decreasing doses of colchicine. Fluorescence microscopy pictures were taken after 48 hours incubation. Strong enhancement of VSVΔ51 (GFP) spread is observed at dose as low as 80 nM. In FIGS. 19B to 19D supernatants were collected at 48 hours and used to assess viral titers using standard plaque assays. Colchicine could potently enhance virus production up to nearly 1000-fold.

In FIG. 21A, a variety of mouse and human cancer cells, as well as normal human MRC-5 cells were pre-treated with colchicine or control then challenged with wild type VSV (wtVSV) or VSVΔ51 expressing green fluorescent protein (GFP). Fluorescence microscopy pictures were taken 48 hours post-infection. Colchicine enhanced spread of VSVΔ51 but appeared to decrease the number of GFP positive cells using wtVSV. In FIG. 21B there are shown results suggesting the decrease in GFP-positive cells is likely due to enhanced killing of wtVSV-infected cells. Also note that the enhancement VSVΔ51 spread in FIG. 21A was not observed in normal MRC-5 cells, suggesting that the selectivity of VSVΔ51 towards tumor cells is maintained in presence of the microtubule destabilizing agent.

FIG. 22 shows results that several VSe compounds can increase the replication of vaccinia virus. 4T1 cells were infected with vaccinia virus at an MOI of 0.1 following pre-treatment with 10 μM of each VSe compound and incubated for 48 h (refer to VSe code in Table 2 for associated structures). Viral titers were assessed by standard plaque assay on U20S cells. Numbers above histogram indicate the fold change increase in viral titers relative to the control.

FIG. 23 shows results that VSe1, 6 and 7 can enhance production of two Influenza vaccine strains in MDCK manufacturing cells. Confluent MDCK cells were pre-treated for 4 hours with drug at indicated concentrations then challenged with a low MOI (0.001) of Influenza H1N1 vaccine strains FM/1/47 and PR8. Notably, the PR8 strain is used by the WHO and vaccine manufacturers to produce reassortant viruses containing the hemaglutinin (H) and Neuraminidase (N) genes from seasonal influenza strains. Supernatants were collected 48 hours post-infection and TCID50 were assessed by neutral red assay. In this experiment, increase in viral titers between 3 and 6 orders of magnitude were observed using the VSe compounds suggesting these can be useful in a vaccine manufacturing context.

DETAILED DESCRIPTION

Figure 2:
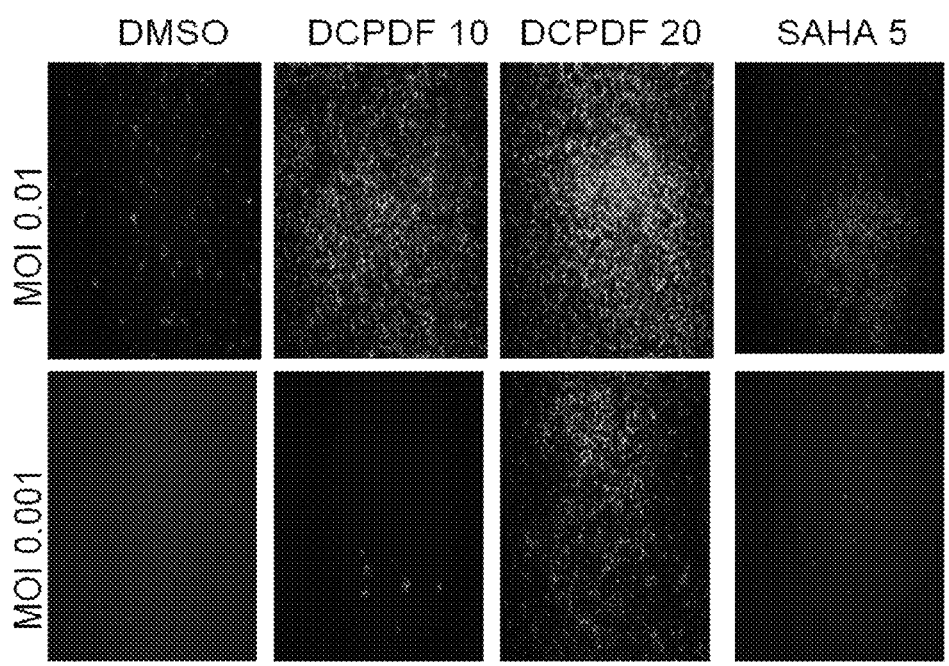
FIG. 2 shows results of the effect of DCPDF on VSVΔ51 spread in 4T1 breast cancer cells. 4T1 cells were pre-incubated with varying doses of DCPDF for 4 hours and then challenged with a multiplicity of infection of 0.01 or 0.001 of RFP-expressing VSVΔ51. Fluorescence pictures were taken 42 hours post-infection. SAHA used at 5 µM was also used as a positive control.
Figure 3:
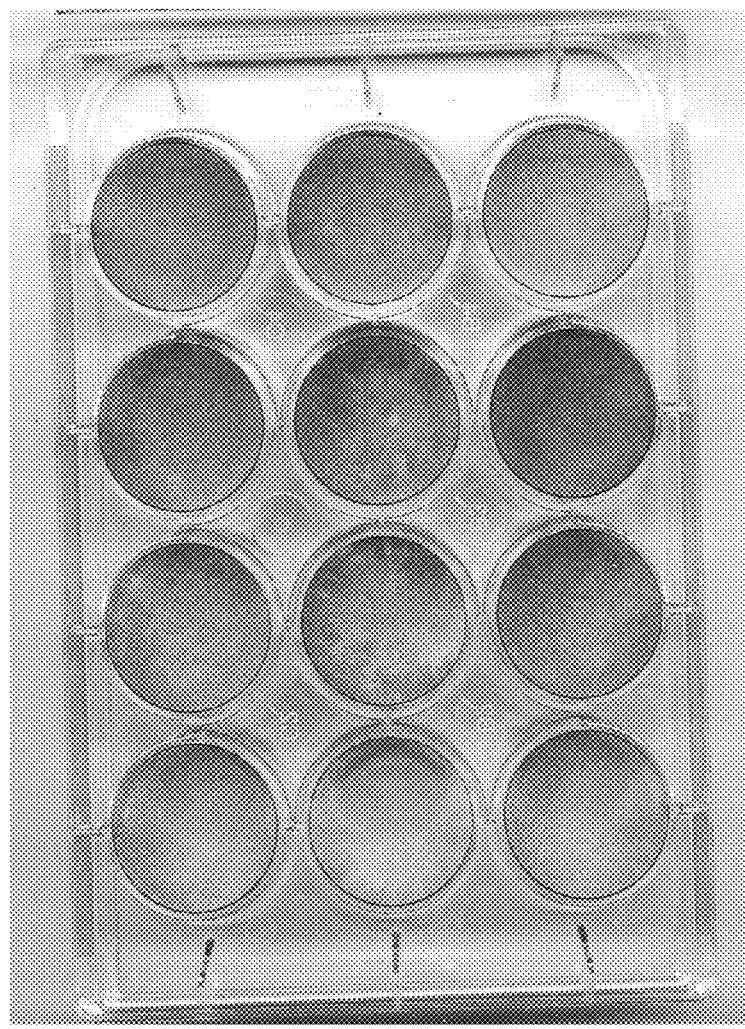
FIG. 3 shows results of the effect of DCPDF on VSVΔ51 induced cytotoxicity in 4T1 breast cancer cells. 4T1 breast cancer cells were preincubated with varying doses of DCPDF for 4 hours and then challenged with a MOI of 0.01 or 0.001 of VSVΔ51. Plates were stained using coomassie blue after 48 hours of incubation. SAHA used at 5 µM was also used as a positive control.
Figure 4:
FIG. 4 shows results that DCPDF enhances VSV output from CT26 cells. CT26 cells were infected at a MOI of 0.03 four hours following addition of DCPDF at increasing concentration. 48 hours later, supernatants were collected and titered on Vero Cells. Y axis denotes plaque forming units per ml (PFU/mL) and is on a log scale. VSV titers increase by nearly 3 logs (1000-fold) at the highest concentration of DCPDF.
Figure 5B:
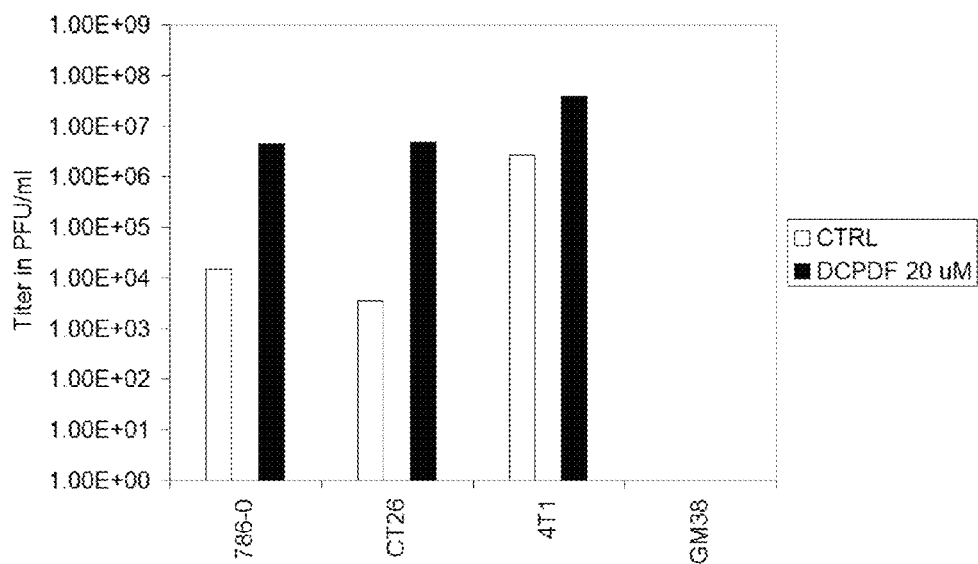
Figure 5C:
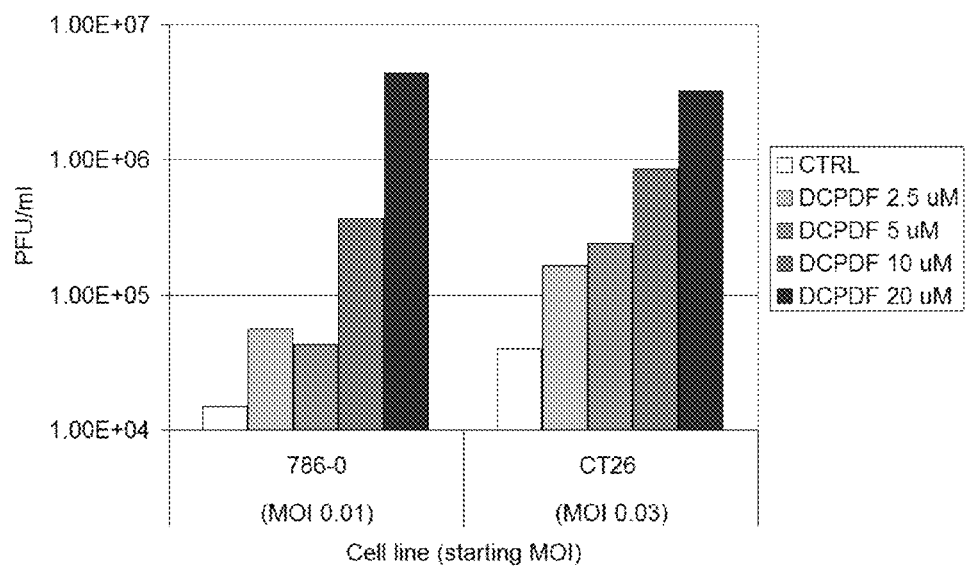
Figure 6A:
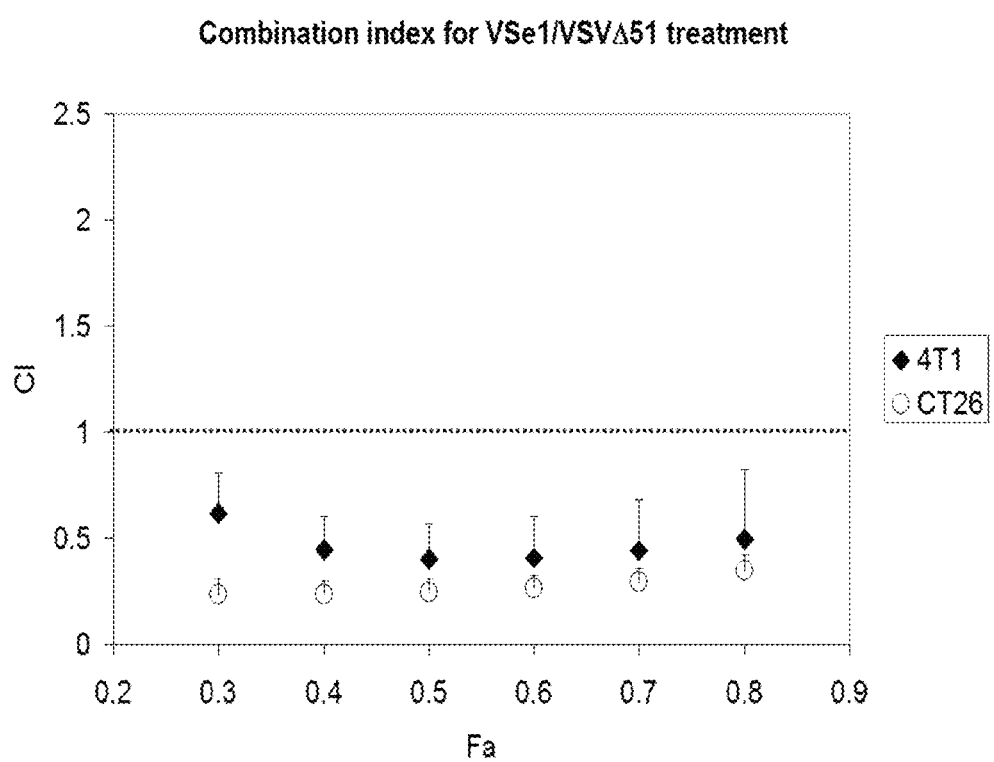
FIGS. 6A to 6B show results indicating that VSV and DCPDF induces synergistic cell killing in vitro.
Figure 6B:
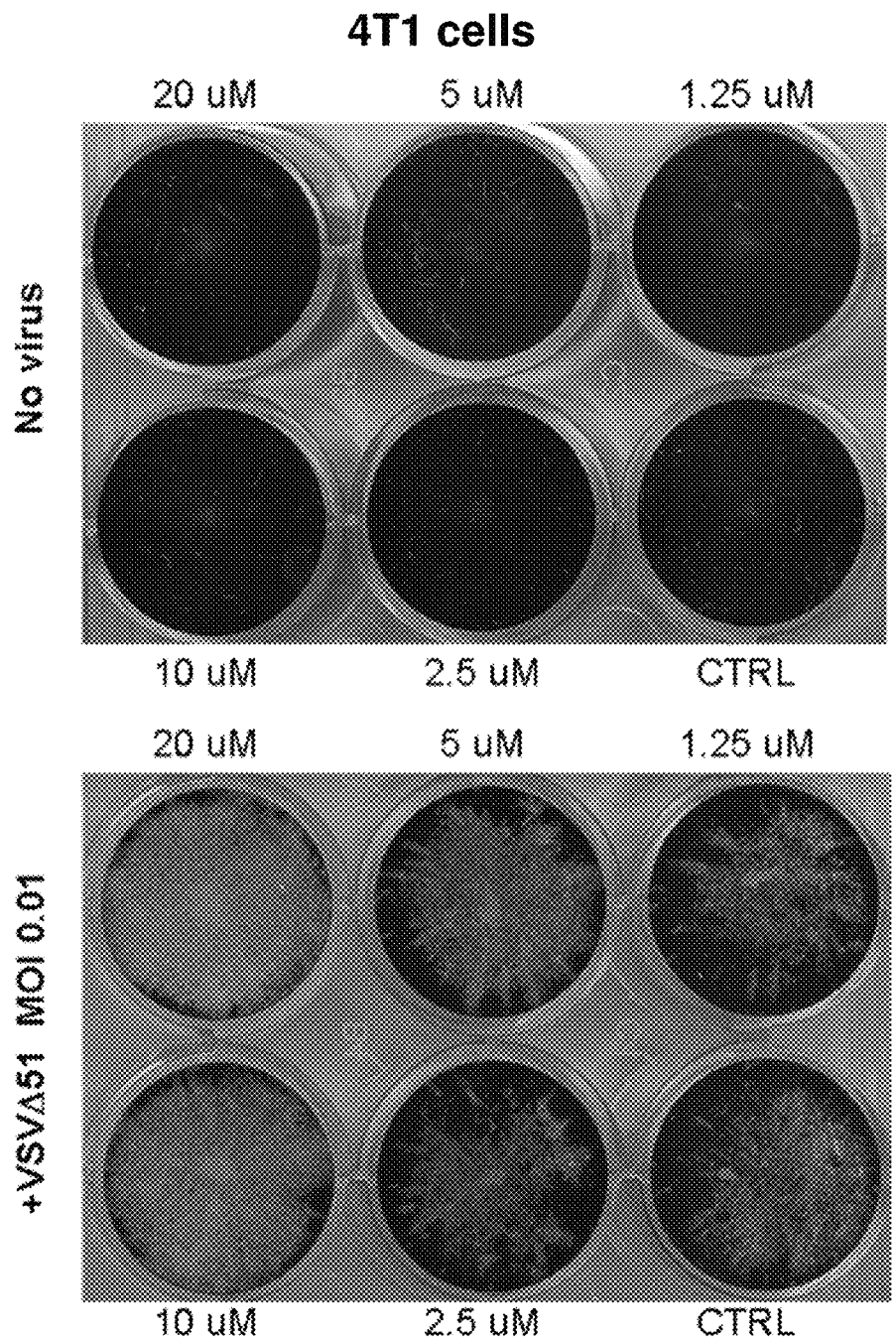
Figure 8A:
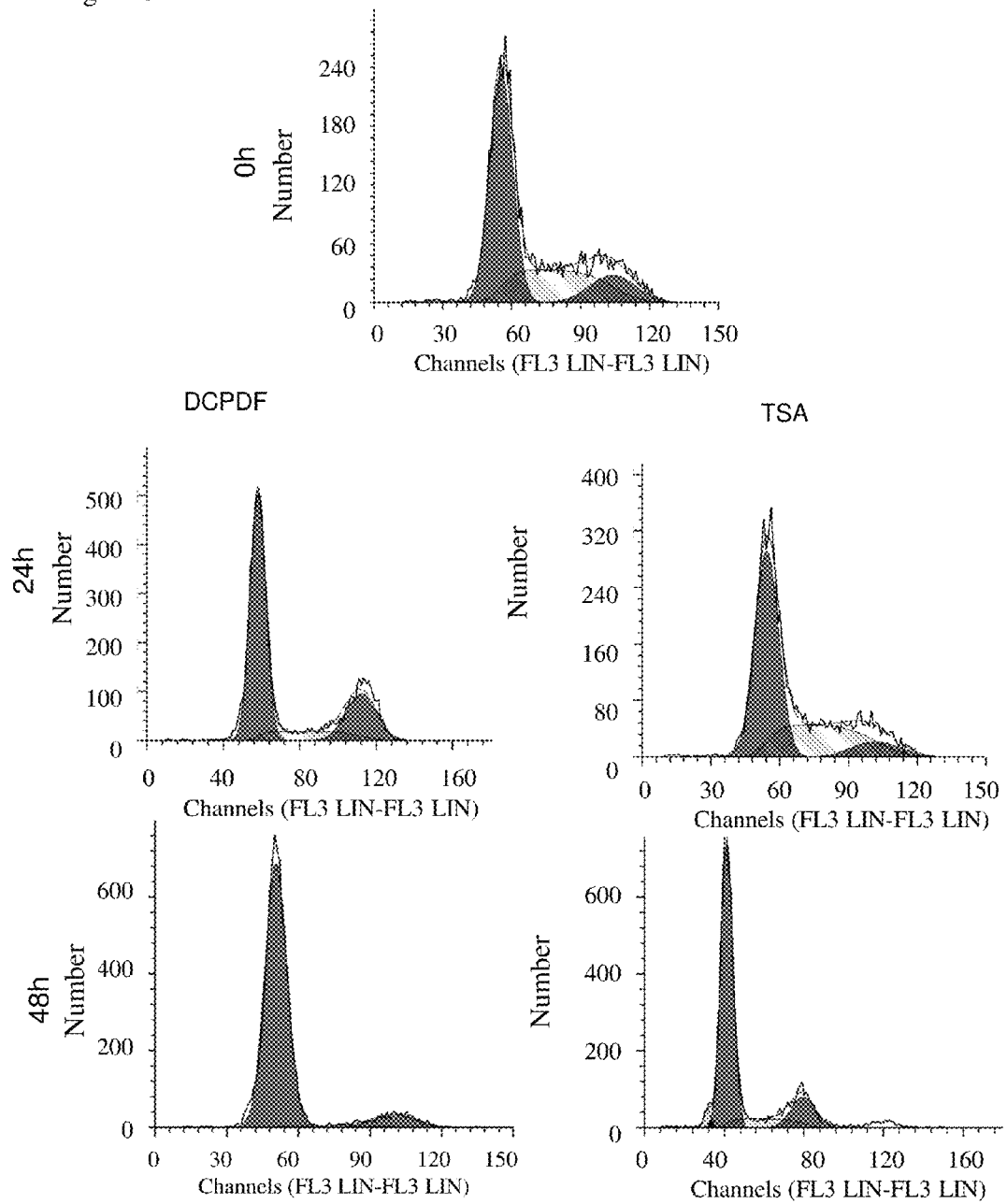
FIGS. 8A to 8B show results that DCPDF treatment leads to changes in the cell cycle distribution and block in G1.
Figures 8B, 9:
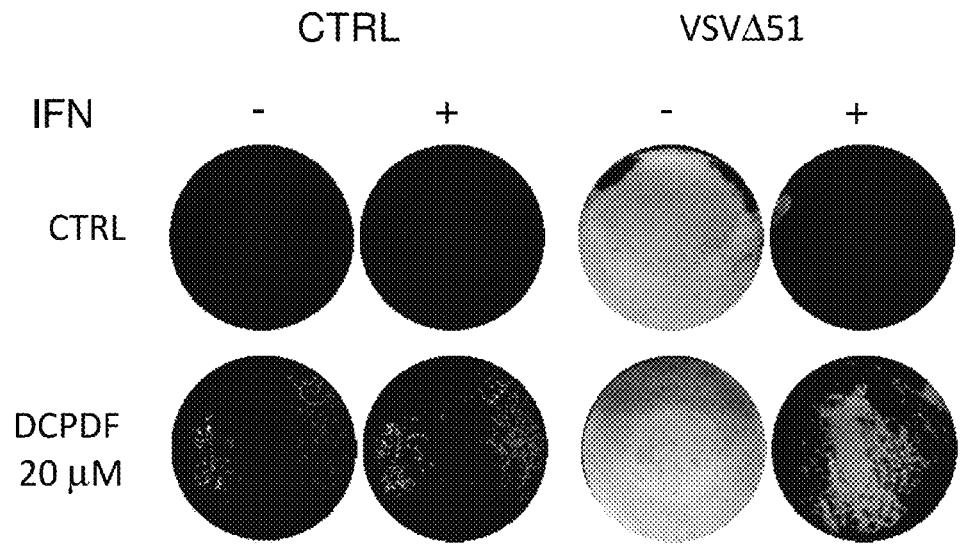
FIG. 9 shows results that DCPDF can overcome pre-existing IFN mediated antiviral state. Human U251 cells were pre-treated for 24 h with 100 U of IFN. Subsequently, cells were either pre-treated with DCPDF or vehicle then challenged with VSVΔ51 for 48 hours. Cells were then fixed and stained using coomassie blue.
Figure 10B:
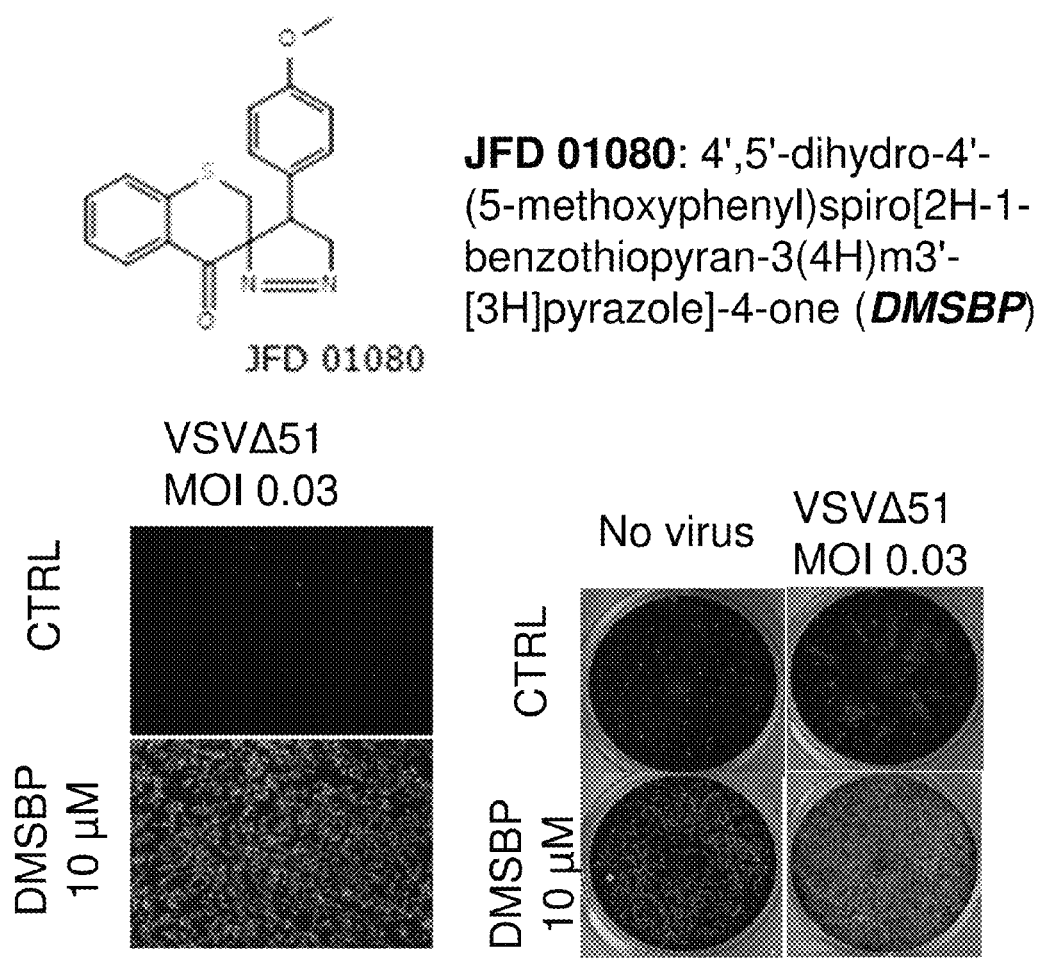

The following description is of a preferred embodiment.

In a first aspect, there is provided compounds which increase or enhance viral spread in cancer cells, tumors or immortalized cells, such as, for example, CT-26, 4T1 breast cancer cells, 786-0, U-251, B16 melanoma cells and colon tumors but not normal or non-immortalized cells.

In a further aspect, there is provided compounds which increase or enhance viral titers in cells, for example, CT-26 cells, 786-0, 4T1, colon tumor, vulvar tumor and bone tumor cells but not normal or non-immortalized cells.

In still a further aspect, there is provided compounds which increase cytotoxicity of viruses, particularly oncolytic viruses in cells.

Based on results obtained for specific compounds in various comprehensive screens as described herein and having regard to the results obtained from several structure-functional analyses, a broad class of compounds and several subclasses was identified which exhibit one or more of the properties as described above, or which may be employed as controls in in-vivo or in-vitro experiments or in additional structure-function analyses to determine additional compounds with interesting features as described herein.

The present invention concerns viral sensitizing compounds of formula (I)

an N-oxide, pharmaceutically acceptable addition salt, quarternary amine or stereochemically isomeric form thereof, wherein:

A is a 5-membered heterocylic ring comprising 1-4 heteroatoms selected from 0, N or S and 1 or 2 double bonds;

$R^1$ is H, oxo, alkoxycarbonyl, hydrazinylcarbonylalkyl or amino;

$R^2$ is nothing, alkyl, halogen, carboxyl, heteroarylcarbonylamino or hydroxyl;

$R^3$ is nothing, H, alkyl, halogen or heterocyclylaminosulfonyl, and $R^4$ is H, alkyl, unsubstituted aryl or aryl substituted with 1-3 halogens.

An interesting group of compounds are those compounds of formula (I) wherein,

A is $X_1$ is O, NH or S;

$R^1$ is H, oxo, alkoxycarbonyl, hydrazinylcarbonylalkyl or amino;

$R^2$ is nothing, alkyl, halogen, carboxyl, heteroarylcarbonylamino or hydroxyl;

$R^3$ is nothing, H, alkyl, halogen or heterocyclylaminosulfonyl, and $R^4$ is H, alkyl, unsubstituted aryl or aryl substituted with 1-3 halogens.

A further interesting group of compounds are those compounds of formula (I), for example, but not limited to formula (II)

wherein, $X_1$ is O, N, NH or S;

$X_2$, $X_3$ and $X_4$ are independently C or N;

$X_5$ is C;

$R^1$ is H, oxo, alkoxycarbonyl, hydrazinylcarbonylalkyl or amino;

$R^2$ is nothing, alkyl, halogen, carboxyl, heteroarylcarbonylamino or hydroxyl;

$R^3$ is nothing, H, alkyl, halogen or heterocyclylaminosulfonyl;

$R^4$ is H, alkyl, unsubstituted aryl or aryl substituted with 1-3 halogens;

wherein the bond between the atoms $X_2$ and $X_3$ is a single or a double bond;

wherein the bond between the atoms $X_3$ and $X_4$ is a single or a double bond;

wherein the bond between the atoms $X_4$ and $X_5$ is a single or a double bond;

wherein the bond between the atoms $X_5$ and $X_1$ is a single or a double bond;

wherein when the bond between the atoms $X_2$ and $X_3$ and the bond between $X_4$ and $X_5$ are each single bonds, the bond between the atoms $X_3$ and $X_4$ is a double bond, the bond between the atoms $X_5$ and $X_1$ is a single bond, $X_2$ is C and $R^1$ is oxo; or wherein when the bond between the atoms $X_2$ and $X_3$ and the bond between $X_4$ and $X_5$ are each single bonds, the bond between the atoms $X_3$ and $X_4$ is a double bond, the bond between the atoms $X_5$ and $X_1$ is a double bond and $X_1$ is N, or wherein when the bond between the atoms $X_2$ and $X_3$ and the bond between $X_4$ and $X_5$ are each double bonds, the bond between the atoms $X_3$ and $X_4$ is a single bond and the bond between $X_5$ and $X_1$ is a single bond.

A further interesting group of compounds are those compounds of formula (I), for example, but not limited to formula (III)

(III)

wherein:

$X_1$ is O, NH or S;

$R^2$ is alkyl, halogen, carboxyl or hydroxyl;

$R^3$ is alkyl or halogen, and $R^4$ is alkyl, unsubstituted aryl or aryl substituted with 1-3 halogens.

A further interesting group of compounds are those of formula (I), for example, but not limited to

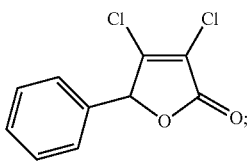

3,4-dichloro-5-phenyl-2,5-dihydrofuran-2-one

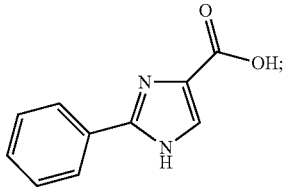

2-phenyl-1H-imidazole-4-carboxylic acid 1.5 hydrate

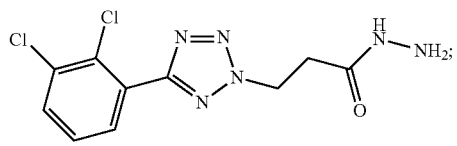

3-[5-(2,3-dichlorophenyl)-2H-1,2,3,4-tetraazol-2-yl]propanohydrazide

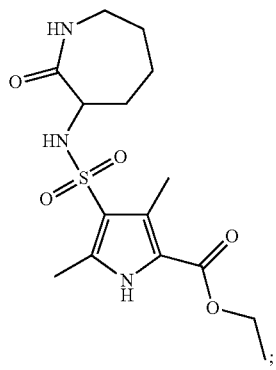

ethyl 3,5-dimethyl-4-{[(2-oxo-3-azepanyl)amino]sulfonyl}1H-pyrrole-2-carboxylate

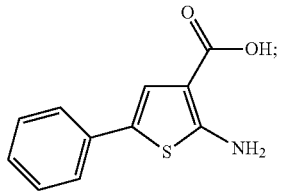

2-amino-5-phenyl-3-thiophenecarboxylic acid

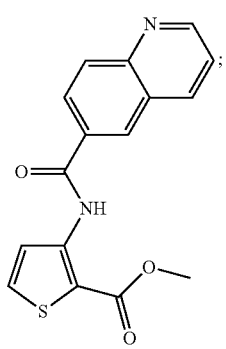

methyl 3-[(quinolin-6-ylcarbonyl)amino]thiophene-2-carboxylate

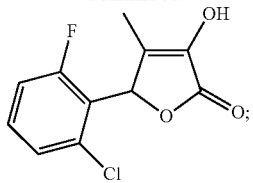

5-(2-chloro-6-fluorophenyl)-3-hydroxy-4-methyl-2,5-dihydrofuran-2-one, and

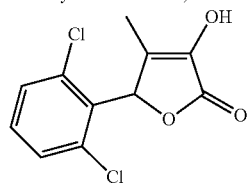

5-(2,6-dichlorophenyl)-3-hydroxy-4-methyl-2,5-dihydrofuran-2-one

The present invention also concerns compounds of formula

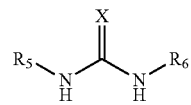

(IV)

wherein,

X is O or S;

R$_5$ is hydroxyalkyl, heteroaryl, unsubstituted aryl, aryl substituted with one or more substituents selected from the group consisting of alkyl and halogen, heterocyclyl or benzodioxylalkyl; and R$_6$ is amino, aryl or aryl substituted with one or more substituents selected from the group consisting of alkyl and halogen.

A further interesting group of compounds are those compounds of formula (IV), for example, but not limited to

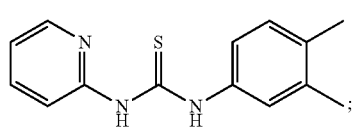

N-(3,4-dimethylphenyl)-N'-(2-pyridyl)thiourea

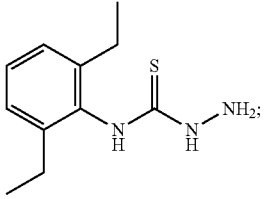

N1-(2,6-diethylphenyl)hydrazine-1-carbothioamide

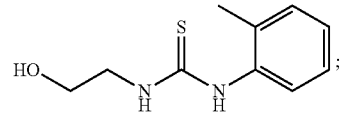

N-(2-hydroxyethyl)-N'-(2-methylphenyl)thiourea

15
-continued

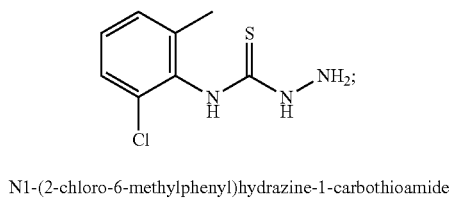

N1-(2-chloro-6-methylphenyl)hydrazine-1-carbothioamide

16
-continued

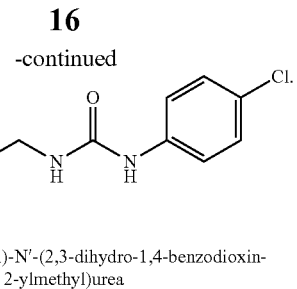

N-(4-chlorophenyl)-N'-(2,3-dihydro-1,4-benzodioxin-2-ylmethyl)urea

Additional interesting compounds are identified in Table 1.

TABLE 1

Structures and Chemical Names of Some Viral Sensitizing Compounds

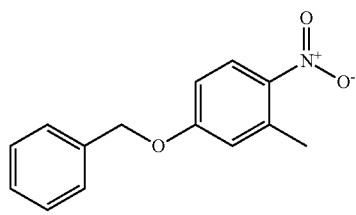 [SMILES: Cc1cc(OCc2ccccc2)ccc1[N+](=O)[O-]]

4-(benzyloxy)-2-methyl-1-nitrobenzene

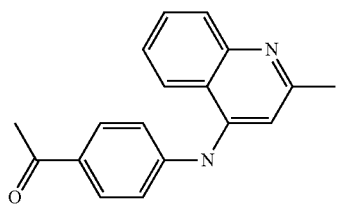 [SMILES: CC(=O)c1ccc(Nc2cc(C)nc3ccccc23)cc1]

1-{4-[(2-methylquinolin-4-yl)amino]phenyl}ethan-1-one

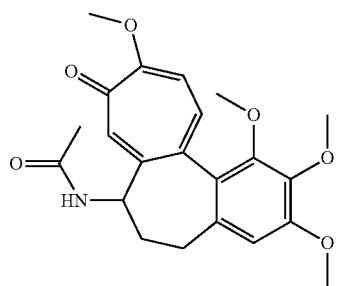 [SMILES: COc1cc2c(c(OC)c1OC)-c1ccc(OC)c(=O)cc1C(NC(C)=O)CC2]

N1-(1,2,3,10-tetramethoxy-9-oxo-5,6,7,9-tetrahydrobenzo[a]heptalen-7-yl)acetamide

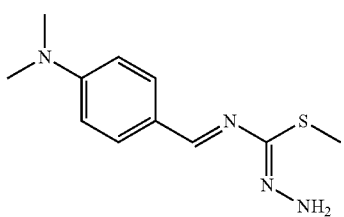

methyl N-[4-(dimethylamino)benzylidene]aminomethanehydrazonothioate

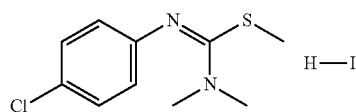

methyl N-(4-chlorophenyl)-(dimethylamino)methanimidothioate hydroiodide

TABLE 1-continued

Structures and Chemical Names of Some Viral Sensitizing Compounds

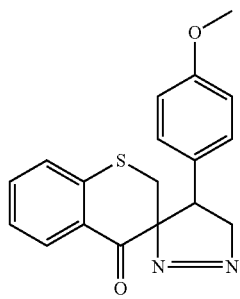

JFD 01080

4',5'-dihydro-4'-(5-methoxyphenyl)spiro[2H-1-benzothiopyran-3(4H)m3'-[3H]pyrazole]-4-one

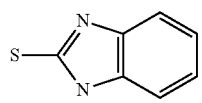

S 00965

1H-benzo[d]imidazole-2-thiol

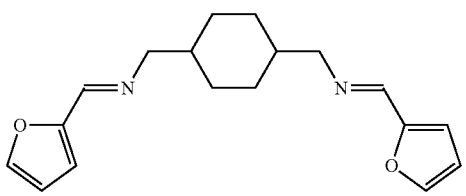

S 01517

N-(2-furylmethylidene)-(4-{[(2-furylmethylidene)amino]methyl}cyclohexyl)methanamine

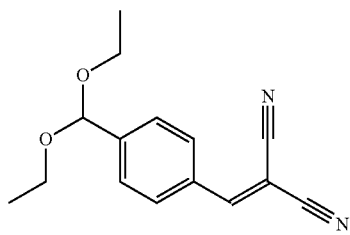

KM 01762

2-[4-(diethoxymethyl)benzylidene]malononitrile

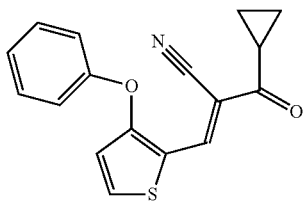

KM 05513

2-(cyclopropylcarbonyl)-3-(3-phenoxy-2-thienyl)acrylonitrile

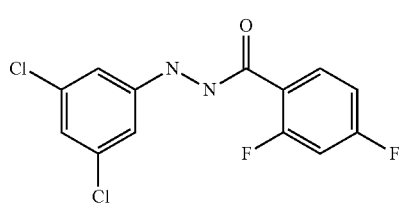

HTS 06177

N'-(3,5-dichlorophenyl)-2,4-difluorobenzohydrazide

TABLE 1-continued
Structures and Chemical Names of Some Viral Sensitizing Compounds
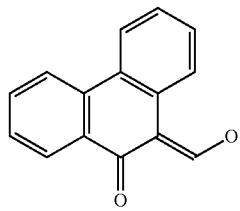
JFD 03665
10-(hydroxymethylene)phenanthren-9(10H)-one
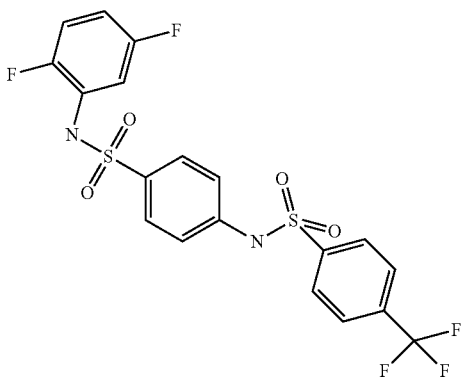
RJF 02119
N1-(2,5-difluorophenyl)-4-({[4-(trifluoromethyl)phenyl]sulfonyl}amino)benzene-1-sulfonamide
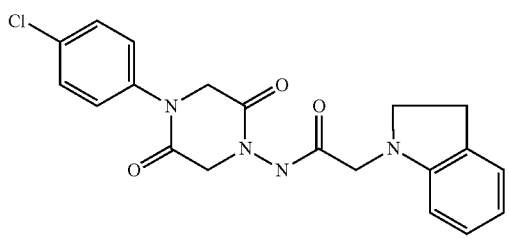
HTS 12894
N-[4-(4-chlorophenyl)-2,5-dioxopiperazino]-2-(2,3-dihydro-1H-indol-1-yl)acetamide
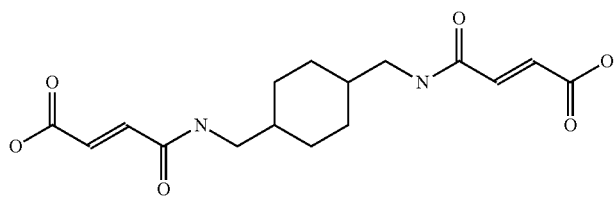
S 01365
4-{[(4-{[(3-carboxyacryloyl)amino]methyl}cyclohexyl)methyl]amino}-4-oxo-2-butenoic acid TABLE 1-continued Structures and Chemical Names of Some Viral Sensitizing Compounds

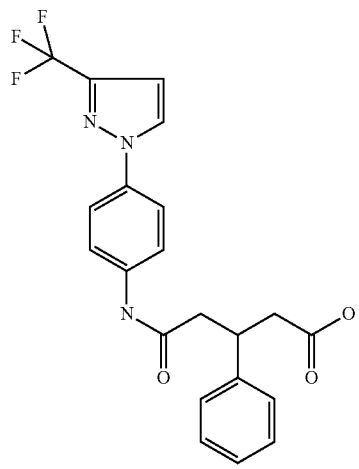

HTS 05210

5-oxo-3-phenyl-5-{4-[3-(trifluoromethyl)-1H-pyrazol-1-yl]anilino}pentanoic acid

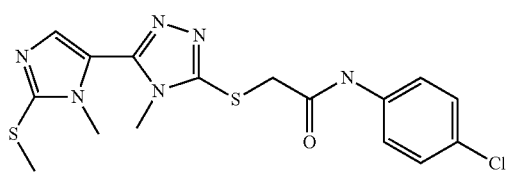

KM 07084

N1-(4-chlorophenyl)-2-({4-methyl-5-[1-methyl-2-(methylthio)-1H-imidazol-5-yl]-4H-1,2,4-triazol-3-yl}thio)acetamide

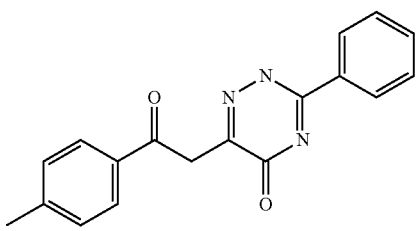

BTB 11711

6-[2-(4-methylphenyl)-2-oxoethyl]-3-phenyl-2,5-dihydro-1,2,4-triazin-5-one

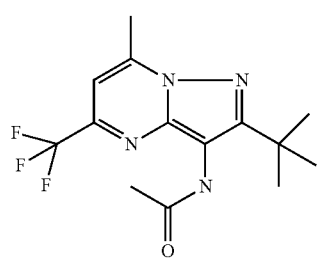

KM 10065

N1-[2-(tert-butyl)-7-methyl-5-(trifluoromethy)pyrazolo[1,5-a]pyrimidin-3-yl]acetamide

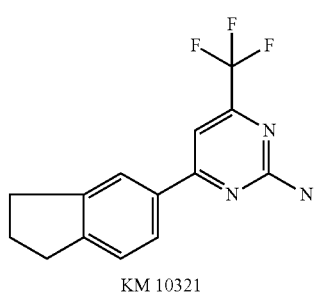 [SMILES: Nc1nc(-c2ccc3c(c2)CCC3)cc(C(F)(F)F)n1]

KM 10321

4-(2,3-dihydro-1H-inden-5-yl)-6-(trifluoromethyl)pyrimidin-2-amine

TABLE 1-continued

Structures and Chemical Names of Some Viral Sensitizing Compounds

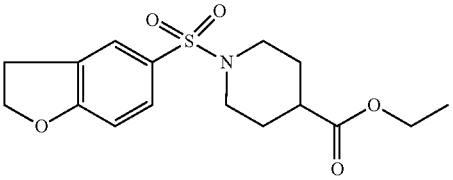

HTS 07105 ethyl 1-(2,3-dihydro-1-benzofuran-5-ylsulfonyl)-4-piperidinecarboxylate

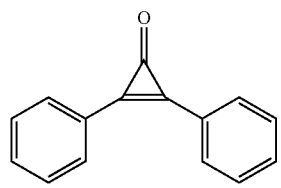

BTB 10303

2,3-diphenylcycloprop-2-en-1-one

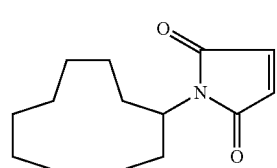

S 01369

1-cyclododecyl-1H-pyrrole-2,5-dione

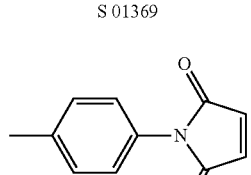

S 01335

1-(4-methylphenyl)-2,5-dihydro-1H-pyrrole-2,5-dione

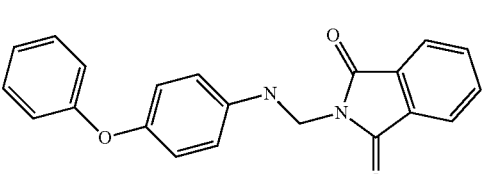

S 01647

2-[(4-phenoxyanilino)methyl]isoindoline-1,3-dione

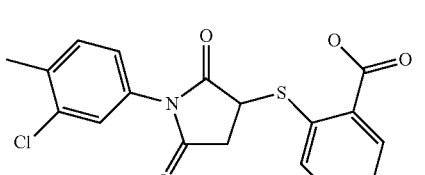

S 02334

2-{[1-(3-chloro-4-methylphenyl)-2,5-dioxotetrahydro-1H-pyrrol-3-yl]thio}benzoic acid

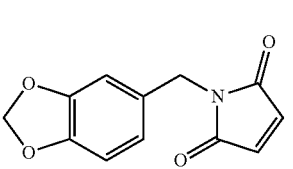

S 04055

1-(1,3-benzodioxol-5-ylmethyl)-2,5-dihydro-1H-pyrrole-2,5-dione

TABLE 1-continued

Structures and Chemical Names of Some Viral Sensitizing Compounds

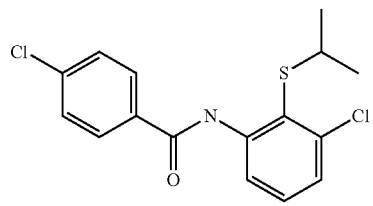

KM 10122

4-chloro-N-[3-chloro-2-(isopropylthio)phenyl]benzamide

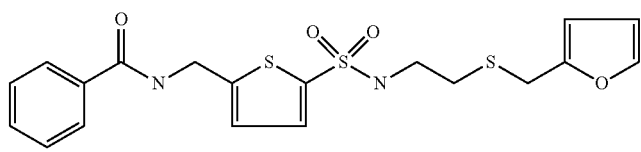

KM 10347

N-({5-[({2-[(2-furylmethyl)thio]ethyl}amino)sulfonyl]-2-thienyl}methyl)benzamide Additional interesting viral sensitizing compounds are described below in Table 2 and may be referred to by their chemical name, code or structure.

TABLE 2

Structures, Chemical Names and Reference Codes for Other Viral Sensitizing Compounds

| Name | code | Potential Target | structure |
|---|---|---|---|
| 3,4-dichloro-5-phenyl-2,5-dihydrofuran-2-one | VSe1 | antiviral response | 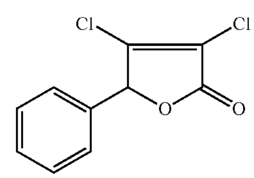 [SMILES: O=C1OC(c2ccccc2)C(Cl)=C1Cl] |
| Parbendazole | VSe2 | microtubules | 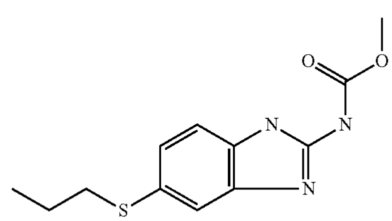 [SMILES: CCCSc1ccc2[nH]c(NC(=O)OC)nc2c1] |
| Methiazole | VSe3 | microtubules | 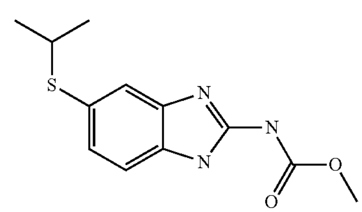 [SMILES: COC(=O)Nc1nc2cc(SC(C)C)ccc2[nH]1] |

TABLE 2-continued

Structures, Chemical Names and Reference Codes for Other Viral Sensitizing Compounds

| Name | code | Potential Target | structure |
| --- | --- | --- | --- |
| colchicine | VSe4 | microtubules | 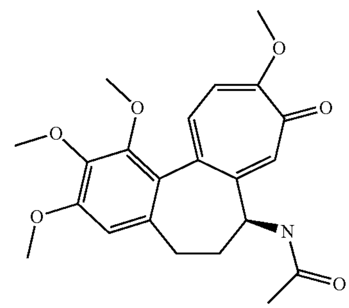 [SMILES: COc1cc2c(c(OC)c1OC)-c1ccc(OC)c(=O)cc1[C@@H](NC(C)=O)CC2] |
| Vinorelbine Base | VSe5 | microtubules | 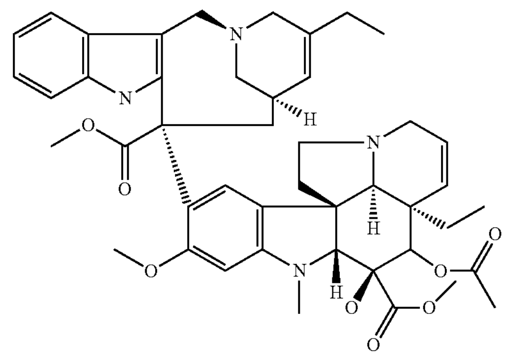 |
| ethyl 4-amino-2-anilino-5-nitrothiophene-3-carboxylate | VSe6 | unknown (suspected microtubules) | 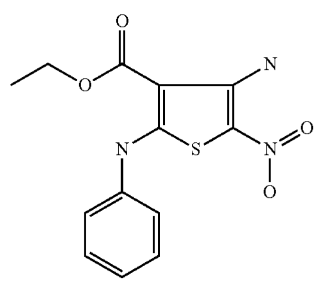 |
| 2-[di(methylthio)methylidene]malononitrile | VSe7 | unknown | 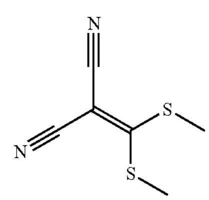 |
| N-(1H-indol-3-ylmethyl)-N-methyl-2-phenylethanamine oxalate | VSe8 | unknown | 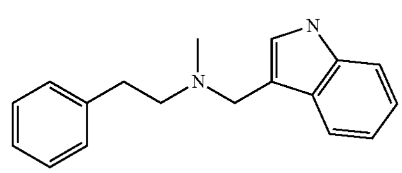 [SMILES: CN(CCc1ccccc1)Cc1c[nH]c2ccccc12] |
| 3-(2-furyl)-N-(4,5,6,7-tetrahydro-1,3-benzothiazol-2-yl)acrylamide | VSe9 | unknown (suspected microtubules) | 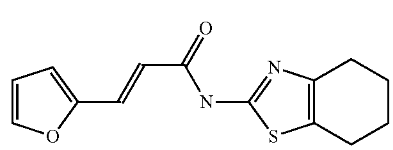 [SMILES: O=C(/C=C/c1ccco1)Nc1nc2c(s1)CCCC2] |

TABLE 2-continued

Structures, Chemical Names and Reference Codes for Other Viral Sensitizing Compounds

| Name | code | Potential Target | structure |
|---|---|---|---|
| Albendazole | VSe10 | microtubules | 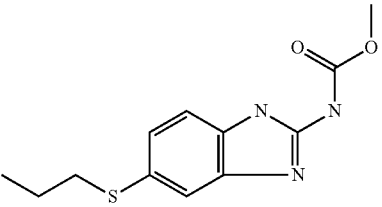 [SMILES: CCCSc1ccc2[nH]c(NC(=O)OC)nc2c1] |
| 2-phenyl-4-quinolinamine oxalate | VSe11 | unknown (suspected microtubules) | 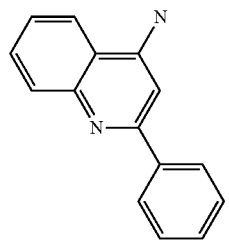 [SMILES: Nc1cc(-c2ccccc2)nc2ccccc12] |
| Paclitaxel | Vse12 | microtubules | 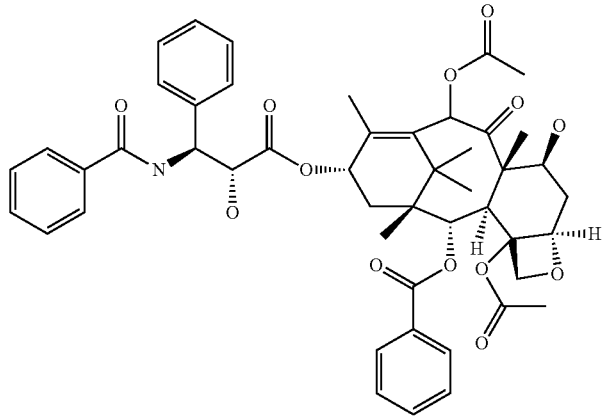 |
| Nocodazole | Vse13 | microtubules | 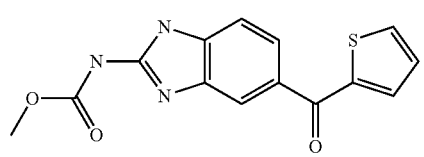 [SMILES: COC(=O)Nc1nc2cc(C(=O)c3cccs3)ccc2[nH]1] |
| (2,5-dimethoxyphenyl)[(2-methoxy-1-naphthyl)methyl]amine | Vse14 | unknown (suspected microtubules) | 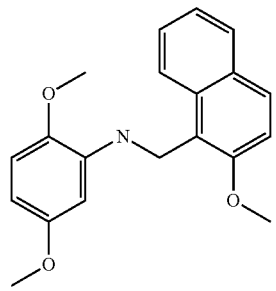 [SMILES: COc1ccc(OC)c(NCc2c(OC)ccc3ccccc23)c1] |

TABLE 2-continued

Structures, Chemical Names and Reference Codes for Other Viral Sensitizing Compounds

| Name | code | Potential Target | structure |
|---|---|---|---|
| Deacytalcholchicine N-formyl- | Vse15 | microtubules | 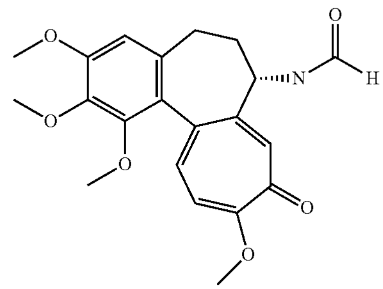 [SMILES: COc1cc2c(c(OC)c1OC)-c1ccc(OC)c(=O)cc1[C@@H](NC=O)CC2] |

By the term "viral sensitizing compound" or "viral sensitizing agent" it is meant a compound that increases or enhances the spread of a virus, preferably a genetically modified virus or attenuated virus, more preferably an oncolytic virus in one or more types of cells, preferably cancer or tumor cells but not normal or non-immortalized cells; increases or enhances the cytotoxicity/oncolytic activity of an oncolytic virus against one or more cancer or tumor cells; increases or enhances the production, yield or reproductive capacity of a virus, more preferably a genetically modified, attenuated or oncolytic virus; or any combination of the above. It is also preferred that the viral sensitizing compound reduces the viability of a cancer or tumor cell by either killing the cancer or tumor cells or limiting its growth for a period of time.

By the term "oncolytic virus" it is meant a virus that preferentially infects and lyses cancer or tumor cells as compared to normal cells. Cytotoxic/oncolytic activity of the virus may be present, observed or demonstrated in vitro, in vivo, or both. Preferably, the virus exhibits cytotoxic/oncolytic activity in vivo. Examples of oncolytic viruses known in the art include, without limitation, reovirus, newcastle disease virus, adenovirus, herpes virus, polio virus, mumps virus, measles virus, influenza virus, vaccinia virus, rhabdovirus, vesicular stomatitis virus and derivatives/variants thereof.

By a "derivative" or "variant" of a virus, it is meant a virus obtained by selecting the virus under different growth conditions, one that has been subjected to a range of selection pressures, one that has been genetically modified using recombinant techniques known within the art, or any combination thereof. Examples of such viruses are known in the art, for example from US patent applications 20040115170, 20040170607, 20020037543, WO 00/62735; U.S. Pat. Nos. 7,052,832, 7,063,835, 7,122,182 (which are hereby incorporated by reference) and others. Preferably the virus is a Vesicular stomatitis virus (VSV), or a variant/derivative thereof, for example, selected under specific growth conditions, one that has been subjected to a range of selection pressures, one that has been genetically modified using recombinant techniques known within the art, or a combination thereof. In a preferred embodiment, the virus is VSVΔ51 (Stojdl et al., VSV strains with defects in their ability to shutdown innate immunity are potent systemic anti-cancer agents, Cancer Cell. 2003 October; 4(4):263-75, herein incorporated by reference).

By the term "alkyl" it is meant a straight or branched chain alkyl having 1 to 20 carbon atoms, more particularly 1 to 8 carbon atoms, or even more particularly 1 to 6 carbon atoms. Examples of alkyl groups include methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl.

The one or more types of cancer or tumor cells may be cancer cells in vitro or in vivo from any cell, cell line, tissue or organism, for example, but not limited to human, rat, mouse, cat, dog, pig, primate, horse and the like. In a preferred embodiment, the one or more cancer or tumor cells comprise human cancer or tumor cells, for example, but not limited to lymphoblastic leukemia, myeloid leukemia, adrenocortical carcinoma, AIDS-related cancers, AIDS-related lymphoma, anal cancer, appendix cancer, astrocytoma, atypical teratoid/rhabdoid tumor, basal cell carcinoma, bile duct cancer, bladder cancer, bone cancer, osteosarcoma, malignant fibrous histiocytoma, brain stem glioma, brain tumor, cerebellar astrocytoma, cerebral astrocytoma/malignant glioma, craniopharyngioma, ependymoblastoma, medulloblastoma, pineal parenchymal tumors of intermediate differentiation, supratentorial primitive neuroectodermal tumors and pineoblastoma, visual pathway and hypothalamic glioma, spinal cord tumors, breast cancer, bronchial tumors, Burkitt lymphoma, carcinoid tumor, central nervous system lymphoma, cervical cancer, chordoma, chronic lymphocytic leukemia, chronic myelogenous leukemia, chronic myeloproliferative disorders, colon cancer, cutaneous T-Cell lymphoma, embryonal tumors, endometrial cancer, ependymoblastoma, ependymoma, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), gastrointestinal stromal cell tumor, germ cell tumors, extracranial, extragonadal, ovarian, gestational trophoblastic tumor, glioma, hairy cell leukemia, head and neck cancer, hepatocellular (Liver) cancer, histiocytosis, Langerhans cell cancer, Hodgkin lymphoma, hypopharyngeal cancer, islet cell tumors, Kaposi sarcoma, kidney cancer, laryngeal cancer, lymphocytic leukemia, hairy cell leukemia, lip and oral cavity cancer, liver cancer, non-small cell lung cancer, small cell lung cancer, Hodgkin lymphoma, non-Hodgkin lymphoma, malignant fibrous histiocytoma of bone and osteosarcoma, medulloblastoma, medulloepithelioma, melanoma, intraocular melanoma, Merkel cell carcinoma, mesothelioma, metastatic squamous neck cancer, mouth cancer, multiple endocrine neoplasia syndrome, multiple myeloma/plasma cell neoplasm, nasal cavity and paranasal sinus cancer, nasopharyngeal cancer, neuroblastoma, oral cancer, oropharyngeal cancer, ovarian cancer, pancreatic cancer, parathyroid cancer, penile cancer, pharyngeal cancer, pheochromocytoma, pineal parenchymal tumors, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, renal pelvis and ureter cancer, transitional cell cancer, respiratory tract carcinoma, retinoblastoma, rhabdomyosarcoma, salivary gland cancer, uterine sarcoma, skin cancer, Merkel cell skin carcinoma, small intestine cancer, soft tissue sarcoma, squamous cell carcinoma, squamous neck cancer, stomach (Gastric) cancer, supratentorial primitive neuroectodermal tumors, T-Cell lymphoma, testicular cancer, throat cancer, thymoma and thymic carcinoma, thyroid cancer, trophoblastic tumor, urethral cancer, uterine cancer, endometrial cancer, uterine sarcoma, vaginal cancer, vulvar cancer, or Wilms tumor. However, the compounds and compositions described herein may be used to treat any other cancer or tumor in vivo or in vitro.

The present invention also provides a composition comprising a) one or more viral sensitizing compounds as described herein and b) one or more additional components, for example, but not limited to, a carrier, diluent or excipient, a pharmaceutically acceptable carrier, diluent or excipient, a virus, for example, but not limited to an attenuated virus, a genetically modified virus or an oncolytic virus, cancer or tumor cells, non-cancerous cells, cell culture media, one or more cancer therapeutics, for example, but not limited to chemotherapeutics. As an example, but not to be considered limiting in any manner, cyclophosphamide (CPA) is a common chemotherapy drug used primarily for the treatment of lymphoma, chronic lymphocytic leukemia and breast, ovarian and bladder cancers. CPA is converted into its active metabolites, 4-hydroxycyclophosphamide and aldophosphamide by liver oxidases. Use of CPA as an immune suppressant to enhance viral oncolysis has improved virotherapy efficacy in combination with HSV (15-18), adenoviruses (19), measles virus (20) reovirus (21, 22) and vaccinia virus (23).

Cisplatin binds and cross-links cellular DNA leading to apoptosis when DNA is not repaired. Cisplatin has been investigated in combination with oncolytic adenoviruses (25-34), herpes viruses (35-37), parvovirus (38), vaccinia virus (39) and vesicular stomatitis virus (40). Enhanced therapeutic activity in vitro and in vivo has been observed when combining cisplatin with adenovirus, herpesvirus, parvovirus and vaccinia virus whereas slight inhibition was observed for vesicular stomatitis virus.

Mitomycin C (MMC) is a DNA cross-linking antibiotic with antineoplastic properties. MMC exhibited synergistic cytotoxicty with HSV (40, 41). In vivo, combination herpes virus and MMC significantly improved therapeutic effects in models of gastric carcinomatosis (43) and non-small cell lung cancer (41).

Doxorubicin is an anthracycline antibiotic that intercalates into DNA and prevents the action of topoisomerase II. Doxorubicin was synergistically cytotoxic when combined with oncolytic adenovirus (42, 44) and the combination reduced tumor growth relative to the monotherapies (45). ONYX-015 was successfully combined with MAP (mitomycin C, doxorubicin and cisplatin) chemotherapy in a phase I-II clinical trial for treatment of advanced sarcomas (30).

Gancyclovir (GCV) is a widely used antiviral agent, originally developed for the treatment of cytomegalovirus infections. GCV is a guanasine analogue prodrug that upon phosphorylation by herpes virus thymidine kinase (TK) competes with cellular dGTP for incorporation into DNA resulting in elongation termination. Oncolytic viruses encoding the HSV TK gene lead to an accumulation of toxic GCV metabolites in tumor cells which interfere with cellular DNA synthesis leading to apoptosis (46). Targeted oncolytic HSV viruses in combination with GCV significantly improved survival in models of human ovarian cancer (47) and rat gliosarcoma (48). Adenoviruses, engineered to express the HSV TK gene, also show enhanced anti-tumor activity when combined with GCV (49-51).

CD/5-FC enzyme/pro-drug therapy has also proven successful in combination with oncolytic virotherapy. 5-FU is a pyrimidine analogue that inhibits the synthesis of thymidine. The anti-tumor activity of two different vaccinia viruses expressing CD was significantly enhanced when combined with 5-FC therapy in immune-competent ovarian cancer (52) and immune suppressed colon cancer models (53,54).

Taxanes are a class of chemotherapy drugs, including paclitaxel and docetaxel, which cause stabilization of cellular microtubules thereby preventing function of the cellular cytoskeleton, a requirement for mitosis. Combination of docetaxel or paclitaxel with an urothelium- or prostatetargeted adenovirus significantly reduced in vivo tumor volume and resulted in synergistic in vitro cytotoxicity (55, 56).

Rapamycin (sirolimus) is an immunosuppressant commonly used in transplant patients however it has also been shown to significantly enhance the oncolytic effects of the poxviruses myxoma and vaccinia virus (23, 57-59).

The prototypical proteosome inhibitor MG-132 enhanced cellular CAR expression in Lovo colon carcinoma cells, which was accompanied with enhanced adenovirus target gene expression and oncolysis (60).

The efficacy of oncolytic VSV against chronic lymphocytic leukemia cells was increased by combination therapy with the BCL-2 inhibitor EM20-25 (61).

One group showed that a single dose of angiostatic cRGD peptide treatment before oncolytic virus treatment enhanced the antitumor efficacy of oncolytic HSV (24, 62).

The present invention also provides a kit comprising one or more viral sensitizing compound(s) or a composition comprising same. The kit may also comprise a cell culture dish/plate or multi-well dish/plate, an apparatus to deliver the viral sensitizing compounds or a composition comprising the same to a cell, cell culture or cell culture medium, or to a subject in vivo. The kit may also comprise instructions for administering or using the viral sensitizing compound, virus, for example, but not limited to attenuated virus, genetically modified virus, oncolytic virus, any combination thereof, or any combination of distinct viruses.

For in vivo therapeutic applications, there is provided a pharmaceutical composition comprising one or more viral sensitizing compounds and a pharmaceutically acceptable carrier, diluent or excipient, optionally containing other solutes such as dissolved salts and the like. In a preferred embodiment, the solution comprises enough saline or glucose to make the solution isotonic. Pharmaceutical compositions and methods of preparing pharmaceutical compositions are known in the art and are described, for example, in "Remington: The Science and Practice of Pharmacy" (formerly "Remingtons Pharmaceutical Sciences"); Gennaro, A., Lippincott, Williams & Wilkins, Philadelphia, Pa. (2000), herein incorporated by reference.

Administration of such compositions may be via a number of routes depending upon whether local and/or systemic treatment is desired and upon the area to be treated. In a first embodiment, which is not meant to be limiting, the viral sensitizing compound is administered locally to the area to be treated. Administration may be topical (including ophthalmic and to mucous membranes including vaginal and rectal delivery), pulmonary (e.g. by inhalation or insufflation of powders or aerosols, including by nebulizer), intratracheal, intranasal, epidermal and transdermal, oral or parenteral. Parenteral administration includes intravenous, intraarterial, subcutaneous, intraperitoneal or intramuscular injection or infusion, or intracranial, e.g. intrathecal or intraventricular, administration. Also contemplated is intra-tumor injection, perfusion or delivery into the general vicinity of the tumor or injection into the vasculature supplying a tumor. Alternatively, the viral sensitizing compounds may be formulated in a tablet or capsule for oral administration. Alternate dosage forms, as would be known in the art are also contemplated.

For administration by inhalation or insufflation, the viral sensitizing compounds can be formulated into an aqueous or partially aqueous solution, which can then be utilised in the form of an aerosol. For topical use, the modulators can be formulated as dusting powders, creams or lotions in pharmaceutically acceptable vehicles, which are applied to affected portions of the skin.

Figure 17A:
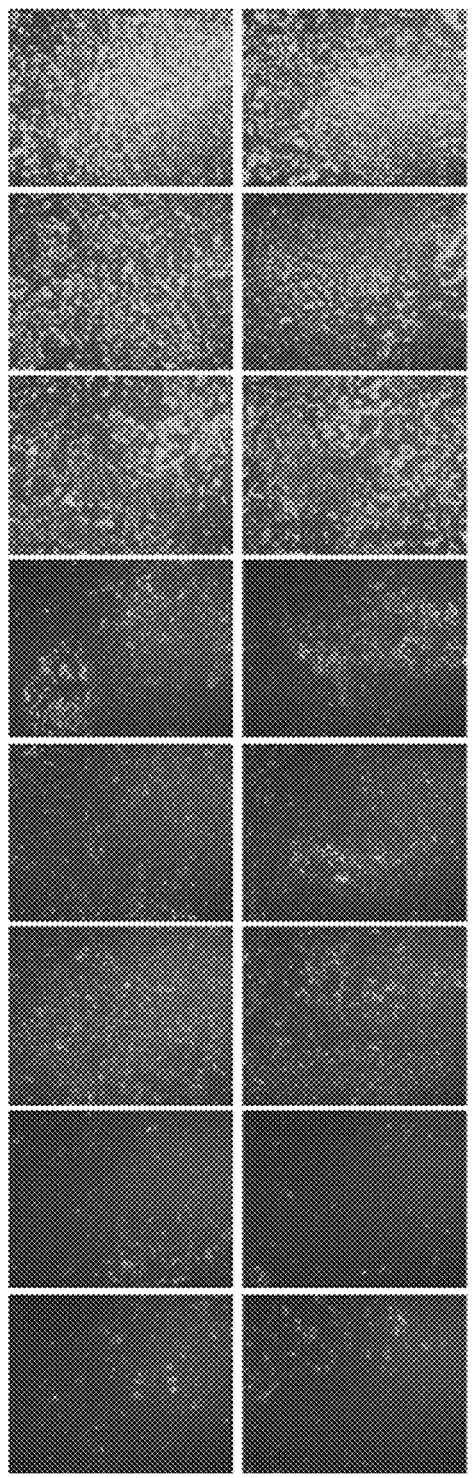
Figure 17C:
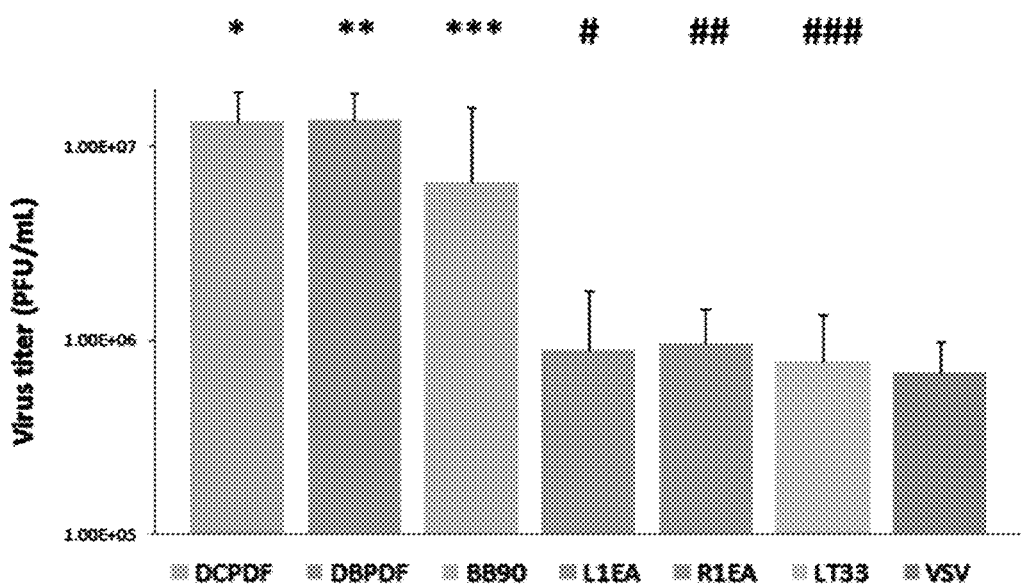
Figure 17D:
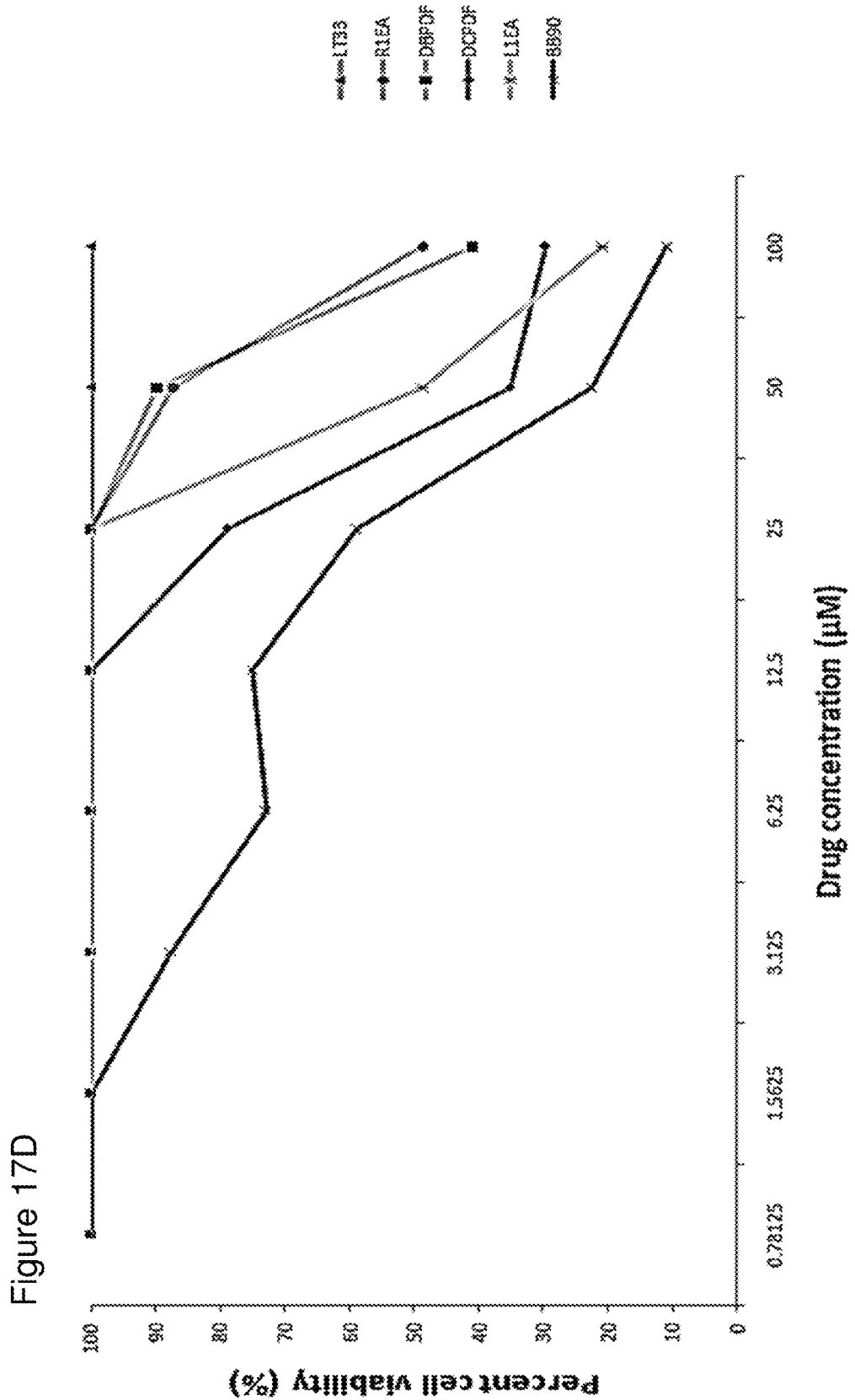
Figure 17E:
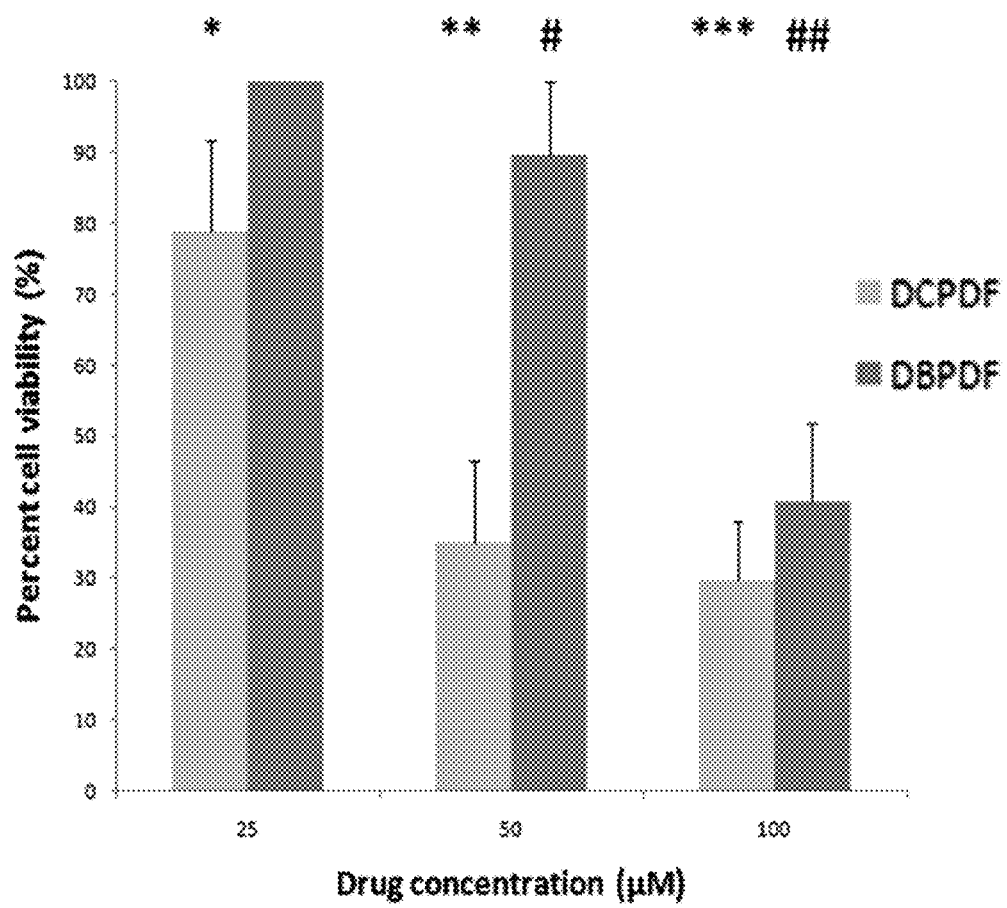
Figure 20:
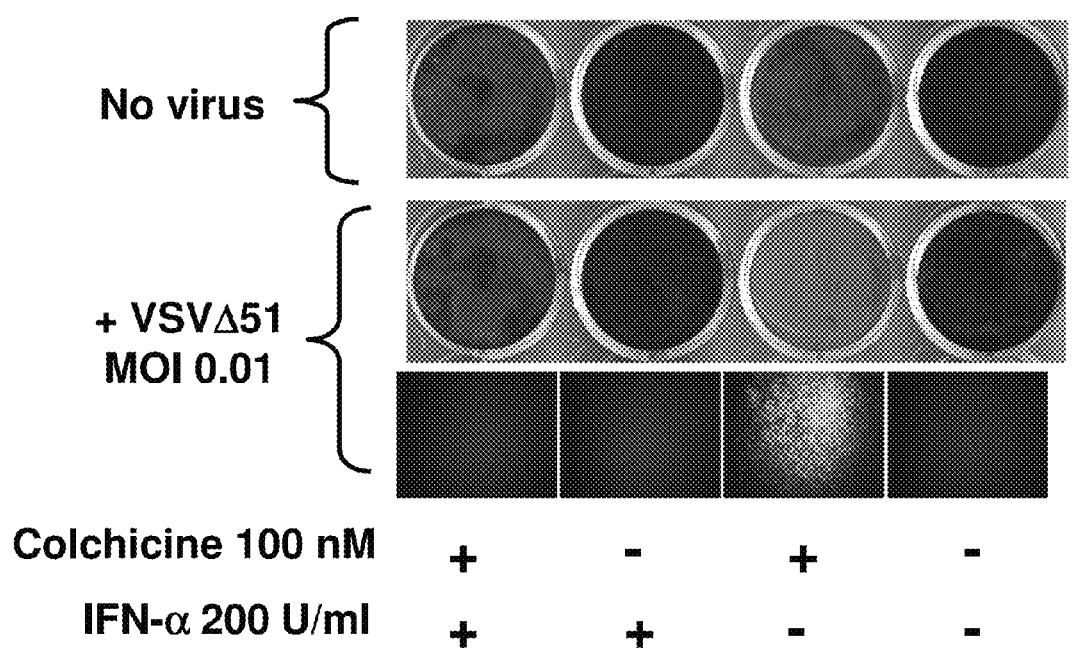
FIG. 20 shows results that colchicine does not modulate the IFN response. IFN responsive U251 cells were pre-treated with colchicine or control for 4 hours prior to addition of human IFN-alpha for 4 hours the challenged with VSVΔ51 expressing GFP. Coomassie stains were performed to assess cytotoxicity (top two panels). As expected IFN blocked VSV replication and although colchicine enhanced VSV oncolysis, it could not overcome IFN-induced antiviral effects suggesting that modulation of the IFN response does not contribute to colchicine's mode of action in contrast with other viral sensitizers such as VSe1.
Figure 21A:
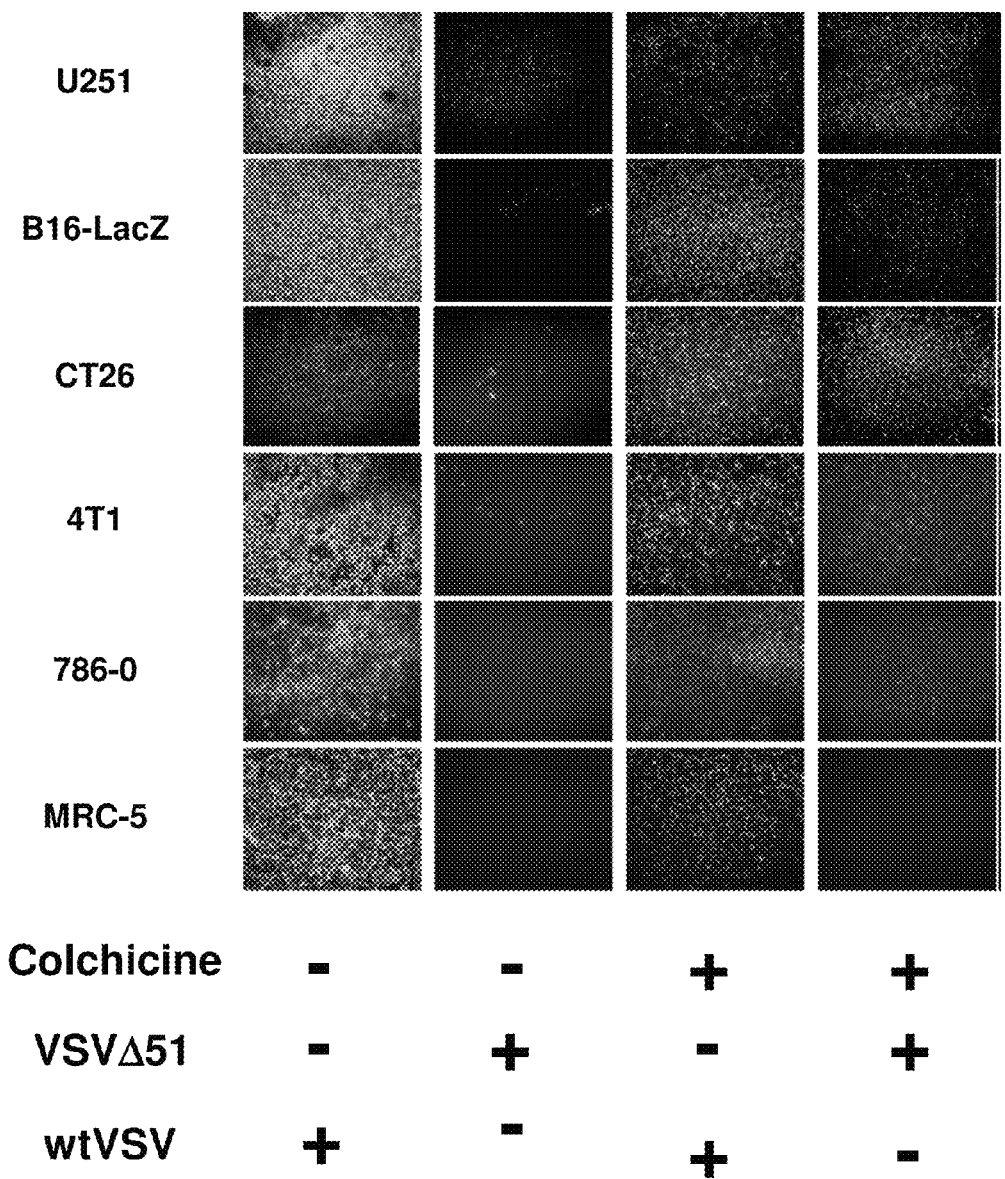
FIGS. 21A to 21B show results that colchicine increases oncolysis mediated by both wild type VSV and VSVΔ51.
Figure 21B:
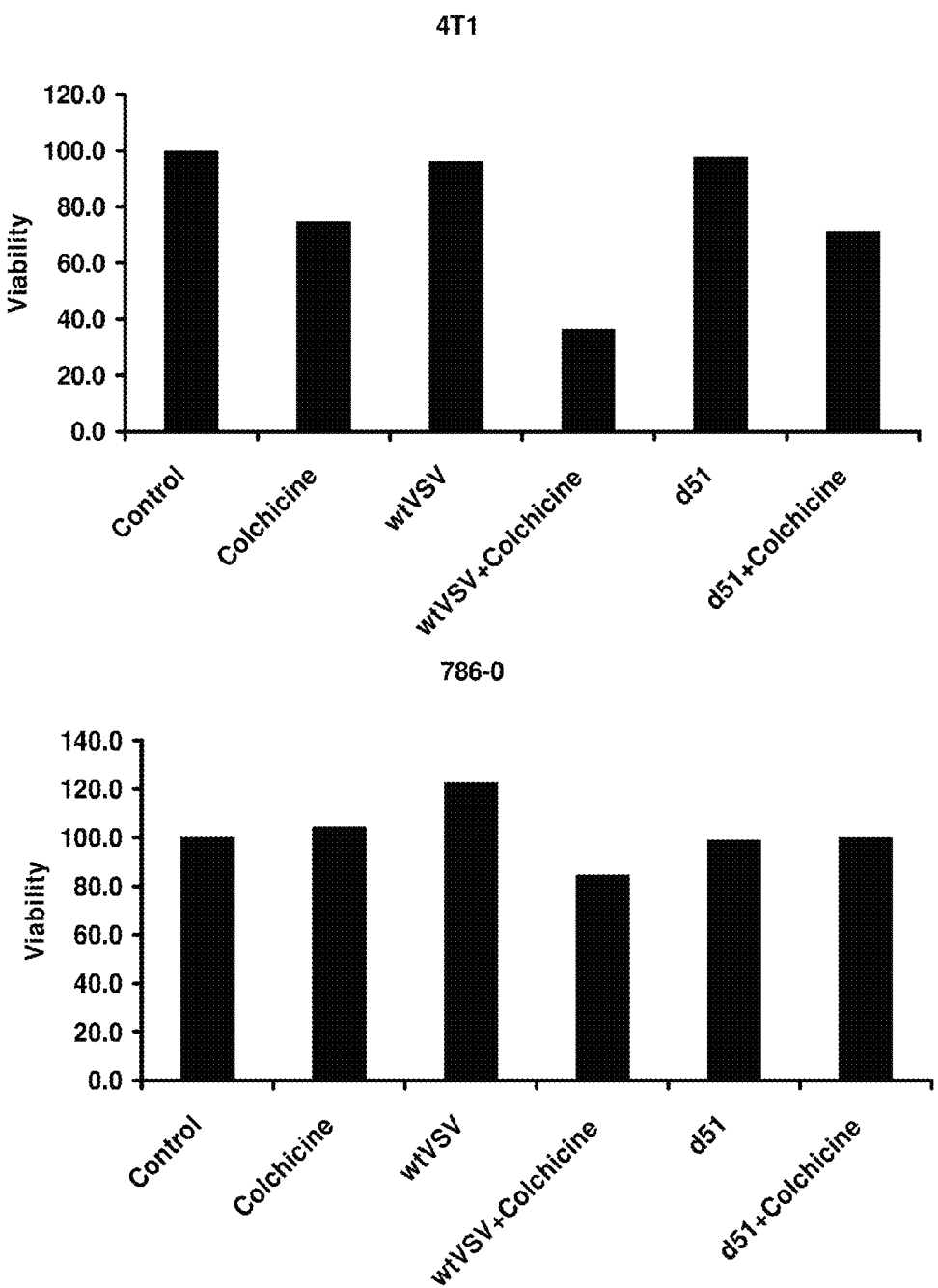
Figure 21B:
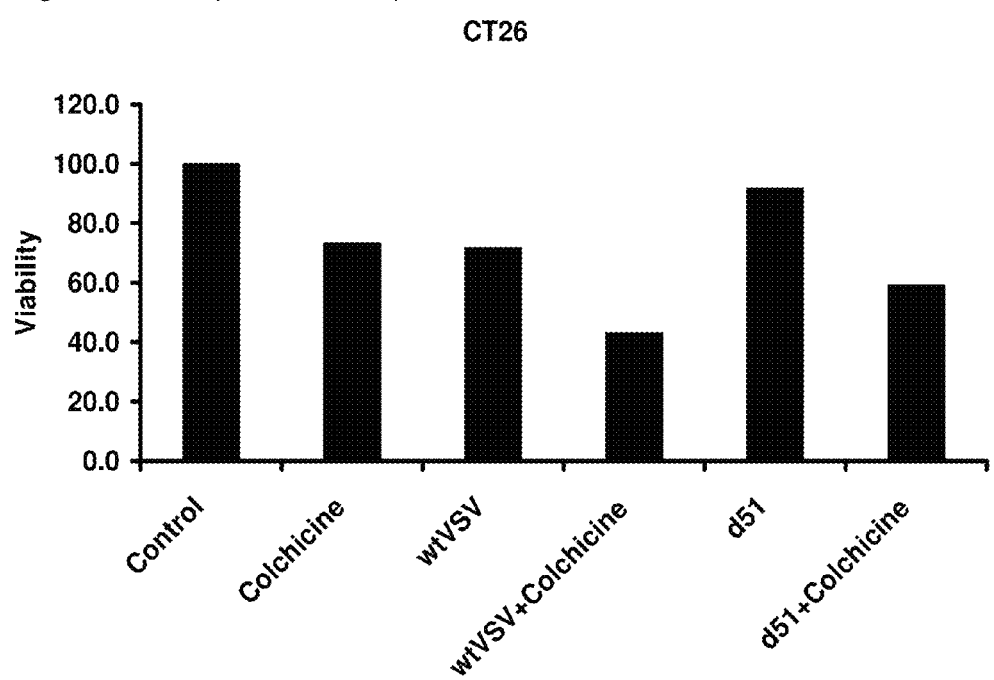

The dosage requirements for the viral sensitizing compounds of the present invention vary with the particular compositions employed, the route of administration and the particular subject being treated. Dosage requirements can be determined by standard clinical techniques known to a worker skilled in the art. Typically, treatment will generally be initiated with small dosages less than the optimum dose of the compound. Thereafter, the dosage is increased until the optimum effect under the circumstances is reached. In general, the viral sensitizing agent or pharmaceutical compositions comprising the viral sensitizing agent are administered at a concentration that will generally afford effective results without causing significant harmful or deleterious side effects. Administration can be either as a single unit dose or, if desired, the dosage can be divided into convenient subunits that are administered at suitable times throughout the day.

The viral sensitizing compound may be employed in sequential administration, for example, before, after or both before and after administration of a virus, for example, but not limited to an attenuated virus, a genetically modified virus or an oncolytic virus. Alternatively, the viral sensitizing compound may be administered in combination with a virus as described above, preferably in combination with an oncolytic virus. In addition, the viral sensitizing agent may be used with an oncolytic virus as described above and in combination with one or more cancer therapies as is known to a person of skill in the art, for example but not limited to interferon therapy, interleukin therapy, colony stimulating factor therapy, chemotherapeutic drugs, for example, but not limited to 5-fluorodeoxyuridine amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, gliadel, hydroxycarbamide, idarubicin, ifosfamide, irinotecan, leucovorin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine or a combination thereof. Further, anticancer biologics may also be employed, for example, monoclonal antibodies and the like.

The present invention also contemplates methods and uses of the compounds as described herein for increasing or enhancing the spread of a virus, for example, a genetically modified virus, an attenuated virus or an oncolytic virus in one or more cells, for example, but not limited to one or more types of cancer or tumor cells, increasing or enhancing the cytotoxicity/oncolytic activity of an oncolytic virus against one or more cancer or tumor cells, increasing or enhancing the production, yield or reproductive capacity of a virus, for example, a genetically modified virus, an attenuated virus, an oncolytic virus, or, any combination of the above. In an embodiment, which is not meant to be limiting in any manner, the viral sensitizing compound reduces the viability of a cancer or tumor cell by either killing the cancer or tumor cell or limiting its growth for a period of time. The compounds may also be used for the production of a medicament for accomplishing same.

In an embodiment of the present invention there is provided a composition comprising a viral sensitizing compound as described herein for example, one or more of 3,4-dichloro-5-phenyl-2,5-dihydrofuran-2-one, 2-phenyl-1H-imidazole-4-carboxylic acid 1.5 hydrate, 3-[5-(2,3-dichlorophenyl)-2H-1,2,3,4-tetraazol-2-yl]propanohydrazide, ethyl 3,5-dimethyl-4-{[(2-oxo-3-azepanyl)amino]sulfonyl}1H-pyrrole-2-carboxylate, 2-amino-5-phenyl-3-thiophenecarboxylic acid, methyl 3-[(quinolin-6-ylcarbonyl)amino]thiophene-2-carboxylate, 5-(2-chloro-6-fluorophenyl)-3-hydroxy-4-methyl-2,5-dihydrofuran-2-one, and 5-(2,6-dichlorophenyl)-3-hydroxy-4-methyl-2,5-dihydrofuran-2-one, N-(3,4-dimethylphenyl)-N'-(2-pyridyl)thiourea, N1-(2,6-diethylphenyl)hydrazine-1-carbothioamide, N-(2-hydroxyethyl)-N'-(2-methylphenyl)thiourea, N1-(2-chloro-6-methylphenyl)hydrazine-1-carbothioamide, N -(4-chlorophenyl)-N'-(2,3-dihydro-1,4-benzodioxin-2-ylmethyl)urea, 4-(benzyloxy)-2-methyl-1-nitrobenzene, 1-{4-[(2-methylquinolin-4-yl)amino]phenyl}ethan-1-one, N1-(1,2,3,10-tetramethoxy-9-oxo-5,6,7,9-tetrahydrobenzo[a]heptalen-7-yl)acetamide, methyl N[4-(dimethylamino)benzylidene]aminomethanehydrazonothioate, methyl N -(4-chlorophenyl)-(dimethylamino)methanimidothioate hydroiodide, 4',5'-dihydro-4'-(5-methoxyphenyl)spiro[2H-1-benzothiopyran-3(4H)m3'-[3H]pyrazole]-4-one, 1H -benzo[d]imidazole-2-thiol, N-(2-furylmethylidene)-(4-{[(2-furylmethylidene)amino]methyl}cyclohexyl)methanamine; 2-[4-(diethoxymethyl)benzylidene]malononitrile; 2-(cyclopropylcarbonyl)-3-(3-phenoxy-2-thienyl)acrylonitrile; N'-(3,5-dichlorophenyl)-2,4-difluorobenzohydrazide; 10-(hydroxymethylene)phenanthren-9(10H)-one; N1-(2,5-difluorophenyl)-4-({[4-(trifluoromethyl)phenyl]sulfonyl}amino)benzene-1-sulfonamide; N-[4-(4-chlorophenyl)-2,5-dioxopiperazino]-2-(2,3-dihydro-1H-indol-1-yl)acetamide, 4-{[(4-{[(3-carboxyacryloyl)amino]methyl}cyclohexyl)methyl]amino}-4-oxo-2-butenoic acid; 5-oxo-3-phenyl-5-{4-[3-(trifluoromethyl)-1H-pyrazol-1-yl]anilino}pentanoic acid, N1-(4-chlorophenyl)-2-({4-methyl-5-[1-methyl-2-(methylthio)-1H-imidazol-5-yl]-4H-1,2,4-triazol-3-yl}thio)acetamide, 6-[2-(4-methylphenyl)-2-oxoethyl]-3-phenyl-2,5-dihydro-1,2,4-triazin-5-one; N1-[2-(tert-butyl)-7-methyl-5-(trifluoromethyl)pyrazolo[1,5-a]pyrimidin-3-yl]acetamide; 4-(2,3-dihydro-1H-inden-5-yl)-6-(trifluoromethyl)pyrimidin-2-amine; ethyl 1-(2,3-dihydro-1-benzofuran-5-ylsulfonyl)-4-piperidinecarboxylate, 2,3-diphenylcycloprop-2-en-1-one, 1-cyclododecyl-1H-pyrrole-2,5-dione, 1-(4-methylphenyl)-2,5-dihydro-1H-pyrrole-2,5-dione, 2-[(4-phenoxyanilino)methyl]isoindoline-1,3-dione, 2-{[1-(3-chloro-4-methylphenyl)-2,5-dioxotetrahydro-1H-pyrrol-3-yl]thio}benzoic acid, 1-(1,3-benzodioxol-5-ylmethyl)-2,5-dihydro-1H-pyrrole-2,5-dione, 4-chloro-N-[3-chloro-2-(isopropylthio)phenyl]benzamide, and N-({5-[({2-[(2-furylmethyl)thio]ethyl}amino)sulfonyl]-2-thienyl} methyl)benzamide, parbendazole, methiazole, colchicine, vinorelbine base, ethyl 4-amino-2-anilino-5-nitrothiophene-3-carboxylate, 2-[di(methylthio)methylidene]malononitrile, N-(1H-indol-3-ylmethyl)-N -methyl-2-phenylethanamine oxalate, 3-(2-furyl)-N-(4,5,6,7-tetrahydro-1,3-benzothiazol-2-yl)acrylamide, albendazole, 2-phenyl-4-quinolinamine oxalate, paclitaxel, nocodazole, (2,5-dimethoxyphenyl)[(2-methoxy-1-naphthyl)methyl]amine, DBPDF, BB90, L1EA, R1EA, or LT33 (see FIGS. 17A to 17B for chemical structures).

In a further embodiment there is provided a composition comprising a viral sensitizing compound as described above except that the composition does not comprise one or more compounds selected from the group consisting of 3,4-dichloro-5-phenyl-2,5-dihydrofuran-2-one, 2-phenyl-1H-imidazole-4-carboxylic acid 1.5 hydrate, 3-[5-(2,3-dichlorophenyl)-2H-1,2,3,4-tetraazol-2-yl]propanohydrazide, ethyl 3,5-dimethyl-4-{[(2-oxo-3-azepanyl)amino]sulfonyl}1H-pyrrole-2-carboxylate, 2-amino-5-phenyl-3-thiophenecarboxylic acid, methyl 3-[(quinolin-6-ylcarbonyl)amino]thiophene-2-carboxylate, 5-(2-chloro-6-fluorophenyl)-3-hydroxy-4-methyl-2,5-dihydrofuran-2-one, and 5-(2,6-dichlorophenyl)-3-hydroxy-4-methyl-2,5-dihydrofuran-2-one, N-(3,4-dimethylphenyl)-N'-(2-pyridyl)thiourea, N1-(2,6-diethylphenyl)hydrazine-1-carbothioamide, N-(2-hydroxyethyl)-N'-(2-methylphenyl)thiourea, N1-(2-chloro-6-methylphenyl)hydrazine-1-carbothioamide, N-(4-chlorophenyl)-N'-(2,3-dihydro-1,4-benzodioxin-2-ylmethyl)urea, 4-(benzyloxy)-2-methyl-1-nitrobenzene, 1-{4-[(2-methylquinolin-4-yl)amino]phenyl}ethan-1-one, N1-(1,2,3,10-tetramethoxy-9-oxo-5,6,7,9-tetrahydrobenzo[a]heptalen-7-yl)acetamide, methyl N-[4-(dimethylamino)benzylidene]aminomethanehydrazonothioate, methyl N-(4-chlorophenyl)-(dimethylamino)methanimidothioate hydroiodide, 4',5'-dihydro-4'-(5-methoxyphenyl)spiro[2H-1-benzothiopyran-3(4H)m3'-[3H]pyrazole]-4-one, 1H-benzo[d]imidazole-2-thiol, N-(2-furylmethylidene)-(4-{[(2-furylmethylidene)amino]methyl}cyclohexyl)methanamine; 2-[4-(diethoxymethyl)benzylidene]malononitrile; 2-(cyclopropylcarbonyl)-3-(3-phenoxy-2-thienyl)acrylonitrile; N'-(3,5-dichlorophenyl)-2,4-difluorobenzohydrazide; 10-(hydroxymethylene)phenanthren-9(10H)-one; N1-(2,5-difluorophenyl)-4-({[4-(trifluoromethyl)phenyl]sulfonyl}amino)benzene-1-sulfonamide; N-[4-(4-chlorophenyl)-2,5-dioxopiperazino]-2-(2,3-dihydro-1H-indol-1-yl)acetamide, 4-{[(4-{[(3-carboxyacryloyl)amino]methyl}cyclohexyl)methyl]amino}-4-oxo-2-butenoic acid; 5-oxo-3-phenyl-5-{4-[3-(trifluoromethyl)-1H-pyrazol-1-yl]anilino}pentanoic acid, N1-(4-chlorophenyl)-2-({4-methyl-5-[1-methyl-2-(methylthio)-1H-imidazol-5-yl]-4H-1,2,4-triazol-3-yl}thio)acetamide, 6-[2-(4-methylphenyl)-2-oxoethyl]-3-phenyl-2,5-dihydro-1,2,4-triazin-5-one; N1-[2-(tert-butyl)-7-methyl-5-(trifluoromethyl)pyrazolo[1,5-a]pyrimidin-3-yl]acetamide; 4-(2,3-dihydro-1H-inden-5-yl)-6-(trifluoromethyl)pyrimidin-2-amine; ethyl 1-(2,3-dihydro-1-benzofuran-5-ylsulfonyl)-4-piperidinecarboxylate, 2,3-diphenylcycloprop-2-en-1-one, 1-cyclododecyl-1H-pyrrole-2,5-dione, 1-(4-methylphenyl)-2,5-dihydro-1H-pyrrole-2,5-dione, 2-[(4-phenoxyanilino)methyl]isoindoline-1,3-dione, 2-{[1-(3-chloro-4-methylphenyl)-2,5-dioxotetrahydro-1H-pyrrol-3-yl]thio}benzoic acid, 1-(1,3-benzodioxol-5-ylmethyl)-2,5-dihydro-1H-pyrrole-2,5-dione, 4-chloro-N-[3-chloro-2-(isopropylthio)phenyl]benzamide, and N-({5-[({2-[(2-furylmethyl)thio]ethyl}amino)sulfonyl]-2-thienyl}methyl)benzamide, parbendazole, methiazole, colchicine, vinorelbine base, ethyl 4-amino-2-anilino-5-nitrothiophene-3-carboxylate, 2-[di(methylthio)methylidene] malononitrile, N-(1H-indol-3-ylmethyl)-N -methyl-2-phenylethanamine oxalate, 3-(2-furyl)-N-(4,5,6,7-tetrahydro-1,3-benzothiazol-2-yl)acrylamide, albendazole, 2-phenyl-4-quinolinamine oxalate, paclitaxel, nocodazole, or (2,5-dimethoxyphenyl)[(2-methoxy-1-naphthyl)methyl]amine, DBPDF, BB90, L1EA, R1EA, or LT33.

As will be appreciated by a person of skill in the art, the general class structures and specific compounds as identified herein may be employed alone or in combination in any variety of compositions as required by a person of skill in the art. Without wishing to be bound by theory, potential uses for the compounds as described herein may be selected from the group consisting of increasing spread and/or viral titer in specific cells, for example, in cancer or tumor cells/tissues or cells derived from cultures that have been immortalized, increasing cytotoxicity of viruses, including oncolytic viruses in specific cells, for example, in cancer or tumor cells/tissues, for the production of viruses which may be subsequently used in the production of vaccines. Also, importantly, the compounds as described herein may also be employed as internal controls or in structure-function analyses to determine additional classes or specific molecules which exhibit similar or improved properties to those currently described herein.

A high-throughput screen for the identification of Virus Sensitizers

Figure 11A:
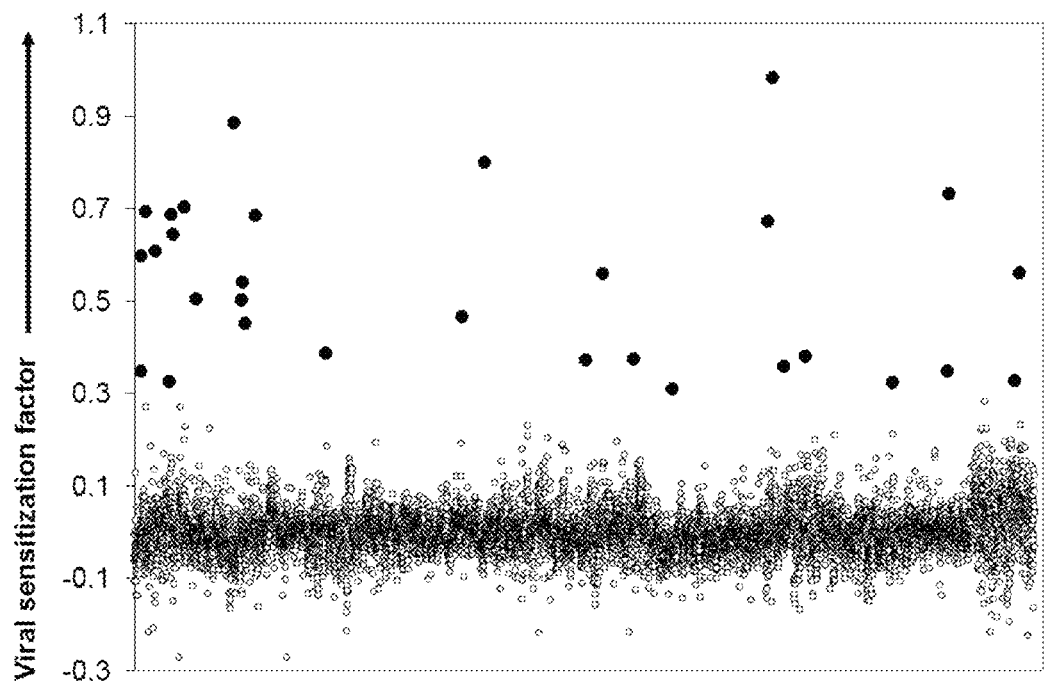
FIGS. 11A to 11C show various additional viral sensitizer candidates identified by high throughput screening and results obtained therefrom.
Figure 11B:
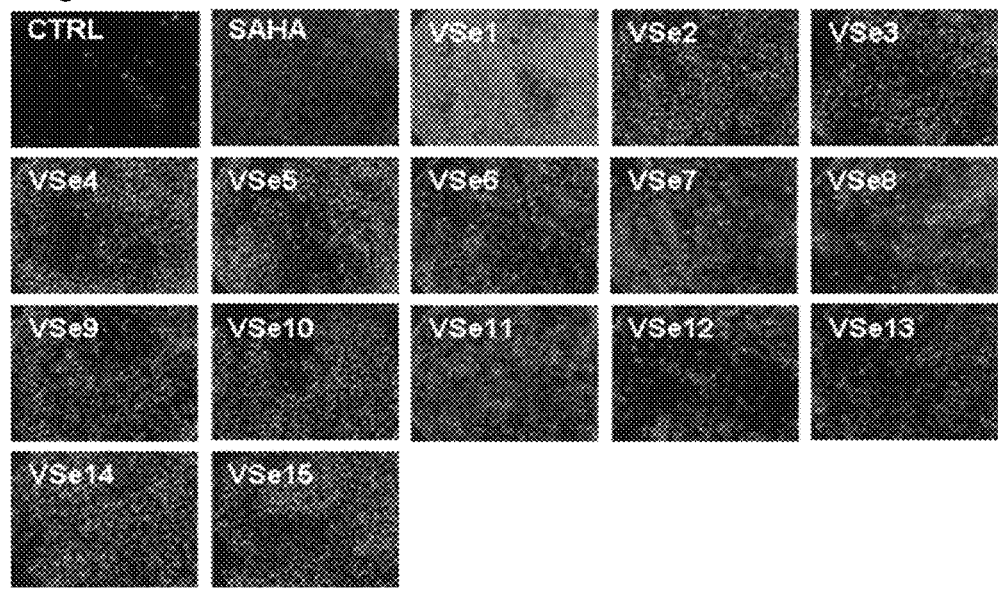
Figure 11C:
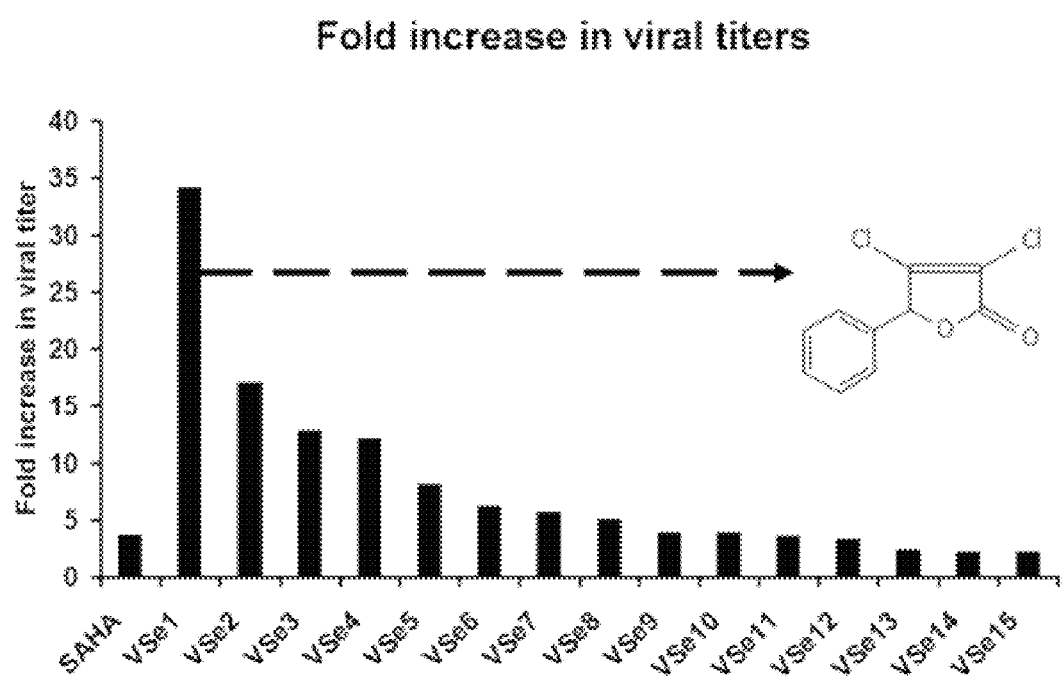
Figure 12A:
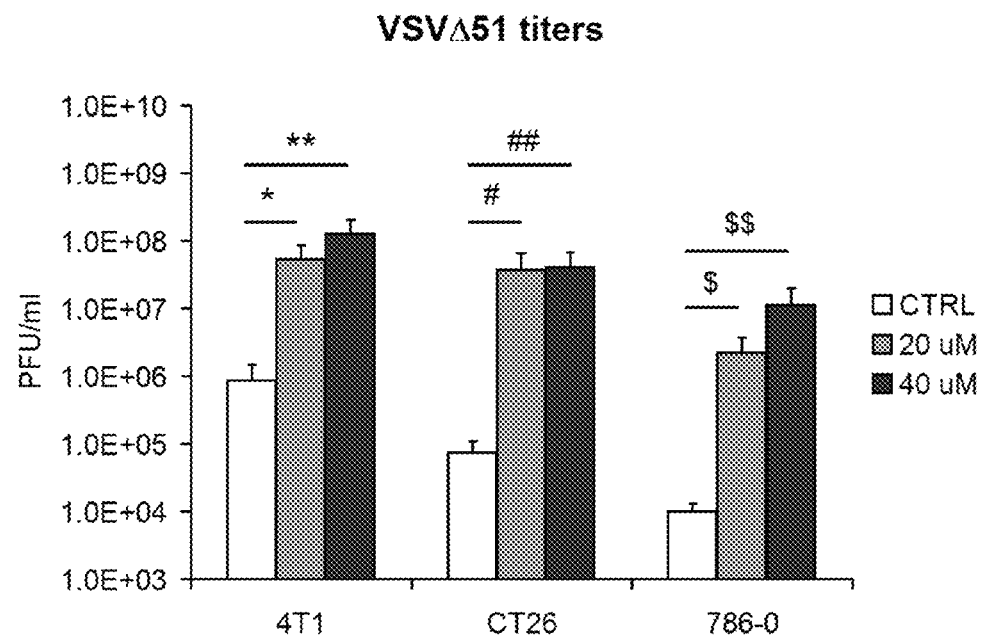
FIGS. 12A to 12C show results that VSe1 enhances VSVΔ51 spread and leads to synergistic cell killing in resistant cells.
Figure 12B:
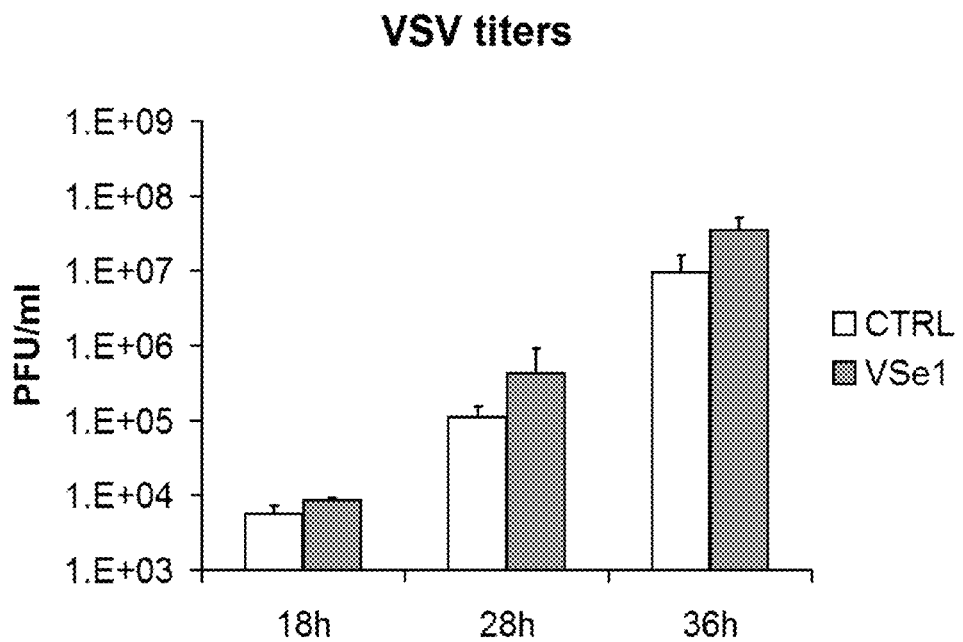
Figure 12C:
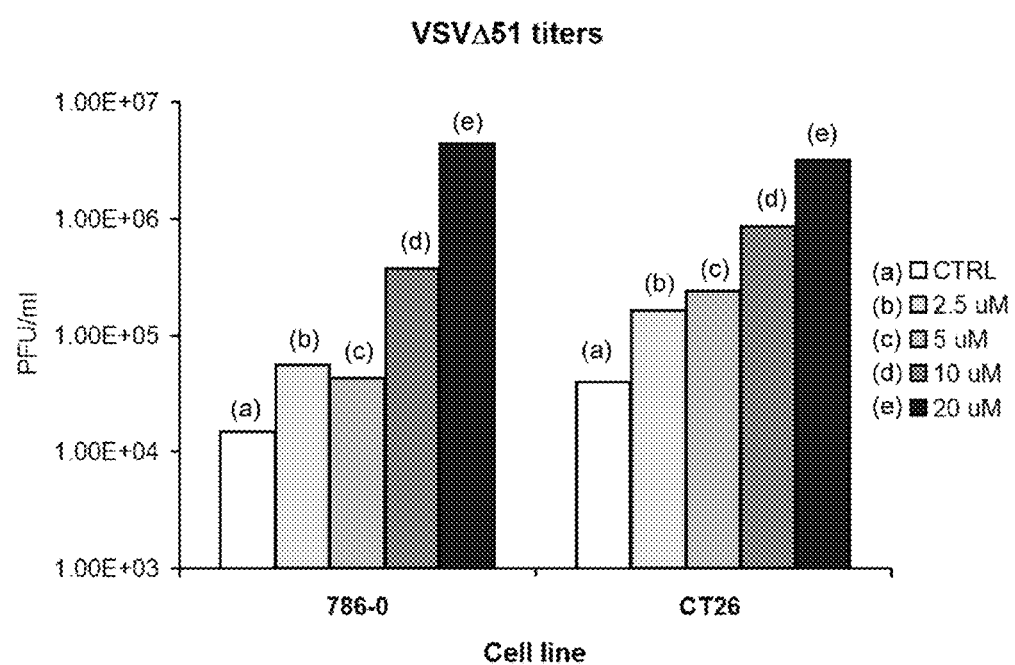

Anti-viral signaling pathways involve several layers of regulation spanning from the cellular plasma membrane (eg TLRs and IFN receptors), through the cytoplasm (eg. IKKs, Jak RIG-I,) into the nucleus (eg. IRFs, STATs, NF-κB) and back out again. Without wishing to be bound by theory or limiting in any manner this suggested that a high throughput, infected cell based screen could potentially identify viral sensitizing compounds that are active at multiple levels to enhance virus replication, etc. To test this idea, an initial screen of 12,280 synthetic drug-like molecules was carried out in combination with VSVΔ51 and a breast cancer cell line (4T1) known to be only partially permissive to this particular virus. We compared and contrasted the cytotoxicity of a given compound alone or in combination with a low dose of VSVΔ51 as described herein. Low concentrations of virus (0.03 plaque forming units per cell) were used so that virus alone caused minimal cell death over the time of the assay, thus favoring the selection of compounds that promote virus replication and spread in cell culture. A number of compounds appeared to increase virus killing of 4T1 cells and these lead candidates (see for example dot plot of FIG. 11A) were tested in a second round of screening. For validation purposes, a version of VSVΔ51 encoding RFP was added to a monolayer of 4T1 cells in the presence of selected compounds. Twenty-four hours later, infected cultures were viewed and the extent of virus spread estimated by the expression of RFP. In vehicle treated cultures, only small foci of RFP expressing cells were detected whereas many of the compounds initially selected by the high throughput screen seemed to enhance virus spread and expression of RFP in most of the cells in the monolayer. At 48 hours post infection, the supernatants from infected cultures were collected and virus titers were determined. The increase of virus spread induced by preferred compounds as described herein correlated with improved virus output when compared to vehicle treated controls. Among some of the validated compounds, eight were known microtubule targeting agents and to our knowledge, the remainder were previously uncharacterized synthetic compounds. We selected four cancer cell lines that were inherently resistant to VSVΔ51 and tested the ability of VSe1 to enhance virus replication and spread. The results suggest that VSe1 is active in different types of malignancies of human and mouse origin. Importantly, the normal fibroblast cell line GM-38 remained resistant to VSVΔ51 infection, even in the presence of VSe1, suggesting that the compound was more active in transformed cell lines. Enhanced virus spread correlated with dose dependent increases in virus production with some highly resistant cell lines (eg 786-0) exhibiting 1000 fold increases in viral titer in the presence of VSe1 (see for example FIG. 12A). Combination indices that were calculated also suggested that the effects of VSe1 on VSVΔ51 spread also translated to synergistic cell killing. We also noted that VSe1 had minimal ability to enhance the growth of VSV with a wild type M gene in the CT 26 cell line while at the same time increasing the titer of VSVΔ51 over one hundred fold. When testing the ability of VSe1 to enhance an oncolytic version of vaccina virus (VVdd), a divergent DNA virus platform, we found that while the effects were somewhat less dramatic than with VSVΔ51, VSe1 was able to enhance the spread and replication of this virus as well.

VSe1 Disrupts Anti-Viral Signaling

Figure 13A:
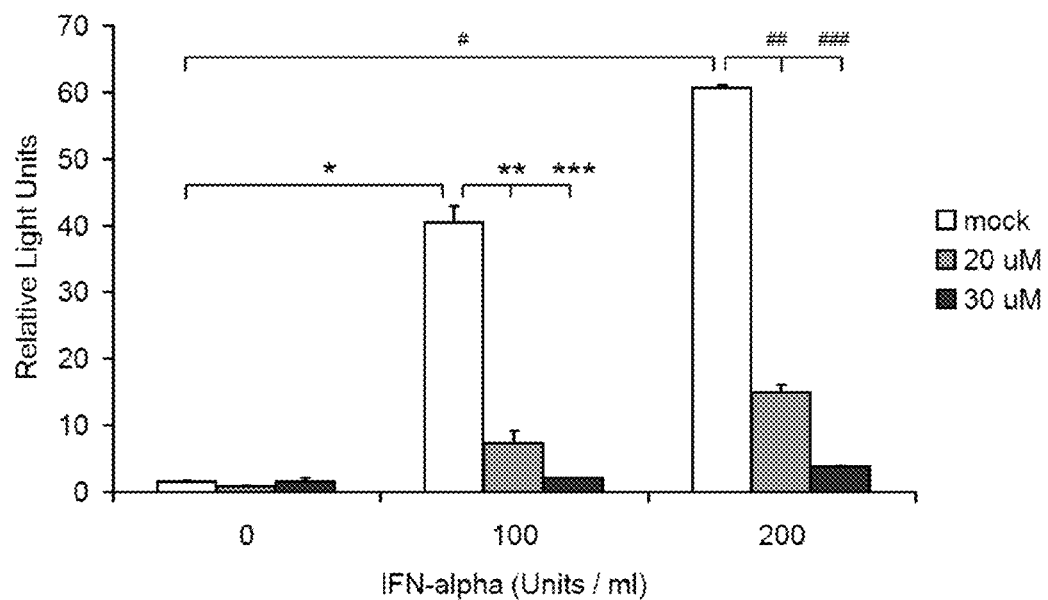
FIG. 13A show results that 293T cells were co-transfected with an ISRE-luciferase reporter and (3-galactosidase (control). 6 Hours post-transfection, cells were treated with indicated concentrations of VSe1 or vehicle. Twenty hours after receiving VSe1, media was replaced and cells were treated with IFN-α. The following day, cells were lysed and measured for luciferase activity. β-galactosidase activity was also measured and used for data normalization. *p=0.03, p=0.005, *p=0.03, #p=0.003, ##p=0.006, ###p=0.002 FIG. 13B shows human U251 glioma cells co-treated with 200 U/ml Intron A and VSe1 (or vehicle) then challenged with GFP-expressing VSVΔ51 at an MOI of 0.01. Supernatants were collected 40 hours later and titered by plaque assay on Vero cells.*p=$6.4 \times 10^{-3}$, p=$1.6 \times 10^{-4}$, *p=$6.8 \times 10^{-5}$ (ANOVA) error bars represent standard error, n=3.
Figure 13B:
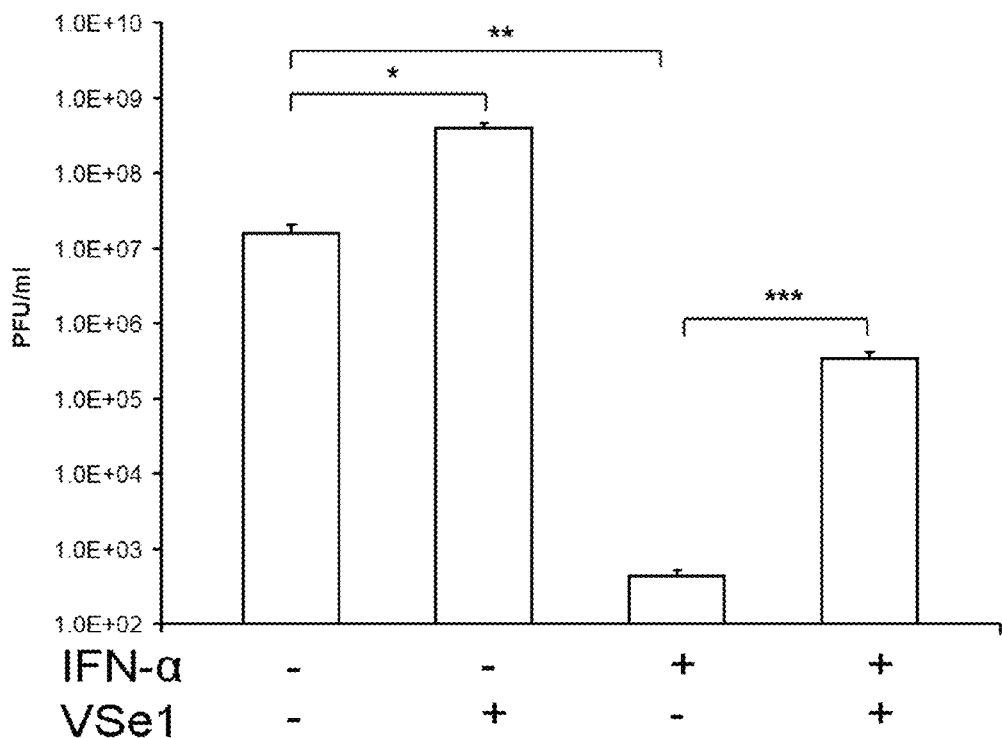
Figure 16:
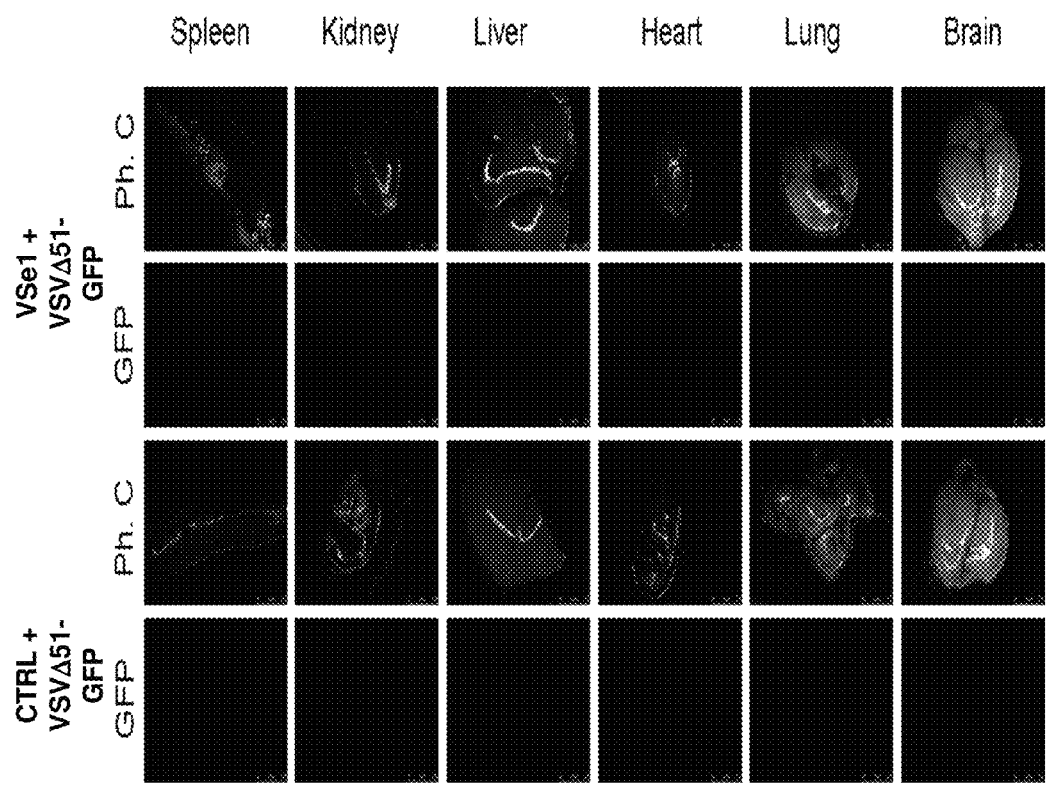
FIG. 16 shows results suggesting VSe1 does not increase VSVΔ51 replication in normal mouse tissues. Balb/C mice were treated analogously to treatment schedule presented in FIG. 15A. Briefly, a first dose of 0.4 mg VSe1 (or vehicle) was provided intraperitoneally (i.p) then challenged intravenously four hours later with $1\times10^8$ PFU GFP-expressing VSVΔ51. 48 and 96 hours later, VSe1 0.4 mg (or vehicle) was re-administered i.p and mice were sacrificed at day 6 post-infection. Organs were collected and immediately visualized using a fluorescence dissection microscope. GFP indicates GFP fluorescence pictures associated to the phase contrast (Ph.C) images shown directly above. No GFP signal was observed in any of the organs.

We examined the ability of VSe1 to block interferon activated transcription programs. HEK 293 cells were transfected with a reporter plasmid that contains the luciferase gene under the control of an interferon responsive promoter element (ISRE). When treated with human interferon alpha, the transfected cells expressed luciferase in a dose dependent fashion however interferon dependent transcription could be blunted by the addition of increasing doses of VSe1 to the cultures (see for example FIG. 13A). In addition while interferon could protect the glioma cell line U251 from VSVΔ51 infection, this protection could be partially overcome by co-treatment with VSe1 (FIG. 13B).

VSe1 Represses Virus-Induced Cellular Gene Expression

Without wishing to be bound by theory or limiting in any manner, the results presented above collectively suggest that one of the key effects of VSe1 and other viral sensitizers could be to reduce transcriptional levels of anti-viral gene products. To test this idea, we used gene expression arrays and compared and contrasted mRNA profiles in cells infected with VSVΔ51 in the presence or absence of VSe1. CT26 colon cancer cells were pre-treated with VSe1 or vehicle and subsequently infected with VSVΔ51 (MOI 0.03) or mock-infected with media. RNA was extracted 24 hours post-infection and mRNA expression was compared. We found that under these conditions VSVΔ51 infection leads to increased transcription of over 80 cellular genes including a variety of known antiviral genes (e.g. OAS, Mx2). SAHA pre-treatment significantly blunted virus induced transcription of many of these genes (79%) but in select cases appeared to further increase the transcription of genes induced by the virus (six genes over 2-fold increase relative to virus alone). Consistent with its ability to enhance the replication and spread of VSVΔ51, VSe1 potently reduced the induction of over 96% of the cellular antiviral transcripts induced by virus infection alone.

VSe1 Augments VSVΔ51 Oncolytic Activity In Vivo and in Primary Human Tumor Samples As VSe1 enhanced the oncolytic activity of VSVΔ51 in cancer cells but not normal cells in vitro we sought to determine if this level of specificity would be observed in vivo and/or in freshly explanted patient tumor material. Balb/C mice were engrafted with a VSVΔ51-resistant CT26 colon cancer cell line and tumor growth was evaluated following treatment with vehicle control, VSe1, vehicle/VSVΔ51 or VSe1/VSVΔ51. Whereas neither VSe1 nor VSVΔ51 alone had a significant effect on tumor growth, the combination of VSe1 and VSVΔ51 led to a significant delay in tumor progression. Importantly, when animals were treated with VSVΔ51 harboring the GFP gene in the presence or absence of VSe1 there was no detectable virus in any of the normal tissues of treated animals. This same specificity and magnitude of virus enhancement was seen when primary human tumour explants were infected in vitro in the presence of VSe1. An example of these experiments is demonstrated wherein VSVΔ51-GFP was added to a colon cancer sample in the presence or absence of VSe1. While in this patient sample VSVΔ51-GFP replicated poorly on its own, its growth and spread (as visualized by green fluorescence) was significantly enhanced in the presence of VSe1. The titers of virus produced in primary human tumor samples was determined in the presence of increasing amounts of VSe1. As was observed in previous tumor cell line experiments, we found that VSe1 could increase VSVΔ51 from 10 to 100 fold in primary human tumor samples of various origins. In one colorectal cancer case, adjacent normal colon tissue was isolated and VSVΔ51 on its own grew better in tumour versus adjacent normal tissues. Importantly, while treatment of the explants with VSe1 did not increase the replication of VSVΔ51 in normal tissues, it led to over 100-fold growth of VSVΔ51 in the tumour tissue, leading to roughly 1000-fold differential in replication between normal and cancerous tissues.

The present invention will be further illustrated in the following examples.

EXAMPLES

Screening Assay

In order to identify viral sensitizing agents in a high-throughput fashion, we developed an assay using 96-well plates to quantify oncolytic viral activity against cancer cells. Initially, the assay examined VSVΔ51-associated cytotoxicity against 4T1 breast cancer cells. This assay uses HEPES-buffered, phenol red free cell culture media (Gibco®) to minimize background and to minimize problems associated with pH changes that can influence VSV growth. For this assay, 30 000 4T1 cells per well are plated in 96-well plates and the cells are allowed to adhere to the plates overnight in the aforementioned media. The next day cells are pre-treated for 4 hours with a 10 μM concentration of library compounds (dissolved in 5% dimethylsulfoxide (DMSO)), which is added using a Biomek FX liquid handler, and subsequently challenged with VSVΔ51 at a multiplicity of infection (MOI) of 0.03 or a control (added using a Biotek μFill). Duplicate plates are run for each condition. On each plate, internal controls comprising cells pre-treated (at the same time as the library compounds) with either 5% DMSO (negative control) or 5 μM SAHA (positive control) are included. 40 hours later, plates are removed from the incubators and allowed to equilibrate for 2 hours at room temperature and Alamar Blue® reagent is added to the plates and a first fluorescence reading is taken immediately using a fluorescence plate reader (Perkin Elmer EnVision plate reader, 530 nm excitation, 590 emission). Plates are then incubated at room temperature for 2 hours and a second fluorescence reading is taken. The difference between the second and first reading is calculated and employed in further calculations of metabolic activity. While taking the difference between the second and the first reading is known to reduce the interfering effect of auto-fluorescent compounds, we have found that pre-equilibration of plate temperatures for 2 hours and incubation at room temperature following addition of Alamar blue is an effective way to reduce plate position effects.

Identification of Viral Sensitizing Compounds

Preferred compounds were subsequently identified on the basis of normalized metabolic activity values (cytotoxicity), where low cytotoxicity in absence of virus and high cytotoxicity in presence of virus is favored. Notably, the ratio of cell metabolic activity observed between the compound used in combination with VSVΔ51 over that of the compound used alone and the difference between these two values are used as selection criteria. The B-score is also considered for choosing hit compounds. Specifically, compounds exhibiting negative B-scores in presence of virus but exhibiting B-scores near zero without virus are considered to be potential viral sensitizers. B-score normalization uses a two-way median polish, thus taking into account row/column positional effects (Brideau et al., J Biomol Screen. 2003 December; 8(6):634-47; which is herein incorporated by reference) and preventing selection of hits based on position. To this effect, compounds which on their own exhibit near zero B-scores but show highly negative B-scores in presence of virus (suggestive of more cytotoxicity) are favored. Additionally, the difference between B-scores obtained in the presence and in absence of virus is considered as a parameter (ΔB-score) in order to identify compounds exhibiting large differences in activity in infected versus uninfected wells. Finally, duplication of the results is considered in the selection of the hits. For each parameter, stringency thresholds were established based on the mean and the standard deviation and/or based on the hit rate. Potential viral sensitizers are then identified based on four different weighted scores calculated from the different parameters described above and a compiled list of the top quartile scoring compounds was generated.

Validation of Novel Viral Sensitizing Compounds

Using the method described above, we have screened more than 13500 compounds and have identified many viral sensitizing agents. Those compounds that met stringent cut-off criteria were analyzed further for structural similarities as described herein. Compounds were validated when independent tests twice showed enhanced VSVΔ51 spread and oncolytic activity in 4T1 cells by two or more of the following methods: fluorescence microscopy (viral spread), coomassie blue assay (cell detachment, cytotoxicity), alamar blue assay (metabolic activity, cytotoxicity), or plaque assay (viral titer). Initial testing is done within a given dose range near that used for the screen (between 20 μM and 2.5 μM).

One viral sensitizing agent identified by the screening method that exhibited high activity was 3,4-dichloro-5-phenyl-2,5-dihydrofuran-2-one (DCPDF). We confirmed that DCPDF increased the spread of VSVΔ51 in 4T1 breast cancer cells, and found it also enhanced the spread of VSVΔ51 in CT26 colon cancer cells, 786-0 human renal carcinoma cells and U251 human glioblastoma cells (FIGS. 1, 2, 5A). However, DCPDF did not enhance the spread of VSVΔ51 in normal human GM38 fibroblasts (FIG. 5A).

DCPDF increased the titers of VSVΔ51 in several cell lines including 786-0, CT26 and 4T1 (FIGS. 4, 5B, 5C). In CT26 cells, pre-treatment with DCPDF increased VSVΔ51 titers more than 1000 fold compared to the control treated cells (FIGS. 4, 5B). The effect of DCPDF on viral output was also found to be concentration dependent (FIG. 5C).

Isobologram analyses based on the method of Chou and Talalay (Chou and Talalay (1977) J. Biol. Chem. 252:6438-6442, which is herein incorporated by reference) confirmed that DCPDF led to bone fide synergistic cell killing when used in combination with VSVΔ51 in both 4T1 and CT26 cells (FIG. 6A). This can also be visualized by coomassie staining in FIGS. 3 and 6B.

We also examined whether DCPDF could enhance the spread of other oncolytic viruses. In B16 melanoma cells as well as in 4T1 cells, we observed enhanced spread and viral output of a genetically attenuated strain of vaccinia virus (VVdd, deleted for thymidine kinase and vaccinia growth factor genes; FIGS. 7A and 7B) (McCart et al., 2001 Cancer Res. December 15; 61(24):8751-7, which is herein incorporated by reference). Without wishing to be bound by theory or limiting in any manner, preliminary data suggests that DCPDF alters cell cycle progression, where cells ultimately accumulate in G1. Notably the kinetics of cell cycle arrest appears to be distinct from that observed with TSA, an HDI that also blocks the cell cycle in G1 (FIGS. 8A and 8B). Finally, without wishing to be bound by theory or limiting in any manner, DCPDF may work in part by overcoming IFN response as U251 cells protected with IFN were partially re-sensitized to VSVΔ51 following treatment with DCPDF (FIG. 9).

Other Novel Viral Sensitizing Compounds

Subsequent to validating the highly active viral sensitizing agent DCPDF, we went on to validate other viral sensitizing compounds according to the criteria mentioned previously. The compounds were initially tested as soon as they were identified from the screen; subsequently, priority was given to molecules exhibiting a similar structure to DCPDF, based on the characteristic 5-atom furane ring and possible substitution of the oxygen atom of the furane ring with another electronegative atom such as nitrogen or sulfur. Additional viral sensitizing compounds were identified and validated (see FIGS. 10A to 10J) and their structures were further studied to determine common underlying structural features that supported viral sensitizing activity. Upon close inspection of the compounds identified from the screen, we found that several compounds could be grouped by structural similarity as described herein.

Materials, Methods and Other Technical Details

Drugs and Chemicals: Compounds used for the high throughput screen were a selected subset from the Maybridge HitFinder, Chembridge DIVERSet, Microsource Spectrum, Prestwick, BIOMOL, and Sigma LOPAC screening collections. Selection of compounds was based on chemical diversity and non-overlap. All compounds were dissolved at 10 mM in DMSO. For further in vitro testing, VSe1 (also known as 3,4-dichloro-5-phenyl-2,5-dihydrofuran-2-one or DCPDF) was obtained from Ryan Scientific (Mt. Pleasant, S.C., USA) and dissolved in DMSO at 10 mM. For in vivo use, VSe1 was dissolved fresh in 30% ethanol, 5% DMSO (in PBS) at 0.4 mg per 50 μl SAHA was obtained from Exclusive Chemistry (Obninsk, Russia) and also dissolved in DMSO at 10 mM. Both were stored at −20° C. IFNα treatment was performed using Intron A (Shering), stored at 40 C at stock concentration $10\times10^6$IU/ml.

Cell lines: The following cell lines were purchased from the American Type Culture Collection: 4T1 (mouse breast adenocarcinoma), B16 (mouse melanoma), 786-0 (human renal cancer), U251 (human glioma), GM38 (normal human fibroblast), HEK 293T (Human embryonic kidney), U20S (human osteosarcoma) and Vero (monkey kidney cells). All cell lines, except GM38, were cultured in HyQ High glucose Dulbecco's modified Eagle medium (DMEM) (HyClone) supplemented with 10% fetal calf serum (CanSera, Etobicoke, Canada). GM38 cells were grown in DMEM supplemented with 20% fetal bovine serum (Gibco). All cell lines were incubated at 37 degrees in a 5% CO2 humidified incubator.

Viruses: The Indiana serotype of VSV (mutant or wild type) was used throughout this study and was propagated in Vero cells. VSVΔ51 is a naturally occurring interferon-inducing mutant of the heat-resistant strain of wild-type VSV Indiana, while VSVΔ51 expressing RFP or GFP are recombinant derivatives of VSVΔ51 (49). Virions were purified from cell culture supernatants by passage through a 0.2 μm Steritop filter (Millipore, Billerica, Mass.) and centrifugation at 30,000 g before resuspension in PBS (HyClone, Logan, Utah). For the High throughput screen, 30% sucrose was added to increase virus stability. For in vivo studies, virus was further purified on 5-50% Optiprep® (Sigma) gradient. Doubled deleted vaccinia virus (VVdd) expressing fluorescent Cherry protein was obtained by homologous recombination with VVdd-GFP and was propagated in U20S cells.

High Throughput Screening: 4T1 cells were plated in HEPES-buffered, phenol red free DMEM (Gibco) in 96-well plates and allowed to adhere overnight. The next day, 95% confluent cells were pre-treated for 4 hours with a 10 μM concentration of library compounds added using a Biomek FX liquid handler (Beckman Coulter, Fullerton, Calif., USA), and subsequently challenged with VSVΔ51 at an MOI of 0.0325 or a control added using a μFill liquid handler (Biotek, Winooski, Vt., USA). Duplicate plates were run for each condition. On each plate, internal controls consisting of cells pre-treated (at the same time as the library compounds) with DMSO (negative control) were included. 40 hours later, plates were incubated with Alamar Blue® and fluorescence emission rate was assessed using an EnVision plate reader (Perkin Elmer, Waltham, Mass., USA). Cytotoxicity of each drug was determined in both presence and absence of virus and was defined as follows: Cytotoxicity in presence of VSVΔ51 (VSV)=fluorescence rate in presence of drug+VSVΔ51 divided by average fluorescence rate of the DMSO+VSVΔ51 controls (eight per plate). Cytotoxicity in absence of VSVΔ51 (CTRL)=fluorescence rate in presence of drug (but no virus) divided by average fluorescence rate of the DMSO control (no virus, eight per plate). Cell killing induced by virus alone was assessed by comparing DMSO controls on infected and mock-infected plates and was below 10%. Average Log (VSV/CTRL) values for the duplicates were used as the parameter for selection of hits, where −0.3 was the cutoff value. Reproducibility of the Log (VSV/CTRL) values across the duplicates was also considered in the selection.

Viral titers: Supernatants from each treatment condition were collected at the specified time point. A serial dilution was then performed in serum-free DMEM and 500 μl of each dilution was applied to a confluent monolayer of Vero cells for 45 minutes. Subsequently, the plates were overlayed with 0.5% agarose in DMEM-10% FBS and the plaques were grown for 24 h. Carnoy fixative (Methanol:Acetic Acid is 3:1) was then applied directly on top of the overlay for 5 minutes. The overlay was gently lifted off using a spatula and the fixed monolayer was stained via 0.5% coomassie blue for 30 minutes, after which the plaques were counted. VVDD samples were tittered on U20S monolayer using 1.5% carboxyl methyl-cellulose in DMEM-10% FBS for 48 h. The overlay was removed and the monolayer stained via 0.5% coomassie blue for 30 minutes, after which the plaques were counted.

Assessment of combination index: 25 000 4T1 or CT26 cells were plated per well in 96 well plates and left to adhere over night. The following day, cells were pre-treated for 4 hours with serial dilutions of Vse1 (200 μM to 1.5 μM, 1:2 dilution steps) then infected with serial dilutions of VSVΔ51 (100000 PFU to 780 PFU) keeping a fixed ratio combination of VSVΔ51 and VSe1 (500 PFU to 1 μM). Cytotoxicity was assessed using Alamar blue reagent after 48 h. Combination indices (CI) were calculated using the Calcusyn Software (Biosoft, Ferguson Mo., USA) according to the method of Chou and Talalay (Chou and Talalay (1977) J. Biol. Chem. 252:6438-6442).

Reporter assays: HEK 293T cells were plated at $1.3 \times 10^5$ cells/well in 24-well dishes. The following day, cells were co-transfected with an ISRE-driven luciferase reporter plasmid as described previously (Lai, F et al. (2008). J Virol Methods 153: 276-279) and a CMV-driven (3-galactosidase control plasmid. 6 Hours post-transfection, cells were treated with VSe1 or mock treated with vehicle. Approximately 20 hours after receiving VSe1, cells were then treated with IFN-α with a complete media change. The following day, cells were lysed and measured for luciferase using the BD Monolight kit (Becton Dickinson, Franklin Lakes, N.J., USA). β-galactosidase activity was measured using the Luminescent β-galactosidase kit (Clontech, Mountainview, Calif., USA).

HDAC enzymatic activity assays: Activity of recombinant HDACs 1 through 11 were tested in presence of either VSe1 20 μM or TSA 20 μM by Reaction Biology Corp. (Malvern, Pa., USA) using 50 μM of a fluorogenic peptide from p53 residues 379-382 (RHKKAc for HDAC 1-7 and 9-11 or RHKAcKAc for HDAC8). HDAC activity was compared to control treated with DMSO (vehicle) and expressed as a percentage of HDAC activity in the control. All conditions were tested in duplicate.

Microarrays: CT26 cells were plated at a density of $1.5 \times 10^6$ in 100 mm petris and allowed to adhere overnight. The next day, cells were treated with either DMSO, 20 μM VSe1 or 5 μM SAHA. Four hours later, VSVΔ51 (or control media) was added at an MOI of 0.03. Twenty four hours post-infection, cells were collected using a rubber scraper in a small volume of PBS. Cell pellets were subsequently used for total RNA extraction using Qiagen QiaShredder columns and the Qiagen RNeasy extraction kit (Qiagen, Valencia, Calif., USA). A pooled duplicate sample RNA was used for subsequent hybridization on microarray. RNA quality was confirmed using an Agilent 2100 Bioanalyzer (Santa Clara, Calif., USA) prior to labeling of RNA and hybridization onto Affymetrix mouse gene 1.0 ST arrays according to manufacturer instructions. Low signal genes (<50 in DMSO-treated, mock-infected control) were removed from the data set. Expression of the remaining genes was normalized to average overall signal for each array. Subsequently the fold change in gene expression was calculated for each gene in relation to the mock-infected, DMSO-treated control. A 2-fold change in gene expression relative to the control was used as a cutoff for selection of treatment-perturbed genes. Analysis was done using Microsoft Excel.

Animal tumor model: Syngenic colon carcinoma tumors were established subcutaneously in the hind flanks of 6 week old female Balb/c mice by injecting $3 \times 10^5$ of VSVΔ51-resistant CT26 cells suspended in 100 μl PBS. By day 11 post-implantation, tumors had reached an approximate average size of 220 mm$^3$ and mice were treated with a 0.4 mg dose of VSe1 resuspended in 30% ethanol 5% DMSO, 65% PBS (or vehicle control) administered intraperitoneally. VSVΔ51 ($1 \times 10^8$ pfu) was introduced intratumorally 4 h following the first VSe1 dose. Subsequently, VSe1 (or vehicle) was re-administered on day 13 and day 15 post implantation (0.4 mg/injection/mouse). Tumor sizes were measured every 2-3 days using an electronic caliper. Tumor volume was calculated as =(length×width)/2. Relative tumor size for each mouse at each time point was calculated relative to the initial tumor size measured on day 11. ANOVA was used to assess statistical significance of observed differences at each time point.

Treatment and processing of primary tissue specimens: Primary tissue specimens were obtained from consenting patients who underwent tumor resection. All tissues were processed within 48 h post surgical excision. 300 μm tissue slices were obtained using a Krumdieck tissue slicer (Alabama research and development, Munford, Ala., USA) and plated in DMEM supplemented with 10% FBS. After the indicated treatment conditions, samples were visualized by fluorescence microscopy. Tissues were subsequently weighed and homogenized in 1 ml of PBS using a homogenizer (Kinematica AG-PCU-11). Serial dilutions of tissue homogenates were prepared in serum free media and viral titers were quantified by standard plaque assay.

Realtime PCR: 2 μg RNA was used to synthesize cDNA using the SuperScript first-strand synthesis system (random hexamer method) according to manufacturers instructions (Invitrogen, ON, Canada). The QuantiTect SYBR Green PCR kit was used as recommended (Qiagen, ON, Canada). Real time PCR reactions were performed on a Rotor-gene RG-300 (Corbett Research, Australia). Optimal threshold and reaction efficiency were determined using the Rotor-gene software. Melt curves for each primer exhibited a single peak, indicating specific amplification, which was also confirmed by agarose gel. Ct values were determined using the Rotor-gene software at the optimal threshold previously determined for each gene. Gene expression relative to GAPDH was calculated. Fold induction was calculated relative to the DMSO treated control for each gene. Primers were designed using Primer 3 v 4.0

All citations are hereby incorporated by reference.

The present invention has been described with regard to one or more embodiments. However, it will be apparent to persons skilled in the art that a number of variations and modifications can be made without departing from the scope of the invention as defined in the claims.

REFERENCES

1. Adusumilli P S, Chan M K, Chun Y S, Hezel M, Chou T C, Rusch V W et al. (2006). Cisplatin-induced GADD34 upregulation potentiates oncolytic viral therapy in the treatment of malignant pleural mesothelioma. Cancer Biol Ther; 5: 48-53.
2. Ahmed, M., S. D. Cramer, and D. S. Lyles, Sensitivity of prostate tumors to wild type and M protein mutant vesicular stomatitis viruses. Virology, 2004. 330(1): p. 34-49.
3. Bennett J J, Adusumilli P, Petrowsky H, Burt B M, Roberts G, Delman K A et al. (2004). Upregulation of GADD34 mediates the synergistic anticancer activity of mitomycin C and a gamma134.5 deleted oncolytic herpes virus (G207). FASEB J; 18: 1001-1003.
4. Brideau, C., B. Gunter, B. Pikounis, and A. Liaw, Improved statistical methods for hit selection in high-throughput screening. J Biomol Screen, 2003. 8(6): p. 634-47.
5. Chalikonda S, Kivlen M H, O'Malley M E, Eric Dong X D, McCart J A, Gorry M C et al. (2008). Oncolytic virotherapy for ovarian carcinomatosis using a replication-selective vaccinia virus armed with a yeast cytosine deaminase gene. Cancer Gene Ther; 15: 115-125.
6. Chang, H. M., M. Paulson, M. Holko, C. M. Rice, B. R. Williams, I. Marie, and D. E. Levy, Induction of interferon-stimulated gene expression and antiviral responses require protein deacetylase activity. Proc Natl Acad Sci USA, 2004. 101(26): p. 9578-83.
7. Chen G, Zhou J, Gao Q, Huang X, Li K, Zhuang L et al. (2006). Oncolytic adenovirus-mediated transfer of the antisense chk2 selectively inhibits tumor growth in vitro and in vivo. Cancer Gene Ther; 13: 930-939.
8. Cheong S C, Wang Y, Meng J H, Hill R, Sweeney K, Kim D et al. (2008). E1A-expressing adenoviral E3B mutants act synergistically with chemotherapeutics in immunocompetent tumor models. Cancer Gene Ther; 15: 40-50.
9. Chou, T. C. and P. Talaly, A simple generalized equation for the analysis of multiple inhibitions of Michaelis-Menten kinetic systems. J Biol Chem, 1977. 252(18): p. 6438-42.
10. Ebert, O., S. Harbaran, K. Shinozaki, and S. L. Woo, Systemic therapy of experimental breast cancer metastases by mutant vesicular stomatitis virus in immune-competent mice. Cancer Gene Ther, 2005. 12(4): p. 350-8.
11. Foloppe J, Kintz J, Futin N, Findeli A, Cordier P, Schlesinger Y et al. (2008). Targeted delivery of a suicide gene to human colorectal tumors by a conditionally replicating vaccinia virus. Gene Ther; 15: 1361-1371.
12. Freytag S O, Barton K N, Brown S L, Narra V, Zhang Y, Tyson D et al. (2007). Replicationcompetent adenovirus-mediated suicide gene therapy with radiation in a preclinical model of pancreatic cancer. Mol Ther; 15: 1600-1606.
13. Fukuda K, Abei M, Ugai H, Kawashima R, Seo E, Wakayama M et al. (2009). E1A, E1B doublerestricted replicative adenovirus at low dose greatly augments tumor-specific suicide gene therapy for gallbladder cancer. Cancer Gene Ther; 16: 126-136.
14. Galanis E, Okuno S H, Nascimento A G, Lewis B D, Lee R A, Oliveira A M et al. (2005). Phase I-11 trial of ONYX-015 in combination with MAP chemotherapy in patients with advanced sarcomas. Gene Ther; 12: 437-445.
15. Gao Q, Zhou J, Huang X, Chen G, Ye F, Lu Y et al. (2006). Selective targeting of checkpoint kinase 1 in tumor cells with a novel potent oncolytic adenovirus. Mol Ther; 13: 928-937.
16. Graat H C, Witlox M A, Schagen F H, Kaspers G J, Helder M N, Bras J et al. (2006). Different susceptibility of osteosarcoma cell lines and primary cells to treatment with oncolytic adenovirus and doxorubicin or cisplatin. Br J Cancer; 94: 1837-1844.
17. Hsieh J L, Lee C H, Teo M L, Lin Y J, Huang Y S, Wu C L et al. (2009). Transthyretin-driven oncolytic adenovirus suppresses tumor growth in orthotopic and ascites models of hepatocellular carcinoma. Cancer Sci; 100: 537-545.
18. Hsu K F, Wu C L, Huang S C, Hsieh J L, Huang Y S, Chen Y F et al. (2008). Conditionally replicating E1B-deleted adenovirus driven by the squamous cell carcinoma antigen 2 promoter for uterine cervical cancer therapy. Cancer Gene Ther; 15: 526-534.
19. Ikeda K, Ichikawa T, Wakimoto H, Silver J S, Deisboeck T S, Finkelstein D et al. (1999). Oncolytic virus therapy of multiple tumors in the brain requires suppression of innate and elicited antiviral responses. Nat Med 5: 881-887.
20. Ikeda K, Wakimoto H, Ichikawa T, Jhung S, Hochberg F H, Louis D N et al. (2000). Complement depletion facilitates the infection of multiple brain tumors by an intravascular, replicationconditional herpes simplex virus mutant. J Virol; 74: 4765-4775.
21. Kambara H, Saeki Y, Chiocca E A (2005). Cyclophosphamide allows for in vivo dose reduction of a potent oncolytic virus. Cancer Res; 65: 11255-11258.
22. Kasuya H, Nishiyama Y, Nomoto S, Goshima F, Takeda S, Watanabe I et al. (2007). Suitability of a US3-inactivated HSV mutant (L1BR1). as an oncolytic virus for pancreatic cancer therapy. Cancer Gene Ther; 14: 533-542.
23. Kim E J, Yoo J Y, Choi Y H, Ahn K J, Lee J D, Yun C O et al. (2008). Imaging of viral thymidine kinase gene expression by replicating oncolytic adenovirus and prediction of therapeutic efficacy. Yonsei Med J; 49: 811-818.
24. Kottke T, Thompson J, Diaz R M, Pulido J, Willmon C, Coffey M et al. (2009). Improved Systemic Delivery of Oncolytic Reovirus to Established Tumors Using Preconditioning with Cyclophosphamide-Mediated Treg Modulation and Interleukin-2. Clin Cancer Res; 15: 561-569.
25. Kramm C M, Rainov N G, Sena-Esteves M, Barnett F H, Chase M, Herrlinger U et al. (1996). Longterm survival in a rodent model of disseminated brain tumors by combined intrathecal delivery of herpes vectors and ganciclovir treatment. Hum Gene Ther; 7: 1989-1994.
26. Kurozumi K, Hardcastle J, Thakur R, Shroll J, Nowicki M, Otsuki A et al. (2008). Oncolytic HSV-1 infection of tumors induces angiogenesis and upregulates CYR61. Mol Ther; 16: 1382-1391.
27. Kurozumi K, Hardcastle J, Thakur R, Yang M, Christoforidis G, Fulci G et al. (2007). Effect of tumor microenvironment modulation on the efficacy of oncolytic virus therapy. J Natl Cancer Inst; 99: 1768-1781.
28. Lun X Q, Jang J N, Tang N, Deng H, Bell J C, Stojdl D F et al. (2009). Efficacy of systemically administered oncolytic vaccinia virotherapy for malignant gliomas is enhanced by combination therapy with rapamycin or cyclophosphamide. Clin Cancer Res; 15: 2777-2788.
29. Lun X Q, Zhou H, Alain T, Sun B, Wang L, Barrett J W et al. (2007). Targeting human medulloblastoma: oncolytic virotherapy with myxoma virus is enhanced by rapamycin. Cancer Res; 67: 8818-8827.
30. Lun, X., D. L. Senger, T. Alain, A. Oprea, K. Parato, D. Stojdl, B. Lichty, A. Power, R. N. Johnston, M. Hamilton, I. Parney, J. C. Bell, and P. A. Forsyth, Effects of intravenously administered recombinant vesicular stomatitis virus (VSV(deltaM51)) on multifocal and invasive gliomas. J Natl Cancer Inst, 2006. 98(21): p. 1546-57.
31. Mace A T, Harrow S J, Ganly I, Brown S M (2007). Cytotoxic effects of the oncolytic herpes simplex virus HSV1716 alone and in combination with cisplatin in head and neck squamous cell carcinoma. Acta Otolaryngol; 127: 880-887.
32. Mai, A., S. Valente, A. Nebbioso, S. Simeoni, R. Ragno, S. Massa, G. Brosch, F. De Bellis, F. Manzo, and L. Altucci, New pyrrole-based histone deacetylase inhibitors: binding mode, enzyme- and cell-based investigations. Int J Biochem Cell Biol, 2009. 41(1): p. 235-47.
33. McCart J A, Puhlmann M, Lee J, Hu Y, Libutti S K, Alexander H R et al. (2000). Complex interactions between the replicating oncolytic effect and the enzyme/prodrug effect of vaccinia mediated tumor regression. Gene Ther; 7: 1217-1223.
34. Monneret, C., Histone deacetylase inhibitors. Eur J Med Chem, 2005. 40(1): p. 1-13.
35. Mullerad M, Bochner B H, Adusumilli P S, Bhargava A, Kikuchi E, Hui-Ni C et al. (2005). Herpes simplex virus based gene therapy enhances the efficacy of mitomycin C for the treatment of human bladder transitional cell carcinoma. J Urol; 174: 741-746.
36. Nawa A, Nozawa N, Goshima F, Nagasaka T, Kikkawa F, Niwa Y et al. (2003). Oncolytic viral therapy for human ovarian cancer using a novel replication-competent herpes simplex virus type I mutant in a mouse model. Gynecol Oncol; 91: 81-88.
37. Nguyen, T. L., H. Abdelbary, M. Arguello, C. Breitbach, S. Leveille, J. S. Diallo, A. Yasmeen, T. A. Bismar, D. Kim, T. Falls, V. E. Snoulten, B. C. Vanderhyden, J. Werier, H. Atkins, M. J. Vaha-Koskela, D. F. Stojdl, J. C. Bell, and J. Hiscott, Chemical targeting of the innate antiviral response by histone deacetylase inhibitors renders refractory cancers sensitive to viral oncolysis. Proc Natl Acad Sci USA, 2008. 105(39): p. 14981-6.
38. Pan Q, Liu B, Liu J, Cai R, Wang Y, Qian C (2007). Synergistic induction of tumor cell death by combining cisplatin with an oncolytic adenovirus carrying TRAIL. Mol Cell Biochem; 304: 315-323.
39. Pan Q W, Zhong S Y, Liu B S, Liu J, Cai R, Wang Y G et al. (2007). Enhanced sensitivity of hepatocellular carcinoma cells to chemotherapy with a Smac-armed oncolytic adenovirus. Acta Pharmacol Sin; 28: 1996-2004.
40. Parato, K. A., D. Senger, P. A. Forsyth, and J. C. Bell, Recent progress in the battle between oncolytic viruses and tumors. Nat Rev Cancer, 2005. 5(12): p. 965-76.
41. Pawlik T M, Nakamura H, Mullen J T, Kasuya H, Yoon S S, Chandrasekhar S et al. (2002). Prodrug bioactivation and oncolysis of diffuse liver metastases by a herpes simplex virus 1 mutant that expresses the CYP2B1 transgene. Cancer; 95: 1171-1181.
42. Qiao J, Wang H, Kottke T, White C, Twigger K, Diaz R M et al. (2008). Cyclophosphamide Facilitates Antitumor Efficacy against Subcutaneous Tumors following Intravenous Delivery of Reovirus. Clin Cancer Res; 14: 259-269.
43. Reddy, P. S., K. D. Burroughs, L. M. Hales, S. Ganesh, B. H. Jones, N. Idamakanti, C. Hay, S. S. Li, K. L. Skele, A. J. Vasko, J. Yang, D. N. Watkins, C. M. Rudin, and P. L. Hallenbeck, Seneca Valley virus, a systemically deliverable oncolytic picornavirus, and the treatment of neuroendocrine cancers. J Natl Cancer Inst, 2007. 99(21): p. 1623-33.
44. Ryan P C, Jakubczak J L, Stewart D A, Hawkins L K, Cheng C, Clarke L M et al. (2004). Antitumor efficacy and tumor-selective replication with a single intravenous injection of OAS403, an oncolytic adenovirus dependent on two prevalent alterations in human cancer. Cancer Gene Ther; 11: 555-569.
45. Sieben M, Herzer K, Zeidler M, Heinrichs V, Leuchs B, Schuler M et al. (2008). Killing of p53-deficient hepatoma cells by parvovirus H-1 and chemotherapeutics requires promyelocytic leukemia protein. World J Gastroenterol; 14: 3819-3828.
46. Stanford M M, Barrett J W, Nazarian S H, Werden S, McFadden G (2007). Oncolytic virotherapy synergism with signaling inhibitors: Rapamycin increases myxoma virus tropism for human tumor cells. J Virol; 81: 1251-1260.
47. Stanford M M, Shaban M, Barrett J W, Werden S J, Gilbert P A, Bondy-Denomy J et al. (2008). Myxoma virus oncolysis of primary and metastatic B 16F10 mouse tumors in vivo. Mol Ther 16: 52-59.
48. Stojdl, D. F., B. Lichty, S. Knowles, R. Marius, H. Atkins, N. Sonenberg, and J. C. Bell, Exploiting tumor-specific defects in the interferon pathway with a previously unknown oncolytic virus. Nat Med, 2000. 6(7): p. 821-5.
49. Stojdl, D. F., B. D. Lichty, B. R. tenOever, J. M. Paterson, A. T. Power, S. Knowles, R. Marius, J. Reynard, L. Poliquin, H. Atkins, E. G. Brown, R. K. Durbin, J. E. Durbin, J. Hiscott, and J. C. Bell, VSV strains with defects in their ability to shutdown innate immunity are potent systemic anti-cancer agents. Cancer Cell, 2003. 4(4): p. 263-75.
50. Sung C K, Choi B, Wanna G, Genden E M, Woo S L, Shin E J (2008). Combined VSV oncolytic virus and chemotherapy for squamous cell carcinoma. Laryngoscope; 118: 237-242.
51. Taneja, S., J. MacGregor, S. Markus, S. Ha, and I. Mohr, Enhanced antitumor efficacy of a herpes simplex virus mutant isolated by genetic selection in cancer cells. Proc Natl Acad Sci USA, 2001. 98(15): p. 8804-8.
52. Thomas M, Spencer J F, Toth K, Sagartz J E, Phillips N J, Wold W S (2008). Immunosuppression enhances oncolytic adenovirus replication and antitumor efficacy in the Syrian hamster model. Mol Ther; 16:1665-1673.
53. Tomicic M T, Thust R, Kaina B (2002). Ganciclovir-induced apoptosis in HSV-1 thymidine kinase expressing cells: critical role of DNA breaks, Bcl-2 decline and caspase-9 activation. Oncogene; 21: 2141-2153.
54. Toyoizumi T, Mick R, Abbas A E, Kang E H, Kaiser L R, Molnar-Kimber K L (1999). Combined therapy with chemotherapeutic agents and herpes simplex virus type 1 ICP34.5 mutant (HSV-1716). in human non-small cell lung cancer. Hum Gene Ther; 10: 3013-3029.
55. Tumilasci V F, Oliere S, Nguyen T L, Shamy A, Bell J, Hiscott J (2008). Targeting the apoptotic pathway with BCL-2 inhibitors sensitizes primary chronic lymphocytic leukemia cells to vesicular stomatitis virus-induced oncolysis. J Virol; 82: 8487-8489.
56. Ungerechts G, Springfeld C, Frenzke M E, Lampe J, Parker W B, Sorscher E J et al. (2007). An immunocompetent murine model for oncolysis with an armed and targeted measles virus. Mol Ther; 15: 1991-1997.
57. Yoon A R, Kim J H, Lee Y S, Kim H, Yoo J Y, Sohn J H et al. (2006). Markedly enhanced cytolysis by E1B-19kD-deleted oncolytic adenovirus in combination with cisplatin. Hum Gene Ther; 17: 379-390.
58. Yu D C, Chen Y, Dilley J, Li Y, Embry M, Zhang H et al. (2001). Antitumor synergy of CV787, a prostate cancer-specific adenovirus, and paclitaxel and docetaxel. Cancer Res; 61: 517-525.
59. Yu Y A, Galanis C, Woo Y, Chen N, Zhang Q, Fong Y et al. (2009). Regression of human pancreatic tumor xenografts in mice after a single systemic injection of recombinant vaccinia virus GLV-1h68. Mol Cancer Ther; 8: 141-151.
60. Zhang J, Ramesh N, Chen Y, Li Y, Dilley J, Working P et al. (2002). Identification of human uroplakin II promoter and its use in the construction of CG8840, a urothelium-specific adenovirus variant that eliminates established bladder tumors in combination with docetaxel. Cancer Res; 62: 3743-3750.
61. Zhang N H, Song L B, Wu X J, Li R P, Zeng M S, Zhu X F et al. (2008). Proteasome inhibitor MG-132 modifies coxsackie and adenovirus receptor expression in colon cancer cell line lovo. Cell Cycle; 7: 925-933.
62. Zhou J, Gao Q, Chen G, Huang X, Lu Y, Li K et al. (2005). Novel oncolytic adenovirus selectively targets tumor-associated polo-like kinase 1 and tumor cell viability. Clin Cancer Res; 11: 8431-8440.

What is claimed is:

1. A method of enhancing the production of a virus in a cell comprising producing a composition comprising the virus and a viral sensitizing agent, by administering the viral sensitizing agent to said cells prior to, after, or concurrently with the virus, and culturing the virus and cells to enhance the production of the virus in said cells, and wherein the viral sensitizing agent is [di(methylthio)methylidene]malononitrile, and wherein the virus is attenuated or genetically modified.

2. A method of enhancing the production of a virus in a cell comprising producing a composition comprising the virus and a viral sensitizing agent, by administering the viral sensitizing agent to said cells prior to, after, or concurrently with the virus, and culturing the virus and cells to enhance the production of the virus in said cells, and wherein the viral sensitizing agent is [di(methylthio)methylidene]malononitrile, and wherein the virus is a rhabdovirus, vaccinia virus, or influenza virus.

3. A method of enhancing the production of a virus in a cell comprising producing a composition comprising the virus and a viral sensitizing agent, by administering the viral sensitizing agent to said cells prior to, after, or concurrently with the virus, and culturing the virus and cells to enhance the production of the virus in said cells, and wherein the viral sensitizing agent is [di(methylthio)methylidene]malononitrile, and wherein the cells are cancer cells, tumor cells, or cells which have been immortalized.

4. The method of claim 3 wherein the cells are MDCK, HEK293, Vero, HeLa, or PER.C6 cells.

5. A method of enhancing the production of a virus in a cell comprising producing a composition comprising the virus and a viral sensitizing agent, by administering the viral sensitizing agent to said cells prior to, after, or concurrently with the virus, and culturing the virus and cells to enhance the production of the virus in said cells, and wherein the viral sensitizing agent is [di(methylthio)methylidene]malononitrile, and wherein the cells are in vivo in a subject.

6. The method of claim 5 wherein the subject is an animal subject.

7. The method of claim 6 wherein the subject is a human subject.

8. A composition comprising a viral sensitizing agent and one or both of a virus and a cell which is capable of being infected by the virus, and wherein the viral sensitizing agent is [di(methylthio)methylidene]malononitrile.

9. The composition of claim 8 comprising [di(methylthio)methylidene]malononitrile, the virus and the cell which is capable of being infected by the virus for enhancing the production of the virus in the cell by administering the [di(methylthio)methylidene]malononitrile to said cells prior to, after, or concurrently with the virus, and culturing the virus and cells to enhance the production of the virus in said cells.

* * * * *